United States Patent [19]

Shiokawa et al.

[11] Patent Number: 5,102,878

[45] Date of Patent: *  Apr. 7, 1992

[54] PHARMACEUTICAL METHOD OF TREATMENT USING PYRAZOLOPYRIDINE COMPOUND

[75] Inventors: Youichi Shiokawa, Ibaraki; Atsushi Akahane, Kawabe; Hirohito Katayama, Nishinomiya; Takafumi Mitsunaga, Ashiya, all of Japan

[73] Assignee: Fujisawa Pharmaceutical Co., Ltd., Osaka, Japan

[ * ] Notice: The portion of the term of this patent subsequent to May 15, 2007 has been disclaimed.

[21] Appl. No.: 495,799

[22] Filed: Mar. 19, 1990

Related U.S. Application Data

[63] Continuation-in-part of Ser. No. 407,747, Sep. 15, 1989, Pat. No. 4,994,453, which is a continuation-in-part of Ser. No. 202,526, Jun. 6, 1988, Pat. No. 4,925,849.

[30] Foreign Application Priority Data

Jun. 15, 1987 [GB] United Kingdom ............... 8713908
Aug. 20, 1987 [GB] United Kingdom ............... 8719724
Dec. 31, 1987 [GB] United Kingdom ............... 8730330

[51] Int. Cl.$^5$ ............................................. A61K 31/435
[52] U.S. Cl. ................................... 514/212; 514/216; 514/233.2; 514/253; 514/300
[58] Field of Search ............ 514/212, 300, 216, 233.2, 514/253

[56] References Cited

U.S. PATENT DOCUMENTS 4,925,849  5/1990  Shiokawa et al. ................... 514/300

OTHER PUBLICATIONS

Dorland's Illustrated Medical Dictionary, 24th Ed., W. B. Saunders Co., pp. 1030, 1579 & 1580 (1965).

*Primary Examiner*—Bernard Dentz
*Attorney, Agent, or Firm*—Oblon, Spivak, McClelland, Maier & Neustadt

[57] ABSTRACT

The invention relates to a method for the treatment of ailments which comprises administering an effective amount of the pyrazolopyridine compounds of the invention.

1 Claim, No Drawings

PHARMACEUTICAL METHOD OF TREATMENT USING PYRAZOLOPYRIDINE COMPOUND

This application is a continuation-in-part of parent application Ser. No. 407,747, filed Sept. 15, 1989, now U.S. Pat. No. 4,994,453, which in turn is a continuation-in-part of application Ser. No. 202,526, filed June 6, 1988, now U.S. Pat. No. 4,925,849.

The present invention relates to novel pyrazolopyridine compound and a pharmaceutically acceptable salt thereof.

More particularly, it relates to novel pyrazolopyridine compound and a pharmaceutically acceptable salt thereof, which are adenosine antagonists and possess various pharmaceutical actions such as cognitive enhancing action, analgesic action, locomotor action, antidepressant action, cerebral vasodilating action, diuretic action, cardiotonic action, vasodilating action, the action of increasing the renal blood flow, enhanced lipolysis action, inhibited anaphylactic bronchoconstrictive action, accelerating action of the release of insulin, or the like, and so are useful as psychostimulant, analgesic, antidepressant, ameliorants of cerebral circulation, remedy for heart failure, cardiotonic agent, antihypertensive agent, remedy for renal insufficiency, diuretic, remedy for edema, antiobesity, antiasthmatic, bronchoconstrictor, remedy for apnea, remedy for gout, remedy for hyperuricemia, remedy for sudden infant death syndrome (SIDS), ameliorants of immunosuppresion action of adenosine, antidiabetic agent, or the like, and further which are inhibitors of platelet aggregation, so are useful as remedy for thrombosis, remedy for myocardiac infarction, remedy for obstruction, remedy for arteriosclerosis obliterans, remedy for thrombophlebitis, remedy for cerebral infarction, remedy for transient ischemic attack, remedy for angina pectoris, or the like; to a process for preparation thereof, to a pharmaceutical composition comprising the same, and to a method for using the same therapeutically in human being and animals for the treatment of melancholia, heart failure, hypertension (e.g. essential hypertension, nephrogenous hypertension, etc.), renal insufficiency, edema (e.g. cardiac edema, nephrotic edema, hepatic edema, idiopathic edema, drug edema, acute angioneurotic edema, hereditary angioneurotic edema, carcinomatous ascites, gestational edema, etc.), obesity, bronchial asthma, gout, hyperuricemia, sudden infant death syndrome, immunosuppresion, diabetes, myocardiac infarction, thrombosis (e.g. arterial thrombosis, cerebral thrombosis, etc.), obstruction, arteriosclerosis obliterans, thrombophlebitis, cerebral infarction, transient ischemic attack, angina pectoris or the like.

Accordingly, one object of the present invention is to provide the novel pyrazolopyridine compound and a pharmaceutically acceptable salt thereof, which are useful as stated above.

Another object of the present invention is to provide processes for the preparation of the novel pyrazolopyridine compound or a salt thereof.

A further object of the present invention is to provide a pharmaceutical composition comprising, as an active ingredient, said pyrazolopyridine compound or a pharmaceutically acceptable salt thereof.

Still further object of the present invention is to provide a method for using said pyrazolopyridine compound as aforesaid therapeutic use, which comprises administering said pyrazolopyridine compound to human being or animals.

The novel pyrazolopyridine compound of the present invention can be shown by the following formula (I).

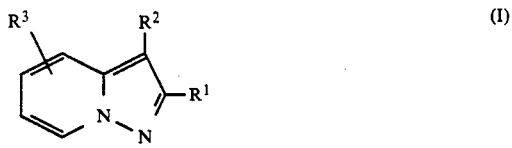

wherein
$R^1$ is lower alkyl, aryl which may have one or more suitable substituent(s) or a heterocyclic group,
$R^2$ is a group of the formula:

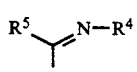

(wherein
$R^4$ is protected amino or hydroxy and
$R^5$ is hydrogen or lower alkyl);
cyano;
a group of the formula :

(wherein
$R^6$ is an acyl group, and
A is lower aliphatic hydrocarbon group which may have one or more suitable substituent(s));
amidated carboxy;
amino or protected amino; and
$R^3$ is hydrogen, lower alkyl, lower alkoxy or halogen.

The object compound (I) or a salt thereof of the present invention can be prepared by the following reaction scheme.

Process 1

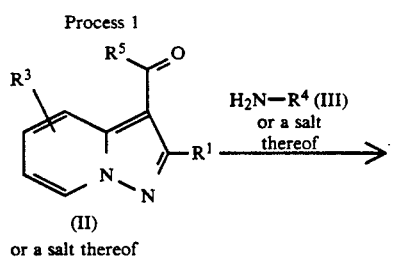

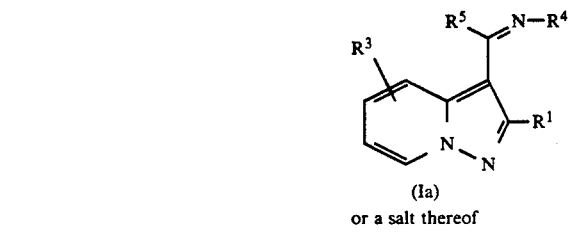

Process 2

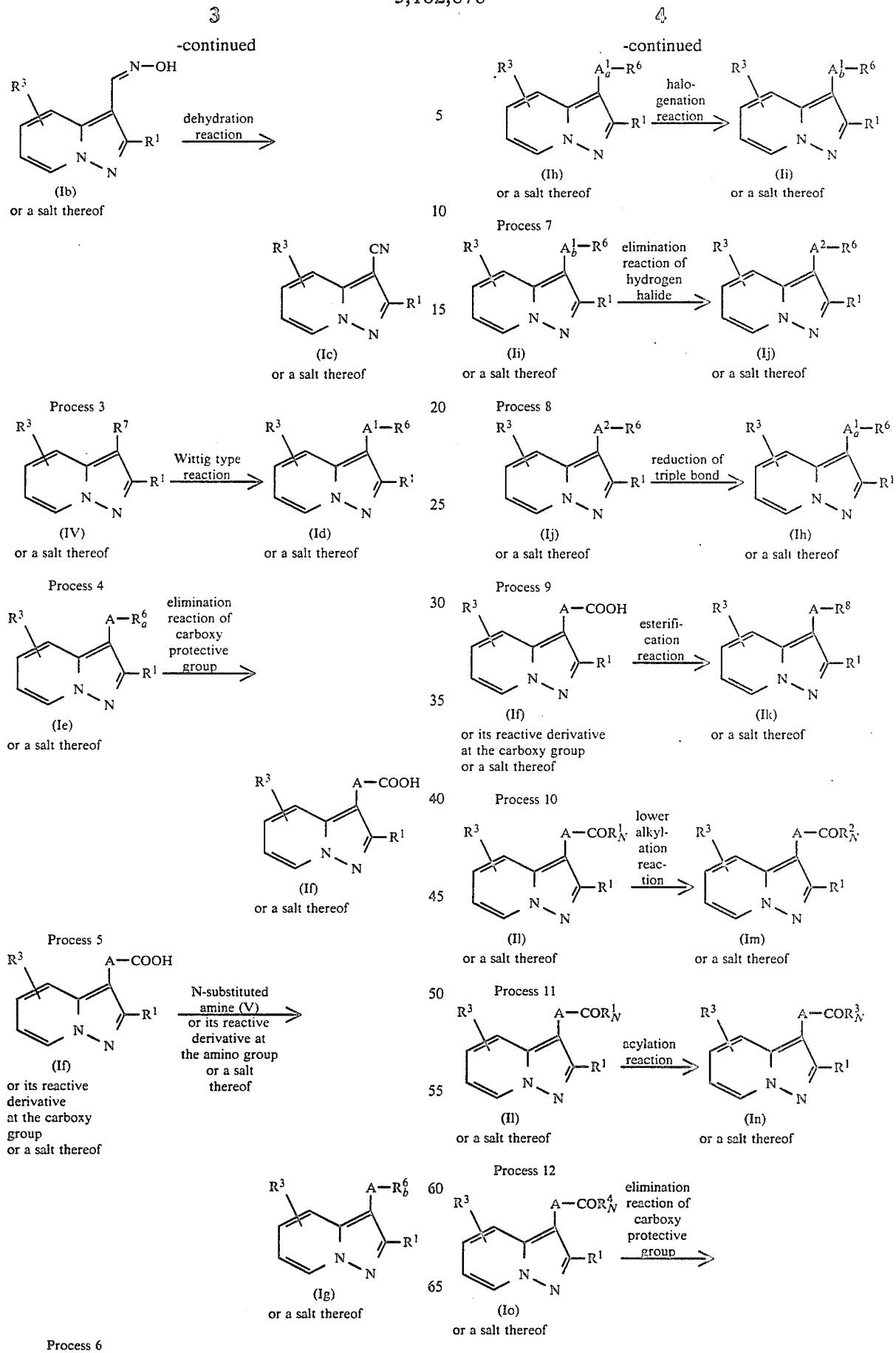

-continued

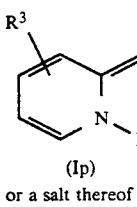

(Ip) or a salt thereof

Process 13

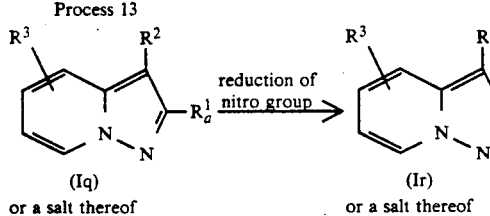

(Iq) or a salt thereof → reduction of nitro group → (Ir) or a salt thereof

Process 14

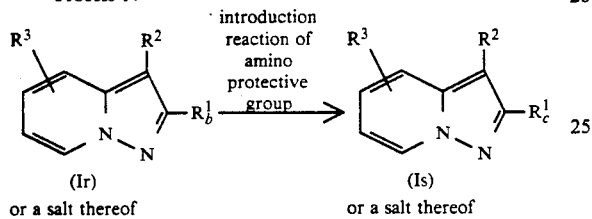

(Ir) or a salt thereof → introduction reaction of amino protective group → (Is) or a salt thereof Process 15

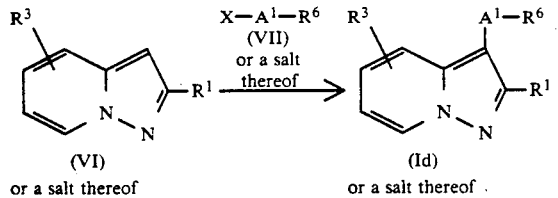

(VI) or a salt thereof + X—A¹—R⁶ (VII) or a salt thereof → (Id) or a salt thereof Process 16

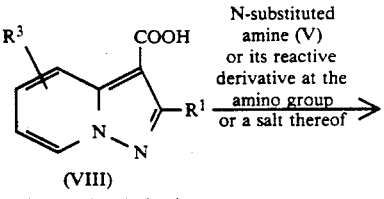

(VIII) or its reactive derivative at the carboxy group or a salt thereof + N-substituted amine (V) or its reactive derivative at the amino group or a salt thereof →

(It) or a salt thereof

Process 17

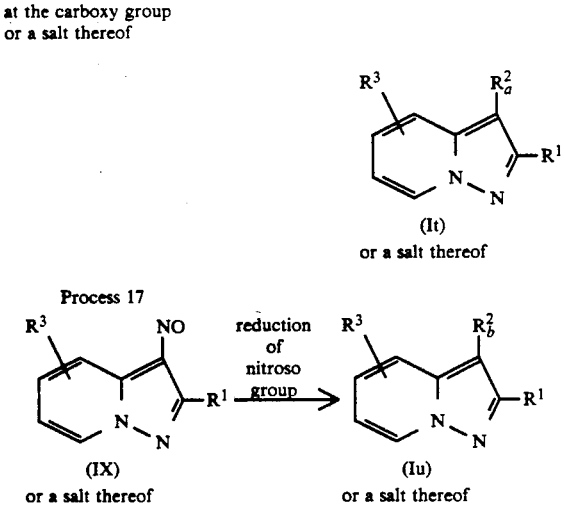

(IX) or a salt thereof → reduction of nitroso group → (Iu) or a salt thereof

Process 18

-continued

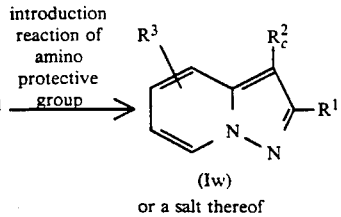

(Iv) or a salt thereof → introduction reaction of amino protective group → (Iw) or a salt thereof wherein R¹, R², R³, R⁴, R⁵, R⁶ and A are each as defined above, $R_a^1$ is aryl having nitro,
$R_b^1$ is aryl having amino,
$R_c^1$ is aryl having protected amino,
$R_a^2$ is amidated carboxy,
$R_b^2$ is amino or protected amino,
$R_c^2$ is protected amino,
$R_a^6$ is protected carboxy,
$R_b^6$ is amidated carboxy,
$R^7$ is lower alkanoyl,
$R^8$ is esterified carboxy,
$R_N^1$ is N-containing heterocyclic group having hydroxy(lower)alkyl,
$R_N^2$ is N-containing heterocyclic group having lower alkoxy(lower)alkyl,
$R_N^3$ is N-containing heterocyclic group having acyloxy(lower)alkyl,
$R_N^4$ is N-containing heterocyclic group having protected carboxy,
$R_N^5$ is N-containing heterocyclic group having carboxy,
$A^1$ is lower alkenyl which may have one or more suitable substituent(s),
$A_a^1$ is lower alkenyl,
$A_b^1$ is lower alkenyl having halogen,
$A^2$ is lower alkynyl, and
X is a leaving group.

Regarding the starting compounds, some of the compounds (IV) and (IX) are novel and they can be prepared according to the processes disclosed in Preparations 1 and 2 described later or similar manners thereto.

Suitable pharmaceutically acceptable salts of the object compound (I) are conventional ones and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, trifluoroacetate, maleate, tartrate, fumalate, methanesulfonate, benzenesulfonate, formate, toluenesulfonate, etc.), an inorganic acid salt (e.g. hydrochloride, ydrobromide, hydriodide, sulfate, phosphate, etc.), a salt with an amino acid (e.g. arginine, aspartic acid, glutamic acid, etc.), and the like.

In the above and following descriptions of the present specification, suitable examples and illustrations of the various definitions which the present invention includes within the scope thereof are explained in detail as follows.

The term "lower" is intended to mean 1 to 6 carbon atom(s) unless otherwise indicated.

The term "higher" is intended to mean 7 to 20 carbon atoms unless otherwise indicated.

Suitable "lower aliphatic hydrocarbon group" may include lower alkyl, lower alkenyl, lower alkynyl as explained below and the like.

Suitable "lower alkyl" may include straight or branched ones such as methyl, ethyl, propyl, isopropyl, butyl, t-butyl, pentyl, hexyl or the like, in which the preferred one may be (C )alkyl and the more preferred one may be methyl, ethyl, propyl and isopropyl.

Suitable "lower alkenyl" may include straight or branched ones such as vinyl, 1-methylvinyl, 2-methylvinyl, 1-propenyl, 2-propenyl, 1-butenyl, 2-methyl-1-propenyl, 1,3-butadienyl, 1-pentenyl, 4-pentenyl, -hexenyl, 1,4-hexadienyl, 5-hexenyl or the like, in which the preferred one may be (C )alkenyl and the more preferred one may be vinyl, 1-methylvinyl, 2-methylvinyl and 1,3-butadienyl.

Suitable "lower alkynyl" may include straight or branched ones such as ethynyl, 1-propynyl, 1-methylethynyl, 2-butynyl, 2-methyl-3-butynyl, 2-pentynyl, -hexynyl or the like, in which the preferred one may be (C )alkynyl and the more preferred one may be ethynyl.

Aforesaid "lower aliphatic hydrocarbon group" may have one or more (preferably one to three) suitable substituent(s) such as halogen (e.g. chloro, bromo, fluoro, iodo) or the like.

Suitable "protected amino" may include amino substituted with the conventional amino protective group such as lower alkylamino (e.g. methylamino, ethylamino, propylamino, butylamino, t-butylamino, pentylamino, hexylamino, etc.), di(lower)alkylamino (e.g. dimethylamino, diethylamino, N-ethylpropylamino, dibutylamino, N-(t-butyl)pentylamino, dihexylamino, etc.), acylamino explained below or the like.

Suitable "acylamino" may include ureido; lower alkanoylamino (e.g. formylamino, acetylamino, propionylamino, butyrylamino, isobutyrylamino, pivaloylamino, hexanoylamino, etc.), lower alkoxycarbonylamino (e.g. methoxycarbonylamino, ethoxycarbonylamino, propoxycarbonylamino, t-butoxycarbonylamino, pentyloxycarbonylamino, hexyloxycarbonylamino, etc.), lower alkoxycarbonyl(lower)alkanoylamino (e.g. methoxycarbonylacetylamino, ethoxycarbonylacetylamino, 2-(propoxycarbonyl)propionylamino, 4-(t-butoxycarbonyl)butyrylamino, 2-(butoxycarbonylmethyl)propionylamino, 2-methyl-2-(pentyloxycarbonylmethyl)propionylamino, 6-hexyloxycarbonylhexanoylamino, etc.), lower alkanesulfonylamino (e.g. methanesulfonylamino, ethanesulfonylamino, propanesulfonylamino, butanesulfonylamino, t-butanesulfonylamino, pentanesulfonylamino, hexanesulfonylamino, etc.) and the like.

Said "lower alkanoylamino" may have suitable substituent(s) such as di(lower)alkylamino (e.g. dimethylamino, N-methyl-N-ethylamino, dipropylamino, di-t-butylamino, N-pentyl-N-hexylamino, etc.); cyclic amino group (e.g. piperidino, etc.) which may have lower alkyl; or the like, and suitable examples of said "lower alkanoylamino having suitable substituent(s)" may include lower alkanoylamino having di(lower)alkylamino [e.g. dimethylaminocarbonylamino, 2-dimethylaminoacetylamino, 2-(N-methyl-N-ethylamino)acetylamino, 2-dimethylaminopropionylamino, 3-dipropylaminobutyrylamino, 2-(di-t-butylamino)-2-methylpropionylamino, 2-dimethylaminomethyl-2-methylpropionylamino, 6-(N-pentyl-N-hexylamino)hexanoylamino, etc.];

lower alkanoylamino having cyclic amino group which may have lower alkyl [e.g. piperidinocarbonylamino, 2-piperidinoacetylamino, 2-(2-methylpiperidino)acetylamino, 2-(2-ethylpiperidino)acetylamino, 2-piperidinopropionylamino, 3-(2-ethylpiperidino)butyrylamino, 2-(4-ethylpiperidino-2-methylpropionylamino, 2-piperidinomethyl-2-methylpropionylamino, 6-(3-propylpiperidino)hexanoylamino, etc.]; and the like.

In aforesaid "acylamino", the preferred one may be ureido, $(C_1-C_4)$alkanoylamino, $(C_1-C_4)$alkoxycarbonyl$(C_1-C_4)$alkanoylamino, di$(C_1-C_4)$alkylamino$(C_1-C_4)$alkanoylamino, $(C_1-C_4)$alkylpiperidino$(C_1-C_4)$alkanoylamino, $(C_1-C_4)$alkoxycarbonylamino, $(C_1-C_4)$alkanesulfonylamino, $(C_1-C_4)$-alkylamino and di$(C_1-C_4)$alkylamino, in which the more preferred one may be ureido, acetylamino,2-(ethoxycarbonyl)acetylamino, 2-dimethylaminoacetylamino, 2-(2-ethylpiperidino)acetylamino, methoxycarbonylamino, methanesulfonylamino, methylamino and dimethylamino.

Suitable "an acyl group" may include lower alkanoyl (e g. formyl, acetyl, propionyl, butyryl, isobutyryl, pivaloyl, hexanoyl, etc.); carboxy; protected carboxy; and the like.

Suitable examples of aforesaid "protected carboxy" may be esterified carboxy, in which suitable esterified carboxy may include lower alkoxycarbonyl (e.g. methoxycarbonyl, ethoxycarbonyl, propoxycarbonyl, butoxycarbonyl, t-butoxycarbonyl, pentyloxycarbonyl, hexyloxycarbonyl, etc.) which may have N-containing heterocyclic group as explained below and the like;

amidated carboxy, in which suitable amidated carboxy may include N-(lower)alkylcarbamoyl (e.g. N-methylcarbamoyl, N-ethylcarbamoyl, N-isopropylcarbamoyl, N-butylcarbamoyl, N-pentylcarbamoyl, N-hexylcarbamoyl, etc.);

N-(higher)alkylcarbamoyl (e.g. N-heptylcarbamoyl, N-(2-methylheptyl)carbamoyl, N-nonylcarbamoyl, N-decanylcarbamoyl, N-tricyclo[3.3.1.1$^{3,7}$]-decanylcarbamoyl, N-undecanylcarbamoyl, N-(bicyclo[4.3.2]-undecanyl)carbamoyl, N-dodecanylcarbamoyl, N-tridecanylcarbamoyl, N-tetradecanylcarbamoyl, N-pentadecanylcarbamoyl, N-hexadecanylcarbamoyl, N-heptadecanylcarbamoyl, N-octadecanylcarbamoyl, N-nonadecanylcarbamoyl, N-icosanylcarbamoyl, etc.);

N,N-di(lower)alkylcarbamoyl [e.g. N,N-dimethylcarbamoyl, N,N-diethylcarbamoyl, N-methyl-N-ethylcarbamoyl, N,N-dipropylcarbamoyl, N,N-di(t-butyl)-carbamoyl, N-pentyl-N-hexylcarbamoyl, etc.];

N-lower alkyl-N-ar(lower)alkylcarbamoyl (e.g. N-methyl-N-benzylcarbamoyl, etc.); a group of the formula:

$$-COR_N$$

(wherein $R_N$ is N-containing heterocyclic group which may have one or more suitable substituent(s), in which N-containing heterocyclic group $R_N$ may contain the other hetero atom(s) such as N, O or S in its ring.

Suitable "N-containing heterocyclic group" may include saturated or unsaturated, monocyclic or polycyclic heterocyclic group such as unsaturated 3 to 8-membered(more preferably 5 to 7-membered)heteromonocyclic group containing 1 to 4 nitrogen atom(s), for example, azepinyl (e.g. 1H-azepinyl, etc.) pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl-, 2H-1,2,3- triazolyl,etc.), tetrazolyl (e.g. 1H-tetrazolyl, 2H-tetrazolyl, etc.) etc.;

saturated 3 to 8-membered(more preferably 5 to 7 membered)heteromonocyclic group containing 1 to 4 nitrogen atom(s), for example, perhydroazepinyl (e.g. perhydro-1H-azepinyl, etc.) pyrrolidinyl, imidazolidinyl, piperidino, piperazinyl, etc.;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;

saturated condensed heterocyclic group containing 1 to 4 nitrogen atom(s), for example, 7-azabicyclo[2.2.1]-heptyl, 3-azabicyclo[3.2.2]nonanyl, etc.;

unsaturated 3 to 8-membered(more preferably 5 or 6-membered)heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.), etc.;

saturated 3 to 8-membered(more preferably 5 or 6-membered)heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered(more preferably 5 or 6-membered)heteromcnocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated condensed heterocyclic group containing 1 to 2 sulfur atom(s) and 1 to 3 nitrogen atom(s), for example, benzothiazolyl, benzothiadiazolyl, etc.; in which the preferred one may include saturated 3 to 8 membered heteromonocyclic group containing 1 to 4 nitrogen atom(s), saturated condensed heterocyclic group containing 1 to 4 nitrogen atom(s), and saturated 3 to 8 membered heteromonocyclic group containing 1 to 2 oxygen atom(s) and 1 to 3 nitrogen atom(s).

"N-containing heterocyclic group" thus defined may have one or more suitable substituent(s) such as lower alkyl as mentioned above; hydroxy(lower)alkyl (e.g. hydroxymethyl, 1-hydroxyethyl, 2-hydroxyethyl, 3-hydroxypropyl, 2-hydroxybutyl, 1-methyl-1-hydroxymethylethyl, 4-hydroxypentyl, 3-hydroxyhexyl, etc.); lower alkoxy(lower)alkyl (e.g. methoxymethyl, 2-methoxyethyl, 1-ethoxyethyl, 3-propoxypropyl, 2-(t-butoxy)butyl, 5-pentyloxypentyl, 3-hexyloxyhexyl, etc.); acyloxy(lower)alkyl such as lower alkanoyloxy(-lower)alkyl (e.g. acetoxymethyl, 1-acetoxyethyl, 2-acetoxyethyl, 2-propionyloxyethyl, 3-propionyloxypropyl, 2-butyryloxybutyl, 4-pivaloyloxypentyl, 6-hexanoyloxyhexyl, etc.) or the like; protected carboxy such as lower alkoxycarbonyl as mentioned above; carboxy; or the like.

In aforesaid "N-containing heterocyclic group which may have one or more suitable substituent(s)", the more preferred one may include piperidino which may have 1 to 4 suitable substituent(s) selected from a group consisting of $(C_1-C_4)$alkyl, hydroxy$(C_1-C_4)$alkyl, $(C_1-C_4)$alkoxy$(C_1-C_4)$alkanoyloxy$(C_1-C_4)$alkyl, $(C_1-C_4)$alkoxycarbonyl and carboxy (e.g. piperidino, 2-methylpiperidino, 2-ethylpiperidino, 3-ethylpiperidino, 4-ethylpiperidino, 2-propylpiperidino, 4-isopropylpiperidino, 2-butylpiperidino, 3-(t-butyl)piperidino, 4-pentylpiperidino, 2-hexylpiperidino, 2,2,6,6-tetramethylpiperidino, 2,2-dimethyl-6,6-diethylpiperidino, -hydroxymethylpiperidino, 3-hydroxymethylpiperidino, -(1-hydroxyethyl)piperidino, 2-(2-hydroxyethyl)-piperidino, -(2-hydroxyethyl)piperidino, 4-(2-hydroxyethyl)piperadino, 2-(3-hydroxypropyl)piperidino, 3-(2-hydroxybutyl)piperidino, 2-(1-methyl-1-hydroxymethylethyl)piperidino, 4-(4-hydroxypentyl)piperidino, 2-(3-hydroxyhexyl)piperidino, 2-methoxymethylpiperidino, 2-(2-methoxyethyl)piperidino, 2-(1-ethoxyethyl)piperidino, 3-(3-propoxypropyl)piperidino, 4-{2-(t-butoxy)butyl}piperidino, 2-(5-pentyloxypentyl)-piperidino, 3-(3-hexyloxyhexyl)piperidino, 2-acetoxymethylpiperidino, -(1-acetoxyethyl)piperidino, 2-(2-acetoxyethyl)piperidino, 3-(2-propionyloxyethyl)-piperidino, 4-(3-propionyloxypropyl)piperidino, 2-(2-butyryloxybutyl)piperidino, 3-(4-pivaloyloxypentyl)-piperidino, 2-(6-hexanoyloxyhexyl)piperidino, 2-methoxycarbonylpiperidino, 2-ethoxycarbonyl-piperidino, 2-propoxycarbonylpiperidino, 3-butoxycarbonylpiperidino, 4-(t-butoxycarbonyl)piperadino, 2-pentyloxycarbonylpiperidino, 2-hexyloxycarbonyl-piperidino, 2-carboxypiperidino, 3-carboxypiperidino, 4-carboxypiperidino, 2-(2-hydroxyethyl)-3-methyl-piperidino, 2-(2-hydroxyethyl)-4-carboxypiperidino, etc.);

pyrrolidin-1-yl which may have $(C_1-C_4)$alkoxy-$(C_1-C_4)$alkyl (e.g. pyrrolidin-1-yl, 2-methoxymethyl-pyrrolidin-1-yl, 2-(2-methoxyethyl)pyrrolidin-1-yl, 2-(1-ethoxyethyl)pyrrolidin-1-yl, 3-(3-propoxypropyl)pyrrolidin-1-yl, 3-{2-(t-butoxy)butyl}pyrrolidin-1-yl, 2-(5-pentyloxypentyl)pyrrolidin 1-yl, 2-(3-hexyloxyhexyl)-pyrrolidin-1-yl, etc.);

perhydroazepin-1-yl (e.g. perhydro-1H-azepin-1-yl, etc.);

piperazin-1-yl which may have $(C_1-C_4)$alkyl (e.g. piperazin-1-yl, 2-methylpiperazin-1-yl, 3-methylpiperazin-1-yl, 4-methylpiperazin-1-yl, 2-ethylpiperazin-1-yl, 3-propylpiperazin-1-yl, 4-isopropylpiperazin-1-yl, 4-penylpiperazin-1-yl, 3-(t-butyl)piperazin-1-yl, 4-penyl-piperazin-1-yl, 4-hexylpiperazin-1-yl, etc.); morpholino; 7-azabicyclo[2.2.1]heptan-7-yl; 3-azabicyclo[3.2.2]nonan-3-yl; and the like, and the most preferred one may include piperidino, 2-methylpiperidino, 2-ethyl-piperidino, 3-ethylpiperidino, 4-ethylpiperidino, 2-propylpiperidino, 2,2,6,6-tetramethylpiperidino, 2-hydroxymethylpiperidino, 2-(2-hydroxyethyl)-piperidino, 4-(2-hydroxyethyl)piperidino, 2-methoxymethylpiperidino, 2-(2-methoxyethyl)piperidino, 2-acetoxymethylpiperidino, 2-(2-acetoxyethyl)piperidino, 2-ethoxycarbonylpiperidino, 2-carboxypiperidino, pyrrolidin-1-yl, 2-methoxymethylpyrrolidin-1yl, perhydro-1H-azepin-1-yl, 4-methylpiperazin-1-yl, morphoino, 7-azabicyclo[2.2.1]heptan-7-yl, 3-azabicyclo[3.2.2]nonan-3-yl, and the like.

Suitable "N-substituted amine" may include lower alkylamine (e.g. methylamine, ethylamine, isopropylamine, butylamine, pentylamine, hexylamine, etc.);

higher alkylamine (e.g. heptylamine, 2-methylheptylamine, nonylamine, decanylamine, tricyclo[3.3.1.1$^{3,7}$]decanylamine, undecanylamine, bicyclo[4.3.2]undecanylamine, dodecanylamine, tridecanylamine, tetradecanylamine, pentadecanylamine, hexadecanylamine, heptadecanylamine, octadecanylamine, nonadecanylamine, icosanylamine, etc.);

di(lower)alkylamine [e.g. dimethylamine, diethylamine, N-methylethylamine, dipropylamine, di(t-butyl)amine, N-pentylhexylamine, etc.];

N-lower alkyl-ar(lower)alkylamine (e.g. N-methylbeznylamine, etc.); a compound of the formula:

$$H-R_N$$

(wherein $R_N$ is as defined above)

Suitable "aryl" may include phenyl, naphthyl, indenyl, anthryl and the like and said "aryl" may have one or more suitable substituent(s) such as halogen (e.g. fluoro, chloro, bromo, iodo), lower alkoxy (e.g. methoxy, ethoxy, propoxy, t-butoxy, pentyloxy, hexyloxy, etc.), nitro, amino, protected amino as mentioned before or the like.

The preferred examples of "aryl which may have one or more suitable substituent(s)" may include phenyl which may have 1 to 3 suitable substituent(s) selected from a group consisting of halogen, $(C_1-C_4)$alkoxy, nitro, amino, $(C_1-C_4)$alkanoylamino, $(C_1-C_4)$alkoxycarbonylamino, $(C_1-C_4)$alkanesulfonylamino, $(C_1-C_4)$alkylamino and di$(C_1-C_4)$alkylamino, in which the more preferred one may be phenyl, phenyl having chloro, phenyl having methoxy, phenyl having nitro, phenyl having amino, phenyl having acetylamino, phenyl having methoxycarbonylamino, phenyl having methanesulfonylamino, phenyl having methylamino and phenyl having dimethylamino.

Suitable "a heterocyclic group" may include the ones as exemplified for "N-containing heterocyclic group" as mentioned above, unsaturated 3 to 8membered (more preferably 5 or 6-membered) heteromonocyclic group containing an oxygen atom, for example, furyl, etc.;

unsaturated 3 to 8-membered (more preferably 5 or 6membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like, in which the preferred one may be unsaturated 3 to 8 membered heteromonocyclic group containing 1 to 4 nitrogen atom(s), the more preferred one may be pyridyl and the most preferred one may be 2-pyridyl, 3-pyridyl and 4-pyridyl.

Suitable "lower alkenyl having halogen" may include 1-fluorovinyl, 1-bromovinyl, 1-chloro-2-methylvinyl, 1-bromo-1-propenyl, 2-chloro-2-propenyl, 1-iodo-1-butenyl, 1-bromo-2-methyl-1-propenyl, 3-bromo-1,3-butadienyl, 1-chloro-1-pentenyl, 4-chloro-4-pentenyl, 1-bromo-1-hexenyl and the like.

Suitable "lower alkoxy" may include methoxy, ethoxy, propoxy, isopropoxy, butoxy, t-butoxy, penyloxy, hexyloxy and the like.

Suitable "halogen" may include fluoro, chloro, bromo and iodo.

Suitable "a leaving group" may include di(lower)alkylamino (e.g. dimethylamino diethylamino, N-ethylpropylamino, dibutylamino, N-pentylhexylamino, etc.), lower alkoxy as mentioned above, halogen as mentioned above, lower alkylthio (e.g. methylthio, ethylthio, propylthio, butylthio, pentylthio, hexylthio, etc.) and the like.

The processes for preparing the object compound (I) of the present invention are explained in detail in the following.

Process 1

The object compound (Ia) or a salt thereof can be prepared by reacting the compound (II) or a salt thereof with the compound (III) or a salt thereof.

Suitable salts of the compound (Ia), (II) and (III) can be referred to acid addition salts as exemplified for the compound (I).

This reaction is usually carried out in a conventional solvent such as alcohol (e.g. methanol, ethanol) or any other solvent which does not adversely influence the reaction.

This reaction is usually carried out under slightly acidic condition.

The reaction temperature is not critical and the reaction can be carried out under warming to heating.

Process 2

The object compound (Ic) or a salt thereof can be prepared by subjecting the compound (Ib) or a salt thereof to dehydration reaction.

Suitable salts of the compounds (Ib) and (Ic) can be referred to acid addition salts as exemplified for the compound (I).

The dehydration reaction of this process can be carried out according to a conventional manner and can be also carried out by reacting the compound (Ib) or a salt thereof with lower alkyl isocyanate (e.g. methyl isocyanate, etc.) in a conventional solvent (e.g. methylene chloride, chloroform, etc.) under cooling, at room temperature or under warming.

Process 3

The object compound (Id) or a salt thereof can be prepared subjecting the compound (IV) or a salt thereof to so-called Wittig type reaction.

Suitable salt of the compound (Id) can be referred to the ones as exemplified for the compound (I).

Suitable salt of the compound (IV) can be referred to acid addition salt as exemplified for the compound (I).

The reaction of this process can be carried out by reacting the compound (IV) or a salt thereof with a so-called Wittig reagent as shown in the following formulae:

$$(R^9)_3-P=A^3-R^6 \qquad (X)$$

$$(R^{10}O)_2\overset{O}{\overset{\|}{P}}-A^4-R^6 \qquad (XI)$$

[wherein
$R^9$ is aryl or lower alkyl, each as mentioned above,
$R^{10}$ is lower alkyl as mentioned above,
$R^6$ is as defined above,
$A^3$ is lower alkylidene (e.g. methylene, ethylidene, propylidene, 1-methylethylidene, butylidene, 2-methylpropylidene, pentylidene, etc.) or lower alkenylidene (e.g. vinylidene, 2-propenylidene, 2-butenylidene, 4-pentenylidene, etc.), and A⁴ is lower alkyl or lower alkenyl, each as mentioned above].

The aforesaid Wittig reagents (X) and (XI) can be prepared according to a usual manner.

The reaction of this process can be carried out in the presence of base such as alkali metal hydride (e.g. sodium hydride, potassium hydride, etc.), alkali metal lower alkoxide (e.g. potassium t-butoxide, etc.) or the like in case of using Wittig reagent (XI).

The reaction is usually carried out in a conventional solvent such as diethyl ether, tetrahydrofuran, methylene chloride, benzene, toluene, N,N-dimethylformamide or any other solvent which does not adversely influence the reaction.

The reaction temperature is not critical and the reaction can be carried out under cooling, at room temperature, under warming or under heating.

The reaction condition can be determined according to the kind of the compound (IV) and the Wittig reagent to be used.

Process 4

The object compound (If) or a salt thereof can be prepared by subjecting the compound (Ie) or a salt thereof to elimination reaction of carboxy protective group.

Suitable salts of the compounds (Ie) and (If) can be referred to the ones as exemplified for the compound (I).

This reaction is carried out in accordance with a conventional method such as hydrolysis, or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]-undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such a trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent.

The reaction temperature is not critical and the reaction is usually carried out under cooling to heating.

Process 5

The object compound (Ig) or a salt thereof can be prepared by reacting the compound (If) or its reactive derivative at the carboxy group or a salt thereof with N-substituted amine (V) or its reactive derivative at the amino group or a salt thereof.

Suitable salts of the compounds (If) and (Ig) can be referred to the ones as exemplified for the compound (I).

Suitable salt of N-substituted amine (V) can be referred to the ones as exemplified for the compound (I).

Suitable reactive derivative at the carboxy group of the compound (If) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole, tetrazole or 1-hydroxy-1H-benzotriazole; or an activated ester [e.g. cyanomethyl ester, methoxymethyl ester, dimethyliminomethyl [(CH₃)₂N=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester carboxymethyl thioester, pyranyl ester, pyridyl ester, piperidyl ester, 8-quinolyl thioester, etc.] or an ester with a N-hydroxy compound [.e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (If) to be used.

Suitable reactive derivative at the amino group of N-substituted amine (V) may include Schiff's base type imino or its tautomeric enamine type isomer formed by the reaction of N-substituted amine (V) with a carbonyl compound such as aldehyde, ketone or the like; a silyl derivative formed by the reaction of N-substituted amine (V) with a silyl compound such as bis(trimethylsilyl)acetamide, mono(trimethylsilyl)acetamide, bis(trimethylsilyl)urea or the like; a derivative formed by reaction of N-substituted amine (V) with phosphorus trichloride or phosgene, and the like.

The reaction is usually carried out in a conventional solvent such as water, alcohol [e.g. methanol, ethanol, etc.], acetone, dioxane, acetonitrile, chloroform, methylene chloride, ethylene.chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (If) is used in a free acid form or its salt form, the reaction is preferably carried out in the presence of a conventional condensing agent such as N,N'-dicyclohexylcarbodiimide; or the like.

The reaction may also be carried out in the presence of an inorganic or organic base such as an alkali metal carbonate, alkali metal bicarbonate, tri(lower)alkylamine (e.g. triethylamine, etc.), pyridine, N-(lower)alkylmorpholine, N,N-di(lower)alkylbenzylamine, or the like.

The reaction temperature is not critical, and the reaction is usually carried out under cooling to warming.

Process 6

The object compound (Ii) or a salt thereof can be prepared by subjecting the compound (Ih) or a salt thereof to halogenation reaction.

Suitable salts of the compounds (Ih) and (Ii) can be referred to the ones as exemplified for the compound (I).

This halogenation reaction can be carried out according to a conventional manner, for example, by reacting the compound (Ih) or a salt thereof with halogen (e.g. bromine, chlorine, etc.) in a conventional solvent such as methylene chloride, chloroform or any other solvent which does not adversely influence the reaction under cooling or at room temperature.

Process 7

The object compound (Ij) or a salt thereof can be prepared by subjecting the compound (Ii) or a salt thereof to elimination reaction of hydrogen halide.

Suitable salts of the compounds (Ii) and (Ij) can be referred to the ones as exemplified for the compound (I). This elimination reaction can be carried out according to a conventional manner, for example, by reacting the compound (Ii) or a salt thereof with a base such as alkali metal hydroxide (e.g. sodium hydroxide, potassium hydroxide, etc.), alkali metal alkoxide (e.g. sodium ethoxide, potassium t-butoxide, etc.) in a conventional solvent (e.g. chloroform, methanol, ethanol, dimethyl sulfoxide, etc.) under cooling to heating.

Process 8

The object compound (Ih) or a salt thereof can be prepared by subjecting the compound (Ij) or a salt thereof to reduction of triple bond.

The reaction of this process can be carried out according to a conventional manner to be used for reducing triple bond to double bond, for example, catalytic hydrogenation using lindler catalyst or the like.

Process 9

The object compound (Ik) or a salt thereof can be prepared by subjecting the compound (If) or its reactive derivative at the carboxy group or a salt thereof to esterification reaction.

Suitable salt of the compound (Ik) can be referred to acid addition salt as exemplified for the compound (I).

This esterification reaction can be carried out by reacting the compound (If) or its reactive derivative at the carboxy group or a salt thereof with a conventional esterification reagent such as lower alkanol (e.g. methanol, ethanol, propanol, butanol, t-butanol, pentanol, hexanol, etc.) according to a similar manner to that of Process 5.

Process 10

The object compound (Im) or a salt thereof can be prepared by subjecting the compound (Il) or a salt thereof to lower alkylation reaction.

Suitable salts of the compounds (Il) and (Im) can be referred to acid addition salts as exemplified for the compound (I).

The lower alkylation reaction of this process can be carried out by reacting the compound (Il) or a salt thereof with a conventional lower alkylating agent such as lower alkyl halide (e.g. methyl iodide, methyl chloride, ethyl bromide, propyl iodide, isopropyl chloride, butyl iodide, t-butyl chloride, pentyl bromide, hexyl iodide, etc.) or the like in a conventional solvent (e.g. tetrahydrofuran, etc.) under cooling to warming.

Process 11

The object compound (In) or a salt thereof can be prepared by subjecting the compound (I() or a salt thereof to acylation reaction.

Suitable salt of the compound (In) can be referred to acid addition salt as exemplified for the compound (I).

The acylation reaction of this process can be carried out by reacting the compound (I() or a salt thereof with a conventional acylating agent such as lower alkanoic acid (e.g. formic acid, acetic acid, propionic acid, butyric acid, isobutyric acid, pivalic acid, hexanoic acid, etc.), acid halide thereof, acid anhydride thereof or the like in a conventional solvent (e.g. pyridine, etc.) under cooling to warming.

Process 12

The object compound (Ip) or a salt thereof can be prepared by subjecting the compound (Io) or a salt thereof to elimination reaction of carboxy protective group.

Suitable salt of the compound (Io) can be referred to acid addition salt as exemplified for the compound (I).

Suitable salt of the compound (Ip) can be referred to the ones as exemplified for the compound (I).

The elimination reaction of this process can be carried out according to a similar manner to that of Process 4.

Process 13

The object compound (Ir) or a salt thereof can be prepared by subjecting the compound (Iq) or a salt thereof to reduction of nitro group.

Suitable salts of the compounds (Iq) and (Ir) can be referred to the ones as exemplified for the compound (I).

This reaction can be carried out according to a conventional manner to be used for reducing nitro group to amino group, for example, by using combination of metal or its salt (e.g. tin, stannous chloride, iron, ferrous chloride, ferrous sulfate, zinc, etc.) and acid (e.g. hydrochloric acid, sulfuric acid, acetic acid, etc.).

Process 14

The object compound (Is) or a salt thereof can be prepared by subjecting the compound (Ir) or a salt thereof to introduction reaction of amino protective group.

Suitable salts of the compounds (Ir) and (Is) can be referred to the ones as exemplified for the compound (I).

This reaction can be carried out by reacting the compound (Ir) or a salt thereof with a conventional agent for introducing amino protective group such as lower alkanoic acid, acid halide thereof and acid anhydride thereof as mentioned before; lower alkyl haloformate (e.g. methyl chloroformate, ethyl chloroformate, propyl bromoformate, isopropyl chloroformate, butyl bromoformate, t-butyl chloroformate, pentyl chloroformate, hexyl chloroformate, etc.); lower alkanesulfonyl halide (e.g. methanesulfonyl chloride, ethanesulfonyl chloride, propanesulfonyl bromide, isopropanesulfonyl chloride, butanesulfonyl bromide, t-butanesulfonyl chloride, pentanesulfonyl chloride, hexanesulfonyl chloride, etc.); lower alkyl halide as mentioned before; or the like in a conventional solvent (e.g., methylene chloride, toluene, N,N-dimethylformamide, etc.) under cooling to heating.

Process 15

The object compound (Id) or a salt thereof can be prepared by reacting the compound (VI) or a salt thereof with the compound (VII) or a salt thereof.

Suitable salts of the compound (VII) can be referred to the ones as exemplified for the compound (I). Suitable salt of the compound (VI) can be referred to acid addition salt as exemplified for the compound (I). This reaction is preferably carried out in the presence of acid such as Lewis acid [e.g. aluminum halide (e.g. aluminum chloride, etc.), boron halide (e.g. boron trifluoride, etc.)], inorganic acid (e.g. hydrochloric acid, sulfuric acid, etc.), organic acid (e.g. acetic acid, etc.) or the like.

This reaction is usually carried out in a conventional solvent such as methylene chloride, chloroform, tetrahydrofuran, N,N-dimethylformamide or any other solvent which does not adversely influence the reaction.

The reaction temperature is not critical and this reaction can be carried out under cooling, at room temperature or under warming to heating.

Process 16

The object compound (It) or a salt thereof can be prepared by reacting the compound (VIII) or its reactive derivative at the carboxy group or a salt thereof with N-substituted amine (V). or its reactive derivative at the amino group or a salt thereof.

Suitable salts of the compounds (It) and (VIII) can be referred to the ones as exemplified for the compound (I).

This reaction can be carried out according to a similar manner to that of Process 5.

Process 17

The object compound (Iu) or a salt thereof can be prepared by subjecting the compound (IX) or a salt thereof to reduction of nitroso group.

Suitable salts of the compounds (Iu) and (IX) can be referred to acid addition salts as exemplified for the compound (I).

The reduction of this process can be carried out according to a conventional manner to be used for reducing nitroso group to amino group. Said method can be referred to the ones as exemplified for reducing method of nitro group in Process 13.

In case that an organic acid such as lower alkanoic acid is used as an acid, the resultant amino group sometimes further reacts with said acid to give a corresponding protected amino group. This case is also included within the scope of the present invention.

Process 18

The object compound (Iw) or a salt thereof can be prepared by subjecting the compound (Iv) or a salt thereof to introduction reaction of amino protective group.

Suitable salts of the compounds (Iv) and (Iw) can be referred to acid addition salts as exemplified for the compound (I).

This reaction can be carried out according to a similar manner to that of Process 14.

It is to be noted the object compound (I) may include one or more stereoisomers due to asymmetric carbon atom(s) and double bond, and all of such isomers and a mixture thereof are included within the scope of the present invention.

It is further to be noted isomerization or rearrangement of the object compound (I) may occur due to the effect of the light, acid, base or the like, and the compound obtained as the result of said isomerization or rearrangement is also included within the scope of the present invention.

The object compound (I) and a salt thereof of the present invention are adenosine antagonists and possess various pharmaceutical actions such as cognitive enhancing action, cerebral vasodilating action, diuretic action, cardiotonic action, vasodilating action, the action of increasing the renal blood flow, enhanced lipolysis action, inhibited anaphylactic bronchoconstrictive action, accelerating action of the release of insulin, or the like, and so are useful as psychostimulant, analgesic, antidepressant, ameliorants of cerebral circulation, remedy for heart failure, cardiotonic agent, antihypertensive agent, remedy for renal insufficiency, diuretic, remedy for edema, antiobesity, antiasthmatic, bronchoconstrictor, remedy for apnea, remedy for gout, remedy for hyperuricemia, remedy for sudden infant death syndrome (SIDS), ameliorants of immunosuppression action of adenosine, antidiabetic agent, or the like, and further are inhibitors of platelet aggregation, so are useful as remedy for thrombosis, remedy for myocardiac infarction, remedy for obstruction, remedy for arteriosclerosis obliterans, remedy for thrombophlebitis, remedy for cerbral infarction, remedy for transient ischemic attack, remedy for angina pectoris, or the like.

In order to show this usefulness of the compound (I) of the present invention, the several pharmacological test results of the representative compound of the present invention are shown in the following.

Test 1. Vasodilative Activity

[I] Test Method

Male S.D. strain rats, weighing 200–300 g, were killed by bleeding and the thoracic aorta were removed. The helical strips (2.0×15 mm) were suspended in an organ bath filled with 25 ml of Tyrode's solution. The strips were connected to an strain gauge and the tension was measured isometrically. The bath solution was bubbled with a mixture of 95% $O_2$ and 5% $CO_2$ and was maintained at 37° C. After the resting tension was adjusted to 0.5 g, the arterial strips were contracted by $3.2 \times 10^{-8}$ M norepinephrine.

The test drug was added in the organ bath cumulatively. At the end of each test, $10^{-4}$ M of papaveine was added to the organ bath to obtain the maximum relaxation.

[II] Test Compound (2R)-1-[3-(2-Phenylpyrazolo[1,5-a]pyridin-3-yl)acryloyl]-2-(2-hydroxyethyl)piperidine (trans isomer) (The compound of Example 22)

[III] Test Result $IC_{50}$ value = $5.3 \times 10^{-7}$ (g/ml).

Test 2. Activity of Increasing the Renal Blood Flow

[I] Test Method

Adult Beagle dogs of either sex, weighting 9–15 kg, were used. Under anesthesia with pentobarbital sodium (35 mg/kg i.p.), the trachea was intubated with artificial respiration. Catheters were placed in an femoral vein for drug administration.

A short segment of left renal artery was exposed by a flank incision and cleared of adhering tissue to accommodate positioning of an electromagnetic flow probe. Renal blood flow was measured by connecting the flow probe to an flowmeter.

[II] Test Compound

The same compound that was used in Test 1.

[III] Test Result

| Dose (mg/kg) | Increasing % of Renal Blood Flow |
|---|---|
| 0.1 | +19.7 |

Test 3. Diuretic Activity

[I] Test Method

Male JCL:SD strain rats aged 6 weeks and weighing 170-206 g were used after starving for 18 hours. Immediately after oral dosing with the test drug suspended in 0.5% methylcellulose (0.5% MC), the animals were given 20 ml/kg physiological saline orally. The rats were housed by threes in a metabolism cage. The urine was collected for 3 hours. Urine volume was measured with a volumetric cylinder; and urinary uric acid, with a Determiner UA kit ® (Kyowa Medex Co., Ltd.). The tests were conducted in 3 groups of 3 animals each.

[II] Test Compound

The same compound that was used in Test 1.

[III] Test Results
Excretion of Urine and Uric Acid
(control = 100%)

| Dose (mg/kg) | Excretion of Urine (%) | Excretion of Uric Acid (%) |
|---|---|---|
| 10 | 344 | 125 |

Test 4. Antihypertensive Activity

[I] Test Method

Eleven-week old male Wistar rats were uninephrectomized under anesthesia. Deoxycorticosterone acetate (DOCA), suspended in peanut oil, was injected 30 mg/kg subcutaneously twice a week and 1% saline was substituted for the drinking water.

Animals with mean blood pressure 150-200 mmHg were used for experiment between 5 and 13 weeks after surgery.

Test compound (Dosage: 10 mg/kg) was administered orally to DOCA hypertensive rats daily for 5 days.

Blood pressure was measured at femoral artery by means of a pressure transducer and recorded as electrically integrated values of mean arterial pressure.

[II] Test Compound

The same compound that was used in Test 1.

[III] Test Result

Maximum Decrease of Blood Pressure (%)=27

Test 5. Inhibiting Activity of Platelet Aggregation

[I] Test Method

Blood was collected from the carotid artery of male Japanese White rabbits weighing 2.5-3.0 kg, and was mixed with 1/10 volume of 3.8% sodium citrate. Platelet rich plasma (PRP) was obtained after centrifuging the mixture at 150×g for 15 min. Platelet aggregation was measured with an aggregometer (Nikohkizai, NKK HEMA TRACER, Model PAT-4A). 0.24 ml of PRP containing $6.5$-$7.5 \times 10^8$ platelet/ml and 5 μl of test solution or PEG200:EtOH:H$_2$O (1:1:2) were successively added to the cuvette. The mixture was stirred for 2 min at 37° C. and 5 μl of 125 μg/ml collagen was added to induce aggregation. The test was conducted using PRP obtained from 3 different rabbits.

[II] Test Compound

The same compound that was used in Test 1.

[III] Test Result

Inhibiting Activity of Platelet Aggregation
IC$_{50}$ value = $7.9 \times 10^{-6}$ (g/ml).

Test 6. Cardiotonic Activity

[I] Test Method

Male Hartley strain guinea-pigs, weighing 500-600 g, were killed by bleeding and the heart was removed. An atrial strip was removed and suspended in an organ bath containing 50 ml of Tyrode's solution maintained at 30° C. and aerated with a gas mixture of 95% O$_2$-5% CO$_2$. The atrium was connected to a strain gauge under an initial tension of 0.4-0.6 g. After constant motility had been obtained the drug was added to the bath solution and the effect on the contractile force and beating rate were observed for 30 min. The effect was expressed as percentage values before and after dosing. 3 separate preparations were used for each concentration.

[II] Test Compound

The same compound that was used in Test 1.

[III] Test Results

| Concentration of Test compound (g/ml) | Increasing % of Contractile force | Increasing % of Heart Rate |
|---|---|---|
| $10^{-6}$ | 10.0 | −10.7 |

Test 7. Antihypertensive Activity

[I] Test Method

Eleven-week old male Wistar rats were uninephrectomized under anesthesia. Deoxycorticosterone acetate (DOCA), suspended in peanut oil, was injected 30 mg/kg subcutaneously twice a week and 1% saline was substituted for the drinking water.

Animals with mean blood pressure 150-200 mmHg were used for experiment between 5 and 13 weeks after surgery.

Test Compound (Dosage:3.2 mg/kg) was administered orally to DOCA hypertensive rats daily for 5 days.

Blood pressure was measured at femoral artery by means of a pressure transducer and recorded as electrically integrated values of mean arterial pressure.

[II] Test Compound

1-[3-(2-Phenylpyrazolo[1,5-a]pyridin-3-yl)acryloyl]2-ethylpiperidine·½fumalate (trans isomer) (the compound of Example 9)

| [III] Test Result |
|---|
| Maximum Decrease of Blood Pressure (%) |
| 32 |

Test 8. Adenosine Antaconism

[I] Test Method

Male Hartley strain guinea-pigs, weighing 500–650 g, were killed by bleeding and the hearts were removed.

An atrial strip was removed and suspended in an organ bath containing 50 ml of Tyrode's solution maintained at 27°–30° C. and aerated with a gas mixture of 95% $O_2$–5% $CO_2$. The atrium was connected to a strain gauge under an initial tension of 0.4–0.6 g. After constant motility had been obtained, the test compound and the adenosine ($1 \times 10^{-5}$ M) were added. The negative inotropic activity of the adenosine was compared in the absence or presence of the test compound and then the adenosine antagonistic activities were measured. Adenosine antagonistic activities were expressed as $IC_{50}$ values.

[II] Test Compound (2R)-1-3-(2-Phenylpyrazolo[1,5-a]pyridin-3-yl)acryloyl]-2-(2-hydroxyethyl)piperidine (trans isomer) (The compound of Example 22)

[III] Test Result $IC_{50}$ value $= 4.9 \times 10^{-10}$ (M).

For therapeutic administration, the object compound (I) and a pharmaceutically acceptable salt thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration.

The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases, a kind of the compound (I) to be applied, etc. In general, amount between 1 mg and about 1,000 mg or even more per day may be administered to a patient An average single dose of about 1 mg, 5 mg, 10 mg, 20 mg of the object compound (I) of the present invention may be used as diuretic, antihypertensive agent, remedy for renal insufficiency, remedy for thrombosis or cardiotonic agent.

The following Preparations and Examples are given for the purpose of illustrating the present invention in more detail.

EXAMPLE 1

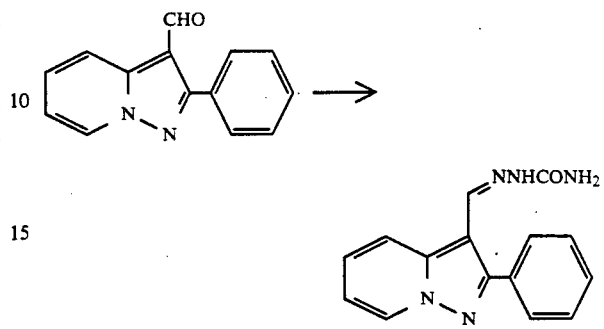

A mixture of 2-phenylpyrazolo[1,5-a]pyridine-3-carbaldehyde (0.5 g) and semicarbazide.hydrochloride (0.25 g) in ethanol (7 ml) was refluxed for 1 hour and then cooled. The resulting precipitates were filtered and recrystallized from a mixture of water and ethanol to give 2-phenylpyrazolo[1,5-a]pyridine-3-carbaldehyde semicarbons (0.26 g).

mp: 221°–222° C.

IR (Nujol): 3350, 1660, 1570 cm$^{-1}$.

NMR (DMSO-$d_6$, δ): 6.33 (2H, s), 7.00–7.90 (7H, m), 8.27 (1H, s), 8.43 (1H, dd, J=1.0, 8.0Hz), 8.85 (1H, d, J=6.5Hz), 9.97 (1H, s).

MS: 279 (M$^+$).

EXAMPLE 2

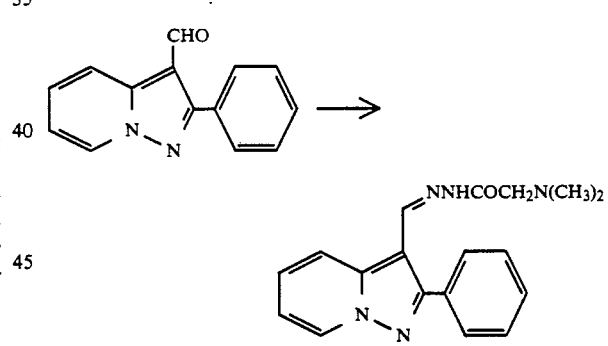

A mixture of [2-(dimethylamino)aceto]hydrazide.dichloride (624 mg) and potassium carbonate (910 mg) in ethanol (7 ml) was heated at 60° C. To the mixture 2-phenylpyrazolo[1,5-a]pyridine-3-carbaldehyde (666 mg) was added and refluxed for 2.5 hours. After being cooled, the mixture was filtered off and the filtrate was evaporated in vacuo. The residue was chromatographed on silica gel (20 g) with a mixture of chloroform and methanol (20:1) as an eluent. The fractions containing the object compound were combined and evaporated in vacuo. The residue was recrystallized from ethanol to give 2-phenylpyrazolo[1,5-a]pyridine-3-carbaldehyde [2-(dimethylamino)acetyl]hydrzone as crystals (0.63 g).

mp: 172°–173° C.

IR (Nujol): 1670, 1620 cm$^{-1}$.

NMR (CDCl$_3$, δ): 2.33 (3H, s), 3.13 (2H, s), 6.95 (1H, dt, J=2.0, 7.0Hz), 7.30–7.83 (7m), 8.37 (1H, s), 8.53 (1H, dd, J=1.0, 7.5 Hz), 9.83–10.0 (1H, m).

MS: 321 (M+).

Analysis Calcd. for $C_{18}H_{19}N_5O$. C:67.27, H:5.96, N:21,79. Found C:67.65, H:5.96, N:21.80.

EXAMPLE 3

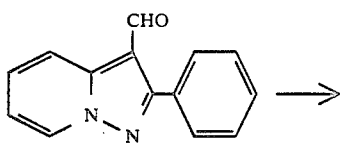

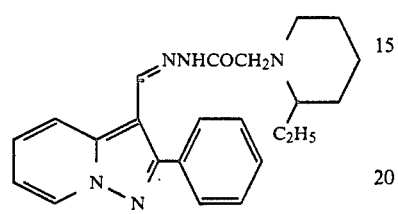

2-Phenylpyrazolo[1,5-a]pyridine-3-carbaldehyde [2-(2-ethylpiperidino)acetyl]hydrazone was obtained according to a similar manner to that of Example 2.

mp: 156°-157.5° C.

IR (Nujol): 3200, 1660, 1625, 1595, 1520 cm$^{-1}$.

NMR (CDCl$_3$, δ): 0.90 (3H, t, J=7.0Hz), 1.13-2.00 (8H, m), 2.20-2.67 (2.20-2.67 (2H, m), 2.77-3.10 (1H, m), 3.07 (1H, d, J=17.0Hz), 3.50 (1H, d, J=17.0Hz), 7.02 (1H, t, J=7.0Hz), 7.30-7.90 (6H, m), 8.43-8.73 (3H, m), 10.10 (1H, broad s).

MS: 389 (M+).

Analysis Calcd. for $C_{23}H_{27}N_5O$. C:70.93, H:6.99, N:17.98. Found C:70.88, H:6.93, N:17.98.

EXAMPLE 4

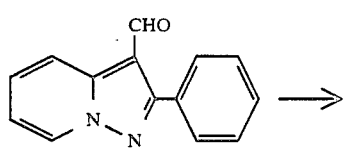

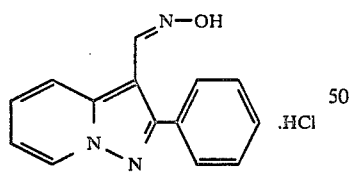

A mixture of 2-phenylpyrazolo[1,5-a]pyridine-3-carbaldehyde (0.5 g) and hydroxylamine.hydrochloride (0.17 g) in ethanol (5 ml) was refluxed for 1.5 hours and evaporated in vacuo. The residue was triturated with ethyl acetate and recrystallized from a mixture of ethanol and ethyl acetate to give 2-phenylpyrazolo[1,5-a]pyridine-3-carbaldehyde oxime.hydrochloride (0.28 g).

mp: 156-157° C.

IR (Nujol): 2380, 1620 cm$^{-1}$.

NMR (DMSO-d$_6$, δ): 7.07-8.17 (9H, m), 8.80 (1H, d J=8Hz), 10.33 (1H, s).

MS: 237 (M+).

EXAMPLE 5

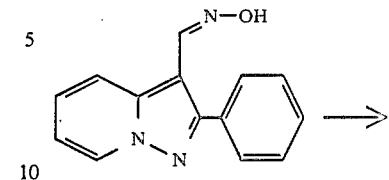

A solution of methyl isocyanate (0.19 g) in methylene chloride (2 ml) was added dropwise to a mixture of 2-phenylpyrazolo[1,5-a]pyridine-3-carbaldehyde oxime (0.52 g) in chloroform (4 ml) with stirring and ice-cooling. The mixture was stirred at room temperature for 2 hours and allowed to stand at room temperature overnight. The solvent was evaporated in vacuo and the residue was chromatographed on silica gel (20 g) with methylene chloride as an eluent. The fractions containing the object compound were combined (20 ml) and evaporated in vacuo. The residue was recrystallized from ethyl acetate to give 2-phenylpyrazolo[1,5-a]pyridine-3-carbonitrile (0.21 g).

mp: 138°-139° C.

IR (Nujol): 2220, 1620 cm$^{-1}$.

NMR (CDCl$_3$, δ): 7.03 (1H, dt, J=2.0, 7.0Hz), 7.43-7.93 (5H, m), 8.03-8.37 (2H, m), 8.58 (1H, dd, J=1.0, 7.0Hz).

MS: 219 (M+).

EXAMPLE 6

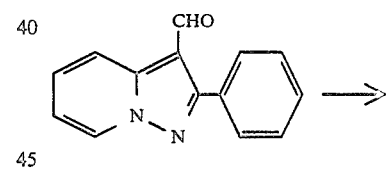

A mixture of 2-phenylpyrazolo[1,5-a]-pyridine-3-carbaldehyde (0.50 g) and acetonylidenetriphenylphosphorane

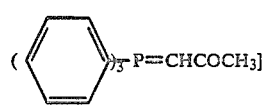

(0.82 g) in benzene (6 ml) was refluxed for 4 hours and then the solvent was evaporated in vacuo. The residue was chromatographed on silica gel (20 g) with chloroform as an eluent. The fractions containing the object compound were combined and evaporated in vacuo.

the residue was recrystallized from ethanol to give crystals of 4-(2-phenylpyrazolo[1,5-a]pyridin-3-yl)-3-buten-2-one (trans isomer) (0.21 g).

mp: 134.5°–135.5° C.

IR (Nujol): 1650, 1600, 1500 cm$^{-1}$.

NMR (CDCl$_3$, δ): 2.37 (3H, s), 6.67 (1H, d, J=16.0Hz), 7.00 (1H, dt, J=2.0, 6.0Hz), 7.10–8.07 (9H, m), 8.63 (1H, d, J=6.0Hz).

MS: 262 (M+).

Analysis Calcd for C$_{17}$H$_{14}$N$_2$O. C:77.84, H:5.38, N:10.68. Found C:78.55, H:5.40, N:10.65.

EXAMPLE 7

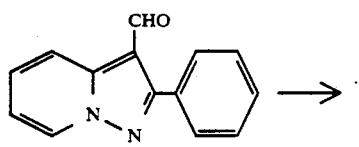

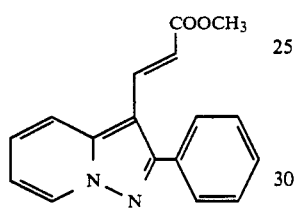

A solution of trimethyl phosphonoacetate (4.0 g) in toluene (10 ml) was added to a mixture of sodium hydride (63%, 880 mg) in toluene (45 ml) with stirring and cooling and then heated at 60° C. for 20 minutes. To the mixture 2-phenylpyrazolo[1,5-a]pyridine-3-carbaldehyde (2.0 g) was added and heated at 60°C. for 8 hours. A saturated sodium bicarbonate solution (30 ml) was added to the reaction mixture and extracted with ethyl acetate (30 ml, 2 times). The extract was washed with brine (30 ml), dried over magnesium sulfate and evaporated in vacuo. The residue was recrystallized from a mixture of ethyl acetate and isopropyl alcohol to give crystals of methyl 3-(2-phenylpyrazolo[1,5-a]pyridin-3-yl)acetate (trans isomer) (1.34 g).

mp: 139°–139.5° C.

IR (Nujol): 1700, 1610 cm$^{-1}$.

NMR (CDCl$_3$, δ): 3.77 (3H, s), 6.28 (1H, d, J=16Hz), 6.88 (1H, dt, J=1.5, 6.0Hz), 7.20–7.90 (7H, m), 7.92 (1H, d, J=16Hz), 8.50 (1H, d, J=6.0Hz).

MS: 278 (M+).

EXAMPLE 8

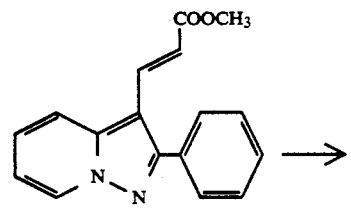

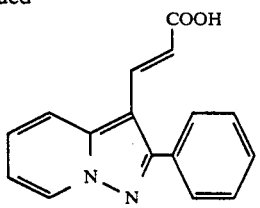

A mixture of methyl 3-(2-phenylpyrazolo[1,5-a]pyridin-3-yl)acrylate (trans isomer) (4.05 g) in 1 N sodium hydroxide solution (58.3 ml) and methanol (80 ml) was refluxed for 1 hour and evaporated in vacuo. The residue was dissolved in water and washed with chloroform. The aqueous layer was acidified with 1 N hydrochloric acid. The resulting precipitates were filtered and recrystallized from isopropyl alcohol to give crystals of 3-(2-phenylpyrazolo[1,5-a]pyridin-3-yl)acrylic acid (2.65 g).

mp: 225°–225.5° C.

IR (Nujol): 1660, 1590 cm$^{-1}$.

NMR (DMSO-d$_6$, δ): 6.32 (1H, d, J=16.0Hz), 7.15 (1H, dt, J=1.0, 6.0Hz), 7.40–7.92 (7H, m), 8.10 (1H, d, J=7.0Hz), 8.87 (1H, d, J=6.0Hz).

MS: 264 (M+).

Anlaysis Calcd for C$_{16}$H$_{12}$N$_2$O$_2$. C:72.72, H:4.58, N:10.60. Found C:73.13, H:4.50, N:10.67.

EXAMPLE 9

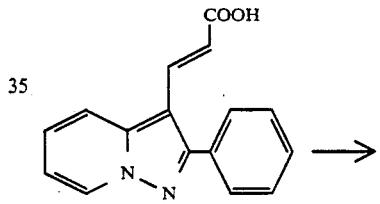

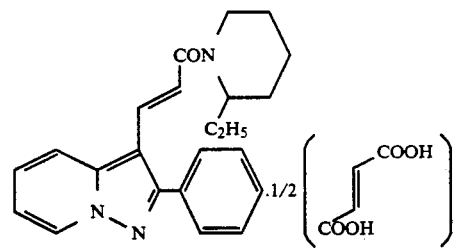

Isobutyl chloroformate (1.04 g) was added dropwise to a mixture of 3-(2-phenylpyrazolo[1,5-a]pyridin-3-yl)acrylic acid (trans isomer) (2.0 g) and triethylamine (0.766 g) in methylene chloride (40 ml) and tetrahydrofuran (10 ml) at −20° C. with stirring. After being stirred at the same temperature for 30 minutes, a solution of 2-ethylpiperidine (0.942 g) in tetrahydrofuran (10 ml) was added thereto dropwise at −20° C. and the mixture was stirred at −20° C. to 10° C. for 2 hours. The mixture was warmed to room temperature and evaporated in vacuo. A saturated sodium bicarbonate solution was added to the residue and extracted twice with chloroform (50 ml). The combined extract was washed with saturated brine (50 ml), dried over magnesium sulfate and evaporated in vacuo. The residue was chromatographed on silica gel (40 g) with chloroform as an eluent. The fraction containing the object compound were combined and evaporated in vacuo to give 1-3-(2-phenylpyrazolo[1,5-a]pyridin-3-yl)acryloyl]-2-ethylpiperidine (trans isomer) (1.30 g) as an oil.

This compound was converted to ½fumalate in a usual manner. The crystals were recrystallized from a mixture of n-hexane and diethyl ether to give yellow crystals of 1-[3-(2-phenylpyrazolo[1,5-a]pyridin-3-yl)acryloyl]-2-ethylpiperidine.½fumalate (trans isomer) (0.96 g).

mp 121°–122° C.

IR (Nujol): 1705, 1635, 1580., 1540, 1510 cm$^{-1}$.

NMR (DMSO-$d_6$, $\delta$) : 0.77 (3H, t, J=7.0Hz), 1.30–1.83 (8H, m), 6.66 (1H, s), 6.83 (1H, d, J=16.0Hz), 7.00–7.83 (8H, m), 8.07 (1H, d, J=9.0Hz), 8.77 (1H, d, J=7.0Hz).

Analysis Calcd for $C_{23}H_{25}N_3O \cdot \frac{1}{2}C_4H_4O_4$. C:71.92, H:6.52, N:10.0. Found C: 72.01, H:6.60, N:10.03.

The following compounds (Examples 10 to 17) were obtained according to a similar manner to that of Example 9.

EXAMPLE 10

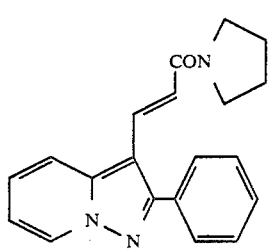

1-[3-(2-Phenylpyrazolo[1,5-a]pyridin-3-yl)acryloyl]-pyrrolidine (trans isomer)

mp: 190°–191° C.

IR (Nujol): 1640, 1590 cm$^{-1}$.

NMR (CDCl$_3$, $\delta$): 1.70–2.30 (4H, m), 3.33–3.90 (4H, m), 6.53 (1H, d, J=16.0Hz), 6.77–8.13 (8H, m), 8.57 (1H, d, J=7.0Hz)

Analysis Calcd for $C_{20}H_{19}N_3O$. C:75.69, H:6.03, N:13.24. Found C:76.08, H:5.95, N:13.16.

MS: 317 (M+).

EXAMPLE 11

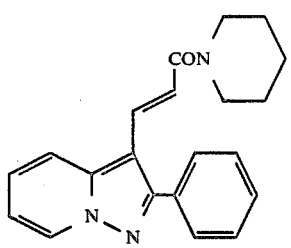

1-[3-(2-Phenylpyrazolo[1,5-a]pyridin-3-yl)acryloyl]-piperadine (trans isomer)

mp: 111.5°–112° C.

IR (Nujol): 1630, 1580 cm$^{-1}$.

NMR (CDCl$_3$, $\delta$): 1.40–1.75 (6H, m), 3.30–3.70 (4H, broad s), 6.65 (1H, d, J=15.0Hz), 6.83 (1H, dt, J=2.0, 6.0Hz), 7.13–7.80 (7H, m), 7.83 (1H, d, J=15.0Hz), 8.45 (1H, d, J=6.0Hz).

Analysis Calcd for $C_{21}H_{21}N_3O$. C:76.11, H:6.39, N:12.68. Found C: 76.08, H:6.32, N:12.65.

MS: 331 (M+).

EXAMPLE 12

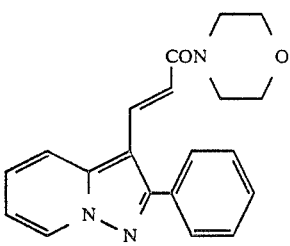

mp: 154.5°–155.5° C.

IR (Nujol): 1625, 1580 cm$^{-1}$.

NMR (CDCl$_3$, $\delta$): 3.63 (8H, m), broad s), 6.60 (1H, d, J=16.0Hz), 6.90 (1H, dt, J=2.0, 7.0Hz), 7.15–7.83 (7H, m), 8.00 (1H, d, J=16.0Hz), 8.50 (1H, dd, J=1.0, 7.0Hz).

MS: 333 (M+).

Analysis Calcd for $C_{20}H_{19}N_3O_2$. C:72.05, H:5.74, N:12.60. Found C: 72.55, H:5.72, N:12.58.

EXAMPLE 13

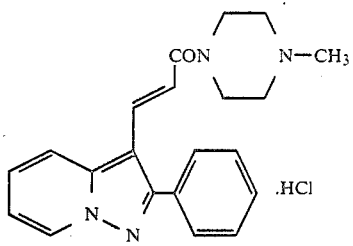

1-[3-(2-Phenylpyrazolo[1,5-a]pyridin-3-yl)acryloyl]-4-methylpiperazine.hydrochloride (trans isomer)

mp: 261°–262° C.

IR (Nujol): 2400, 1650, 1580, 1500 cm$^{-1}$.

NMR (DMSO-$d_6$, $\delta$): 2.78 (3H, s), 3.00–3.70 (8H, m), 6.99 (1H, d, J=11Hz), 7.00–7.83 (7H, m), 7.76 (1H, d, J=11Hz), 8.27 (1H, d, J=6.0Hz), 8.90 (1H, d, J=5.0Hz).

Analysis Calcd for $C_{21}H_{22}N_4O \cdot HCl$. C:65.88, H:6.05, N:14.63. Found C: 65.90, H:6.01, N:14.66.

EXAMPLE 14

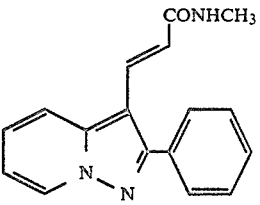

N-methyl-3-(2-phenylpyrazolo[1,5-a]pyridin-3-yl)-acrylamide (trans isomer)

mp: 208°–209° C.

IR (Nujol): 3275, 1640, 1605 cm$^{-1}$.

NMR (DMSO-$d_6$, $\delta$): 2.73 (3H, d, J=5.0Hz), 6.77 (1H, d, J=16.0Hz), 7.0–8.10 (9H, m), 8.90 (1H, d, J=6.0Hz).

MS: 277 (M+).

EXAMPLE 15

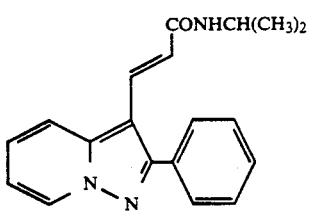

N-Isopropyl-3-(2-phenylpyrazolo[1,5-a]pyridin-3-yl)-acrylamide (trans isomer)

mp: 210°–210.5° C.
IR (Nujol): 3275, 1640, 1600 cm$^{-1}$.
NMR (CDCl$_3$, δ): 1.22 (3H, d, J=7.0Hz), 6.23 (1H, d, J=16.0Hz), 6.90 (1H, dt, J=2.0, 7.0Hz), 7.20–8.07 (8H, m), 8.53 (1H, dd, J=2.0, 7.0Hz).
Analysis Calcd for C$_{19}$H$_{19}$N$_3$O. C:74.73, H:6.27, N:13.76. Found C: 74.96, H:6.16, N:13.80.
MS: 305 (M+).

EXAMPLE 16

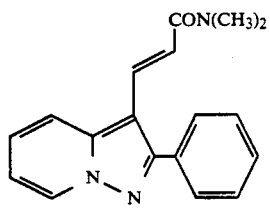

N,N-Dimethyl-3-(2-phenylpyrazolo[1,5-a]pyridin-3-yl)-acrylamide (trans isomer)

mp: 154°–155° C.
IR (Nujol): 1640, 1590 cm$^{-1}$.
NMR (CDCl$_3$, δ): 3.05 (6H, s), 6.70 (1H, d, J=2.0, 7.0Hz), 7.15–7.78 (7H, m), 7.95 (1H, d, J=16.0Hz), 8.50 (1H, dd, J=1.0, 7.0Hz).
Analysis Calcd for C$_{18}$H$_{17}$N$_3$O. C:74.21, H:5.88, N:14.42. Found C: 74.44, H:5.86, N:14.42.
MS: 291 (M+).

EXAMPLE 17

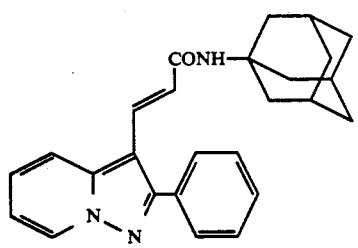

N-(Tricyclo[3.3.1.1$^{3,7}$]decan-1-yl)-3-(2-phenylpyrazolo[1,5-a]pyridin-3-yl)acrylamide (trans isomer)

mp: 232.5°–233.5° C.
IR (Nujol): 3280, 1650, 1590, 1535, 1500 cm$^{-1}$.
NMR (CDCl$_3$, δ): 1.53–1.83 (6H, m), 1.90–2.27 (9H, m), 5.23 (1H, broad s), 6.62 (1H, d, J=16.0Hz), 6.90 (1H, dt, J=1.0, 7.0Hz), 7.30 (1H, dt, J=6.0Hz), 7.43–7.97 (7H, m), 8.57 (1H, d, J=6.0Hz).
Analysis Calcd for C$_{21}$H$_{21}$N$_3$O. C:76.11, H:6.39, N:12.68. Found C: 76.08, H:6.32, N:12.65.

MS: 331 (M+).
Analysis Calcd for C$_{26}$H$_{27}$N$_3$O. C:78.56, H:6.85, N:10.57. Found C:77.85, H.7 01, N:10.30.
MS : 398 (M+).

EXAMPLE 18

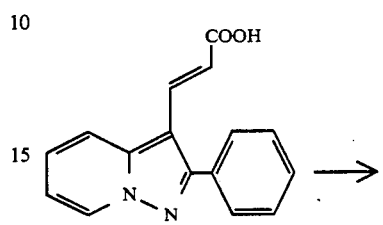

→

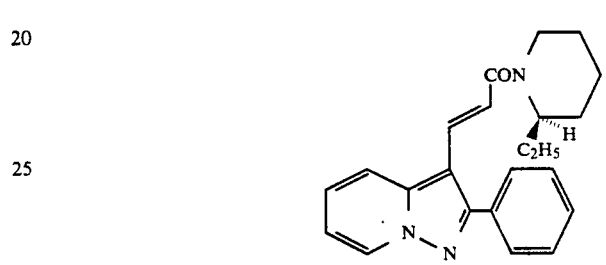

Isobutyl chloroformate (2.07 g) was added dropwise to a mixture of 3-(2-phenylpyrazolo[1,5-a]-pyridin-3-yl)acrylic acid (trans isomer)(4.0 g) and triethylamine (1.53 g) in N,N-dimethylformamide (40 ml) at −20° C. with stirring. After being stirred at the same temperature for 30 minutes, a solution of (2R)-2-ethylpiperidine (1.88 g) in N,N-dimethylformamide (20 ml) was added dropwise at −20° C. and the mixture was stirred at −20° C. to −10° C. for 2 hours.

The reaction mixture was poured into water (100 ml) and extracted twice with ethyl acetate (50 ml). The combined extracts were washed with saturated sodium chloride aqueous solution (30 ml), dried over magnesium sulfate and evaporated in vacuo.

The residue was chromatographed on silica gel (80 g) with chloroform as an eluent. The fractions containing the object compound were combined and evaporated in vacuo to give (2R)-1-[3-(2-phenylpyrazolo[1,5-a]pyridin-3-yl)acryloyl]-2-ethylpiperidine (trans isomer)(3.13 g) as an oil.

[α]$_D^{26}$ = −34.30° (c=1.0, EtOH).
IR (film): 2930, 2860, 1635, 1585 cm$^{-1}$.
NMR (CDCl$_3$, δ): 0.85 (3H, t, J=7.0Hz), 1.43–1.90 (6H, m), 2.50–3.20 (1H, m), 3.83–4.73 (2H, m), 6.70 (1H, d, J=16.0Hz), 6.88 (1H, dt, J=1.5Hz and 7.0Hz), 7.17–7.93 (7H, m), 7.97 (1H, d, J=16.0Hz), 8.54 (1H, dd, J=1.0Hz and 7.0Hz)
MS: 359 (M+).

EXAMPLE 19

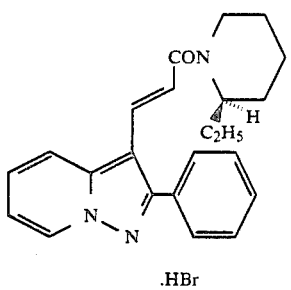

.HBr (2R)-1-[3-(2-phenylpyrazolo[1,5-a]pyridin-3-yl)acryloyl]-2-ethylpiperidine (trans isomer)(1.79 g) was converted to hydrobromic acid salt in a usual manner. The crystals were recrystallized from a mixture of ethyl acetate and acetone to give yellow crystals of (2R)-1-[3-(2-phenylpyrazolo[1,5-a]pyridin-3-yl)acryloyl]-2-ethylpiperidine.hydrobromide (trans isomer)(1.48 g).
mp: 103°-104° C.
IR (Nujol): 1630, 1600, 1500 cm$^{-1}$.
NMR (DMSO-d$_6$, δ): 0.78 (3H, t, J=7Hz), 1.18-1.87 (6H, m), 2.70-3.23 (1H, m), 4.00-3.67 (2H, m), 6.91 (1H, d, J=15.0Hz), 7.12 (1H, dt, J=2.0Hz) and 7.0Hz), 7.33-8.26 (10H, m), 8.42 (1H, s), 8.83 (1H, d, J=7.0Hz)
[α]$_D^{26.4}$ = −29.39° (c=0.966; EtOH).

EXAMPLE 20

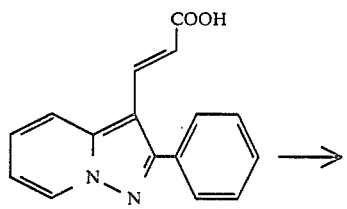

→

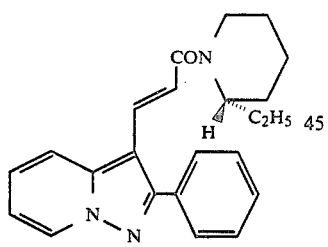

Isobutyl chloroformate (2.07 g) was added dropwise to a mixture of 3-(2-phenylpyrazolo[1,5-a]pyridin-3-yl)acrylic acid (trans isomer)(4.0 g) and triethylamine (1.53 g) in N,N-dimethylformamide (40 ml) at −20° C. with stirring. After being stirred at the same temperature for 30 minutes, a solution of (2S)-2-ethylpiperidine (1.88 g) in N,N-dimethylformamide (20 ml) was added dropwise at −20° C. and the mixture was stirred at −20° C. to −10° C. for 2 hours.

The reaction mixture was poured into water (100 ml) and extracted twice with ethyl acetate (50 ml). The combined extracts were washed with saturated sodium chloride aqueous solution (30 ml), dried over magnesium sulfate and evaporated in vacuo.

The residue was chromatographed on silica gel (80 g) with chloroform as an eluent. The fractions containing the object compound were combined and evaporated in vacuo to give (2R)-1-[3-(2-phenylpyrazolo[1,5-a]pyridin-3-yl)acryloyl]-2-ethylpiperidine (trans isomer) as an oil.
[α]$_D^{26}$ = +34.80° (c=1.0; EtOH).
IR (film): 2930, 2860, 1635, 1585 cm$^{-1}$.
NMR (CDCl$_3$, δ): 0.85 (3H, t, J=7.0Hz), 1.43-1.90 (6H, m), 2.50-3.20 (1H, m), 3.83-4.73 (2H, m), 6.70 (1H, d, J=16.0Hz), 6.88 (1H, dt, J=1.5Hz and 7.0Hz), 7.17-7.93 (7H, m), 7.97 (1H, d, J=16.0Hz), 8.54 (1H, dd, J=1.0Hz and 7.0Hz).
MS: 359 (M+).

EXAMPLE 21

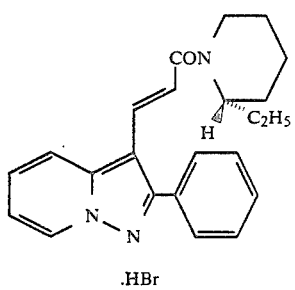

.HBr (2S)-1-3-(2-phenylpyrazolo1,5-a]pyridin-3-yl)-acryloyl]-2-ethylpiperidine (trans isomer)(2.11 g) was converted to hydrobromic acid salt in a usual manner. The crystals were recrystallized from a mixture of ethyl acetate and acetone to give yellow crystals of (2S)-1-(2-phenylpyrazolo[1,5-a]pyridin-3-yl)acryloyl]-2-ethylpiperidine.hydrobromide (trans isomer)(1.75 g).
mp : 104°-105° C.
IR (Nujol): 1630, 1600, 1500 cm$^{-1}$.
NMR (DMSO-d$_6$, δ): 0.78 (3H, t, J=7.0Hz), 1.18-1.87 (6H, m), 2.70-3.23 (1H, m), 4.00-3.67 (2H, m), 6.88 (1H, d, J=16.0Hz), 7.11 (1H, dt, J=2.0Hz and 7.0Hz), 7.36-8.28 (10H, m), 8.77 (1H, s), 8.83 (1H, d, J=7.0Hz). [α]$_D^{26.4}$ = +29.91° (c=0.926; EtOH).

EXAMPLE 22

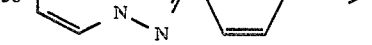

→

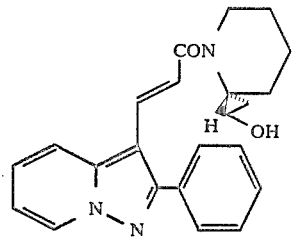

Thionyl chloride (1.79 g) was added dropwise to a stirred mixture of 3-(2-phenylpyrazolo[1,5-a]pyridin-3-yl)acrylic acid (trans isomer) (2.00 g) and N,N-dimethylformamide (4 drops) in methylene chloride (10 ml) under ice-cooling.

After being stirred at room temperature for 3 hours, the solvent was evaporated in vacuo to give acid chloride derivative.

On the other hand, (R)-2-(2-hydroxyethyl)piperidine (6.48 g) was added dropwise to bis-(trimethylsilyl-)acetamide (6.80 g) under ice-cooling. The mixture was warmed to room temperature with stirring for 20 minutes.

Triethylamine (1.53 g) and methylene chloride (40 ml) was added to the mixture. The above acid chloride derivative was added to this mixture under ice-cooling, and stirred at room temperature for 1 hour. The solvent was evaporated in vacuo and a mixture of 1 N hydrochloric acid solution (10 ml) and ethyl acetate (10 ml) was added thereto.

After the resultant mixture was stirred for 30 minutes 1 N sodium hydroxide solution (12 ml) was added to the mixture and extracted with methylene chloride (60 ml). The extract was dried over magnesium sulfate and the solvent was evaporated in vacuo. The residue was chromatographed on silica gel (40 g) with a mixture of methylene chloride and ethyl acetate (5:1) as an eluent. The fractions containing the object compound were combined and evaporated in vacuo to give (2R)-1-[3-(2-phenylpyrazolo[1,5-a]pyridin-3-yl)acryloyl]-2-(2-hydroxyethyl)piperidine (trans isomer) (1.83 g).

mp: 145°-146.5° C.
$[\alpha]_D^{24.0} = +39.61°$ (C=1 04, 95% EtOH).
IR(Nujol): 3350, 1640, 1575, 1520 cm$^{-1}$.
NMR(CDCl$_3$, δ) : 1.23~2.20 (8H, m), 2.63~3.90(4H, m), 400~4.40(1H, m), 4.67~5.10(1H, m), 6.63(1H, d, J=16.0 Hz), 8.50(1H, t, J=7.0Hz), 7.77(7H, m), 7.92(1H, d, J=16.0 Hz), 8.47(1H, d, J=7.0 Hz).

Analysis Calcd for C$_{23}$H$_{25}$N$_3$O$_2$. C 73.58, H 6.71, N 11.19. Found C 73.98, H 6.76, N 11.24.

MS 375 (M+).

The following compounds (Examples 23 and 24) were obtained according to a similar manner to that of Example 22.

EXAMPLE 23

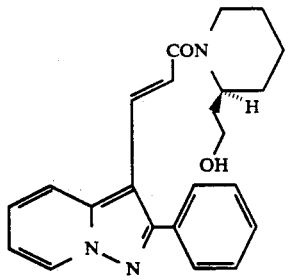

(2S)-1-[3-(2-Phenylpyrazolo[1,5-a]pyridin-3-yl)acryloyl]-2-(2-hydroxyethyl)piperidine (trans isomer)

mp: 98°~99.5 ° C. $[\alpha]_D^{23.0} = -41.20°$ (C=1.0, 95% EtOH).
IR(CHCl$_3$): 3330, 1635, 1570, 1520 cm$^{-1}$.
NMR(CDCl$_3$, δ): 1.17~2 20(8H, m), 2.67~4.00(4H, m), 2.78(1H, s}, 4.67~5.10(1H, m), 6.70(1H, d, J=16.0Hz), 6~89(1H, t, J=7.0Hz), 7.25~7.87(7H, m), 8.00(1H, d, J=16.0 Hz), 8.57(1H, d, J=7.0Hz).

Analysis Calcd for C$_{23}$H$_{25}$N$_3$O$_2$. C 73.58, H 6.71, N 11.19. Found C 73.68, H 6.81, N 11.21.

MS 375 (M+).

EXAMPLE 24

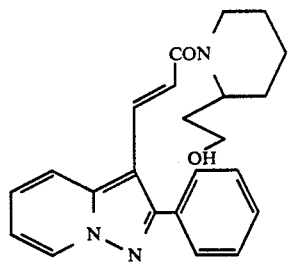

mp: 140.5°-141.5 ° C..
IR(Nujol): 3280, 1625, 1560, 1510 cm$^{-1}$.
NMR(CDCl$_3$, δ): 1.17~2.20(8H, m), 2.54~3.90(5H, m), 4.67~5.10(1H, m), 6.64(1H, d, J=16.5Hz), 6.85(1H, dt, J=7.0Hz and 1.0Hz), 7.15~7.77(7H, m), 7.92(1H, d, J=16.5Hz), 8.47(1H, d, J=7.0Hz).

Analysis Calcd for C$_{23}$H$_{25}$N$_3$O$_2$. C 73.58, H 6.71, N 11.19. Found C 73.50, H 6.56, N 11.14.

MS: 375 (M+).

Preparation 1

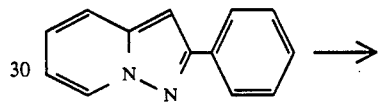

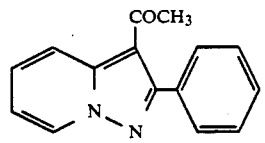

2-Phenylpyrazolo[1,5-a]pyridine (2.00 g) was added to a stirred solution of acetic anhydride (4.20 g) and two drops of sulfuric acid at room temperature. After being stirred under reflux for 14 hours, the reaction mixture was poured onto 80 ml of 4 N NaOH aqueous solution and extracted with chloroform (30 ml×2). The extracts were combined and washed with water (30 ml), saturated sodium chloride aqueous solution (30 ml), then dried over magnesium sulfate and evaporated in vacuo. The residual crystals were recrystallized from diisopropyl ether to give 2-phenyl-3-acetylpyrazolo-[1,5-a]pyridine (1.16 g).

mp: 84° to 85° C.
IR (Nujol): 1640, 1620, 1495 cm$^{-1}$.
NMR (CDCl$_3$, δ): 2.23 (3H, s), 7.04 (1H, td J=7Hz and 1Hz), 7.40-7.70 (6H, m), 8.51 (2H, t, 7Hz).

Analysis Calcd. for C$_{15}$H$_{12}$N$_2$O. C 76.25, H 5.12, N 11.86. Found: C 77.25, H 5.21, N 11.87.

MS: 236 (M+)

Preparation 2

Preparation 2

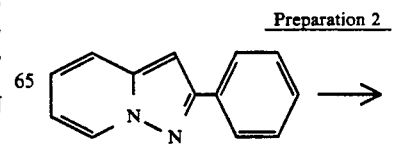

-continued
Preparation 2

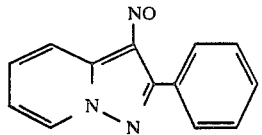

A solution of sodium nitrite (533 mg) in water (2.5 ml) was added dropwise to a solution of 2-phenylpyrazolo[1,5-a]pyridine (1.0 g) in acetic acid (5 ml) at 13° to 15° C. After being stirred at the same temperature for 20 minutes, the reaction mixture was poured onto ice-water. Resultant precipitates were collected by filtration, washed with water and recrystallized from acetone to give crystals of 3-nitroso-2-phenylpyrazolo[1,5-a]pyridine (0.82 g).

mp: 161° to 163° C.
IR (Nujol): 1620 cm$^{-1}$.
NMR (CDCl$_3$, δ): 7.28 (1H, td, J=6.5Hz and 2.0Hz), 7.17-8.02 (5H, m), 8.27-8.77 (3H, m).
Analysis Calcd. for C$_{13}$H$_9$N$_3$O: C 69.94, H 4.06, N 18.83. Found: C 70.26, H 4.18, N 18.97.
MS: 223 (M+).

EXAMPLE 25

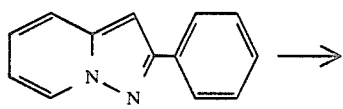

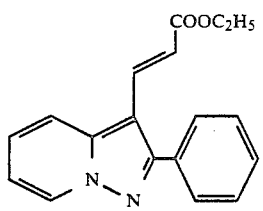

Aluminum chloride (298 mg) was added portionwise to a solution of 2-phenylpyrazolo[1,5-a]pyridine (145 mg) and ethyl 3-dimethylaminoacrylate (316 mg) in methylene chloride (2 ml) at 5° to 6° C. After being stirred at room temperature overnight, the reaction mixture was poured onto water (50 ml), neutralized with saturated aqueous sodium bicarbonate solution, and extracted with chloroform (50 ml×2). The extracts were washed with saturated sodium chloride aqueous solution (20 ml), dried over magnesium sulfate, and evaporated in vacuo. The residue was chromatographed on silica gel with a mixture of chloroform and n-hexane (1:1) as an eluent. The fractions containing the objective compound were combined and evaporated in vacuo to give ethyl 3-(2-phenylpyrazolo[1,5-a]pyridin-3-yl)acrylate (trans isomer) (189.4 mg).

IR (Nujol): 1690, 1615, 1510 cm$^{-1}$.
NMR (CDCl$_3$, δ): 1.30 (3H, t, J=6.0Hz), 4.27 (2H, q, J=6.0Hz), 6.30 (1H, d, J=16.0Hz), 6.88 (1H, td, J=6.0Hz and 2.0Hz), 7.16-8.33 (8H, m), 8.53 (1H, dd, J=8.0Hz and 1.0Hz).

EXAMPLE 26

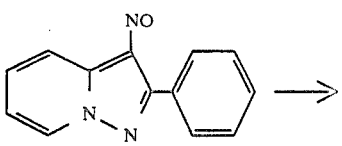

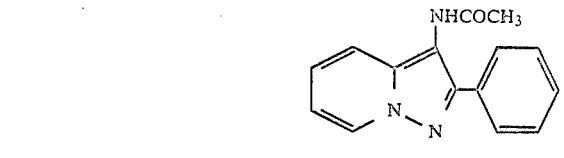

A mixture of 3-nitroso-2-phenylpyrazolo[1,5-a]pyridine (0.81 g) and zinc powder (0.95 g) in acetic acid (10 ml) was heated under reflux for 2.5 hours. The reaction mixture was poured onto ice-water (100 ml) and neutralized with saturated aqueous sodium bicarbonate solution. Resultant precipitates were collected by filtration, washed with water, and recrystallized from ethyl acetate to give crystals of 3-acetamido-2-phenylpyrazolo[1,5-a]pyridine (304 mg).

mp: 188° to 189° C.
IR (Nujol): 3170, 1640, 1530 cm$^{-1}$.
NMR (CDCl$_3$, δ): 2.20 (3H, s), 6.87 (1H, td, J=6.5Hz and 1.0Hz), 7.07-8.10 (8H, m), 8.27-8.57 (1H, m).
Analysis Calcd. for C$_{15}$H$_{13}$N$_3$O: C 71.69, H 5.21, N 16.72. Found: C 71.68, H 4.75, N 16.75.
MS: 251 (M+).

EXAMPLE 27

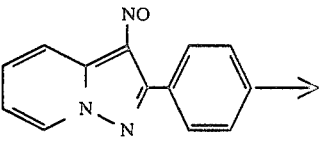

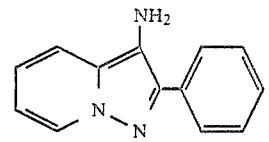

A mixture of 3-nitroso-2-phenylpyrazolo[1,5-a]pyridine (1.00 g), zinc powder and concentrated hydrochloric acid (0.4 ml) in ethanol (10 ml) was heated under reflux for 3 hours.

Ethanol was evaporated in vacuo. The mixture was neutralized with aqueous saturated sodium bicarbonate solution (20 ml) and extracted with chloroform (30 ml×2). The combined extracts were washed with saturated sodium chloride aqueous solution (20 ml), dried over magnesium sulfate and evaporated in vacuo. The crude crystals were recrystallized from ethyl acetate to give 3-amino-2-phenylpyrazolo[1,5-a]pyridine (531 mg).

mp: 155° to 157° C.
IR (Nujol): 3360, 3250, 1625 cm$^{-1}$.
NMR (CDCl$_3$, δ): 3.13 (2H, s), 6.60 (1H, td, J=7.0Hz and 2.0Hz), 6.97 (1H, td, J=7.0Hz and 1.0Hz), 7.27-8.10 (2H, m), 7.83-8.10 (2H, m), 8.32 (1H, dd, J=7.0Hz and 1.0Hz).
Analysis Calcd. for C$_{13}$H$_{11}$N$_3$: C 74.62, H 5.30, N 20.08. Found: C 74.88, H 4.85, N 20.15.

EXAMPLE 28

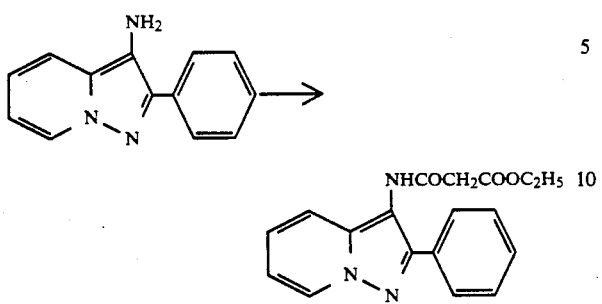

2-Ethoxycarbonylacetyl chloride (0.445 g) was added dropwise to a solution of triethylamine (0.298 g) and 3-amino-2-phenylpyrazolo[1,5-a]pyridine (0.560 g) in methylene chloride (10 ml) with ice-cooling.

The mixture was left at room temperature overnight. The mixture was poured into saturated sodium chloride aqueous solution (20 ml) and extracted with chloroform (20 ml×2). The combined extracts were washed with saturated sodium chloride aqueous solution (20 ml), dried over magnesium sulfate and evaporated in vacuo. The residue was chromatographed on silica gel (20 g) with chloroform as an eluent. The fractions containing the objective compound were combined, evaporated in vacuo and recrystallized from ethyl acetate to give crystals of 3-(2-ethoxycarbonylacetamido)-2-phenylpyrazolo[1,5-a]pyridine (0.48 g).

mp: 160°–161° C.

IR (Nujol): 3250, 1740, 1650, 1570 cm$^{-1}$.

NMR (CDCl$_3$, δ): 1.32 (3H, t, J=7.0Hz), 3.55 (2H, s), 4.30 (2H, q, J=7.0Hz), 6.79 (1H, td, J=7.0Hz and 1.5Hz), 7.20 (1H, t, J=7.0Hz), 7.38–7.67 (4H, m), 7.70–8.10 (2H, m), 8.45 (1H, d, J=7.0Hz), 8.75 (1H, broad s).

Analysis Calcd for C$_{18}$H$_{17}$N$_3$O$_3$: C 66.86, H 5.30, N 13.00. C 67.21, H 4.83, N 13.10.

EXAMPLE 29

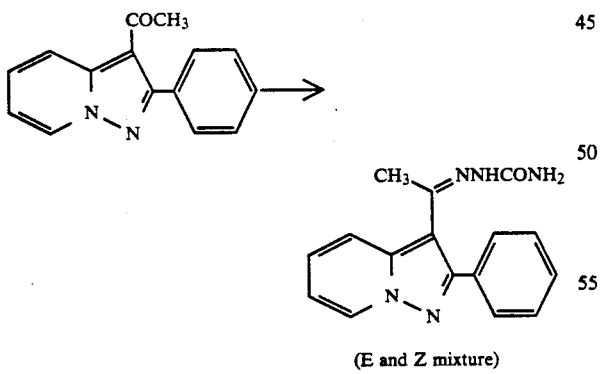

(E and Z mixture)

3-(1-Semicarbazonoethyl)-2-phenylpyrazolo[1,5-a]pyridine was obtained according to a similar manner to that of Example 1.

mp: 185° to 194° C.

IR (Nujol): 3750, 3200, 1685, 1580 cm$^{-1}$.

NMR (DMSO-d$_6$, δ): 1.95 ( 1.5H , s), 2.10 ( 1.5H, s), 6.10–6.33 (2H, m), 6.80–7.15 (1H, m), 7.29–8.00 (6H, m), 9.28 (1H, s), 8.55–8.90. (1H, m)

MS: 293 (M+).

The following compounds (Examples 30 to 38) were obtained according to a similar manner to that of Example 2.

EXAMPLE 30

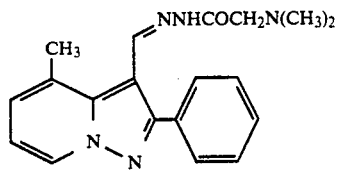

4-Methyl-2-phenylpyrazolo[1,5-a]pyridine-3-carbaldehyde [2-(dimethylamino)acetyl]hydrazone (E and Z mixture)

mp: 164°–165° C.

IR (Nujol): 3150, 1660 cm$^{-1}$.

NMR (DMSO-d$_6$, δ): 2.17 and 2.25 (Total 6H, s), 2.67 and 2.71 (Total 3H, s), 3.02 and 3.07 (Total 2H, s), 6.88–7.98 (7H, m), 8.46–8.86 (2H, m) .

Analysis Calcd. for C$_{19}$H$_{20}$N$_5$O: C 68.04, H 6.31, N 20.88 . Found: C 68.33, H 6.17, N 21.07.

EXAMPLE 31

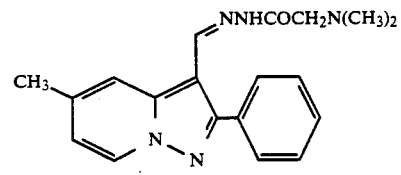

5-Methyl-2-phenylpyrazolo[1,5-a]pyridine-3-carbaldehyde [2-(dimethylamino)acetyl]hydrazone (E and Z mixture)

mp: 196°–197° C.

IR (Nujol): 1675, 1640, 1600, 1520 cm$^{-1}$.

NMR (DMSO-d$_6$, δ): 2.27 and 2.38 (Total 6H, s), 2.49 (3H, broad s), 3.00 and 3.52 (Total 3H, s), 7.02 (1H, broad d, J=7.0Hz), 7.48–8.38 (6H, m), 8.64–8.90 (2H, m).

Analysis Calcd. for C$_{19}$H$_{21}$N$_5$O: C 68.24, H 6.03, N 20.94. Found: C 67.96, H 6.21, N 20.68.

EXAMPLE 32

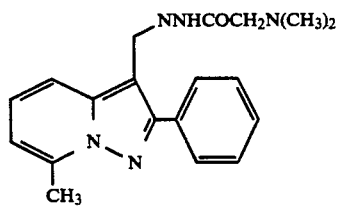

mp: 151°–153° C. IR (Nujol): 3300, 1660, 1620, 1590 cm$^{-1}$.

NMR (CDCl$_3$, δ): 2.33 (6H, s), 2.82 (3H, s), 3.12 (2H, s), 6.82 (1H, d, J=6.5Hz), 7.23–7.83 (6H, m), 8.37 (1H, s), 8.48 (1H, d, J=6.5Hz), 9.93 (1H, s).

Analysis Calcd. for C$_{19}$H$_{21}$N$_5$O: C 68.04, H 6.31, N 20.88. Found: C 68.29, H 6.20, N 20.29.

EXAMPLE 33

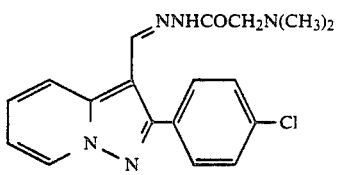

mp: 202°–205° C.
IR (Nujol): 3450, 1660, 1620 cm$^{-1}$.
NMR (DMSO-$d_6$, δ): 2.30 and 2.36 (Total 6H, s), 3.05 and 3.52 (Total 2H, s), 7.17 (1H, t, J=7.0Hz), 7.40–8.00 (5H, m), 8.00–9.00 (3H, m). Analysis Calcd. for $C_{18}H_{18}ClN_5O$: C 60~76, H 5.10, N 19.68. Found: C 61.06, H 5.08, N 19.79.
MS: 354 (M+).

EXAMPLE 34

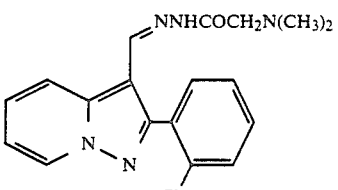

mp: 167°–168° C.
IR (Nujol): 3350, 1660, 1625, 1600 cm$^{-1}$.
NMR (CDCl$_3$, δ): 2.30 (6H, s), 3.10 (3H, s), 6.99 (1H, t, J=7.0Hz), 7.30–7.77 (6H, m), 7.99 (1H, s), 8.53 (2H, d, J=7.0Hz)
Analysis Calcd. for $C_8H_{18}ClN_5O$: C 60.76, H 5.10, N 19.68. Found: C 60.9,5, H 5.04, N 19.56.
MS: 355 (M+)

EXAMPLE 35

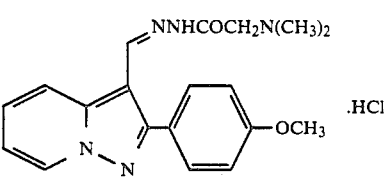

mp: 233°–236° C.
IR (Nujol): 1675, 1630, 1600 cm$^{-1}$.
NMR (DMSO-$d_6$, δ): 2.90 and 2.96 (Total 6H, s), 3.85 (3H, s), 4.07 and 4.58 (Total 2H, s), 7.00–7.33 (3H, m), 7.40–7.83 (3H, m), 8.17–9.00 (3H, m).
Analysis Calcd. for $C_{19}H_{21}N_5O_2 \cdot HCl$: C 58.84, H 5.72, N 18.06. Found: C 59.20, H 5.56, N 17.91.

EXAMPLE 36

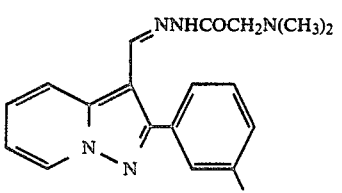

mp: 145°–147° C.

IR (Nujol): 1660, 1625, 1605, 1575 cm$^{-1}$. NMR (DMSO-$d_6$, δ): 2.25 and 2.35 (Total 6H, s), 3.01 and 3.53 (Total 2H, s), 3.87 (3H, s), 7.05–7.67 (6H, m), 8.20–8.93 (3H, m).
Analysis Calcd. for $C_{19}H_{21}N_5O_2$: C 64.94, H 6.02, N 19.93. Found: C 65.32, H 5.86, N 19.56.
MS: 351 (M+)

EXAMPLE 37

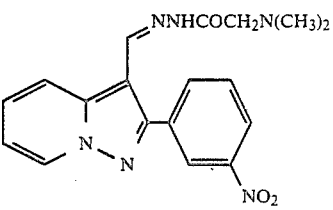

mp: 202°–206° C.
IR (Nujol): 1660, 1625 cm$^{-1}$.
NMR (DMSO-$d_6$, δ): 2.30 and 2.35 (Total 6H, s), 3.05 and 3.47 (Total 2H, s), 7.20 (1H, t, J=7.5Hz), 7.60 (1H, t, J=7.5Hz), 7.88 (1H, t, J=7.5Hz), 8.15–8.74 (5H, m), 8.94 (1H, d, J=7.5Hz).
Analysis Calcd. for $C_{18}H_{18}N_6O_3$: C 59.01, H 4.95, N 22.94. Found: C 58.91, H 4.74, N 22.95.

EXAMPLE 38

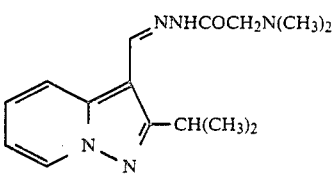

mp: 140°–141° C.
IR (Nujol): 1660, 1630, 1520 cm$^{-1}$.
NMR (CDCl$_3$, δ): 1.42 (6H, d, J=6Hz), 2.37 (6H, s), 3.13 (2H, s), 3.37 (1H, septet, J=6.0Hz), 6.85 (1H, td, J=6.5Hz and 2.0Hz), 7.33 (1H, td, J=6.5Hz and 2.0Hz), 8.37 (1H, d, J=6.5Hz), 8.43 (1H, d, J=6.5Hz), 8.15 (1H, s), 10.00 (1H, broad s).
Analysis Calcd. for $C_{15}H_{21}N_5O$:
C 62.70, H 7.37, N 24.37. Found: C 62.71, H 7.16, N 24.13.

The following compounds (Examples 39 to 55) were obtained according to a similar manner to that of Example 22.

EXAMPLE 39

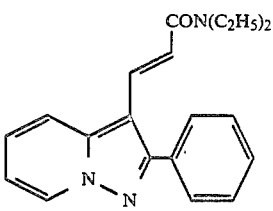

IR (CHCl$_3$): 1640, 1595, 1520 cm$^{-1}$.
NMR (CDCl$_3$, δ): 1.15 (6H, t, J=7Hz), 3.10–3.78 (4H, m), 6.56 (1H, d, J=16Hz), 6.86 (1H, td, J=7Hz and 1Hz), 7.22–7.90 (7H, m), 8.02 (1H, d, J=16Hz), 8.57 (1H, d, J=7Hz).

Analysis Calcd. for C20H21N3O.½H2O: C 73.14, H 7.05, N 12.79. Found: C 73.68, H 6.52, N 12.75.
MS: 319 (M+).

EXAMPLE 40

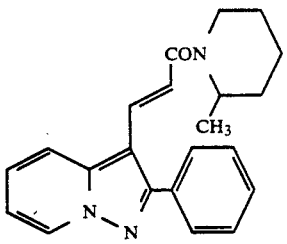

IR (CHCl3): 1640, 1590, 1515 cm$^{-1}$.
NMR (CDCl3, δ): 1.27 (3H, d, J=6Hz), 1.42–1.97 (6H, broad), 2.80–3.25 (1H, m), 4.00–4.85 (2H, m), 6.66 (1H, d, J=16Hz), 6.87 (1H, td, J=7Hz and 1Hz), 7.21–7.83 (7H, m), 7.93 (1H, d, J=16Hz), 8.52 (1H, d, J=7Hz).
Analysis Calcd. for C22H23N3O: C 76.49, H 6.71, N 12.16. Found: C 75.48, H 6.80, N 12.06
MS: 345 (M+).

EXAMPLE 41

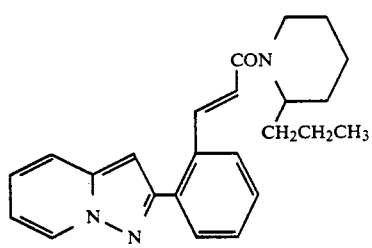

IR (Nujol): 1640, 1580, 1510 cm$^{-1}$.
NMR (CDCl3, δ): 0.88~1.97 (13H, m), 1.66–3.24 (1H, broad), 3.70–5.20 (2H, broad), 6.72 (1H, d, J=16Hz), 6.92 (1H, td, J=7Hz and 1Hz), 7.23–7.88 (7H, m), 8.00 (1H, d, J=16Hz), 8.60 (1H, d, J=7Hz) .
Analysis Calcd. for C24H27N3O: C 77.18, H 7.29, N 11.25. Found: C 76.46, H 7.19, N 11.13.
MS: 373 (M+)

EXAMPLE 42

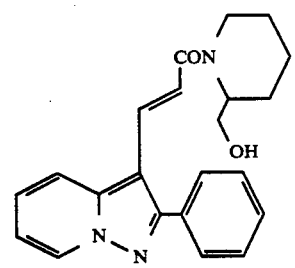

mp: 143° to 145° C.
IR (Nujol): 3320, 1635, 1575, 1500 cm$^{-1}$.
NMR (CDCl3, δ): 1.64 (6H, broad), 2.70–3.33 (1H, broad), 3.33–4.33 (3H, m), 4.33–4.66 (1H, broad), 6.75 (1H, d, J=16Hz), 6.78 (1H, t, J=6Hz), 7.13–7.86 (7H, m), 7.94 (1H, d, J=16Hz), 8.45 (1H, d, J=6Hz).
MS: 361 (M+) .

Analysis Calcd. for C22H23N3O2.½H2O: C 71.33, H 6.25, N 11.34. Found: C 72.11, H 6.31, N 11.38.

EXAMPLE 43

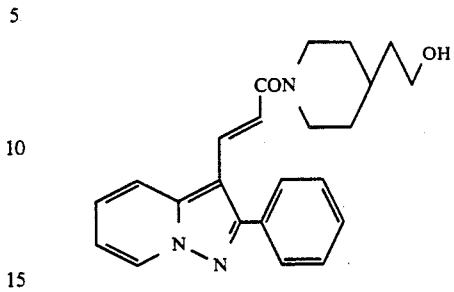

mp: 89° to 93° C.
IR (Nujol): 3400, 1640, 1590, 1530, 1510 cm$^{-1}$.
NMR (CDCl3, δ): 0.93–2.30 (7H, m), 2.47–3.28 (2H, m), 3.40 (2H, t, J=6Hz), 3.90–5.03 (2H, m), 6.70 (1H, d, J=15Hz), 6.90 (1H, td, d, J=7Hz and 1Hz), 7.22–7.80 (6H, m), 8.95 (1H, d, J=15Hz), 8.53 (1H, d, J=7Hz).
MS: 375 (M+).
Analysis Calcd. for C23H25N3O: C 73.58, H 6.71, N 11.19. Found: C 73.44, H 6.70, N 10.95.

EXAMPLE 44

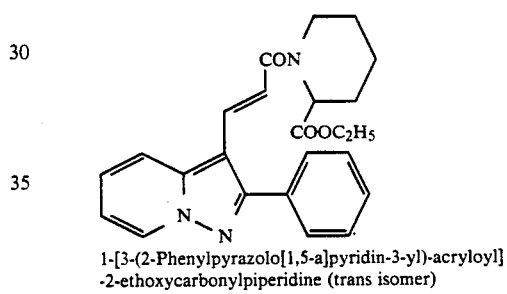

1-[3-(2-Phenylpyrazolo[1,5-a]pyridin-3-yl)-acryloyl]-2-ethoxycarbonylpiperidine (trans isomer)

IR (film): 1725, 1635, 1585, 1505 cm$^{-1}$.
NMR (CDCl3, δ): 1.21 (3H, t, J=8Hz), 1.33–2.00 (6H, m), 2.00–2.50 (1H, m), 3.00–3.50 (1H, m), 4.25 (2H, q, J=8Hz), 5.25–5.60 (1H, m).
Analysis Calcd. for C24H25N3O3.C2H5O:
C 69.47, H 6.73, N 9.35. Found: C 69.42, H 6.70, N 9.59.
MS: 403 (M+) .

EXAMPLE 45

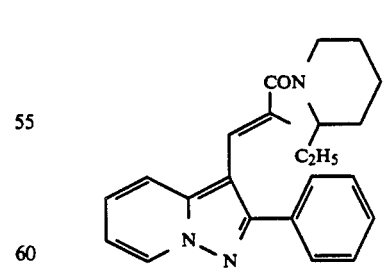

1-[2-Methyl-3-(2-phenylpyrazolo[1,5-a]pyridin-3-yl)-acryloyl]-2-ethylpiperidine (trans isomer)

mp: 133.5° to 134.5° C.
IR (Nujol): 1740, 1620, 1600, 1520 cm$^{-1}$.
NMR (CDCl3, δ): 0.90 (3H, t, J=7Hz), 1.33–2.00. (8H, m), 1.80 (3H, d, J=1Hz), 2.70–3.33 (1H, m), 3.96–4.66 (2H, m), 6.62 (1H, s), 6.85 (1H, td, J=7Hz and 1Hz), 7.13-7.70 (5H, m), 7.80-8.03 (2H, m), 8.57 (1H, d, J=7Hz).

Analysis Calcd. for C₂₄H₂₇N₃O: C 77.18, H 7.29, N 11.25. Found: C 76.04, H 7.34, N 10.64.

MS: 373 (M⁺).

EXAMPLE 46

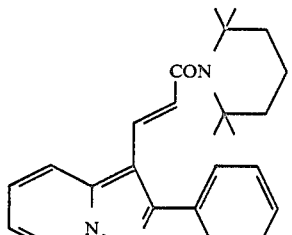

1-[3-(2-Phenylpyrazolo[1,5-a]pyridin-3-yl)-acryloyl]-2,2,6,6-tetramethylpiperidine (trans isomer)

mp: 158° to 159° C.

IR (Nujol): 1640, 1580, 1510 cm⁻¹.

NMR (CDCl₃, δ): 1.45 (12H, s), 1.78 (6H, s), 6.46 (1H, d, J=15Hz), 6.72 (1H, t, J=7Hz), 7.08-7.80 (8H, m), 8.48 (1H, d, J=7Hz).

Analysis Calcd. for C₂₅H₂₉N₃O: C 77.49, H 7.54, N 10.84. Found: C 77.75, H 7.49, N 10.74.

EXAMPLE 47

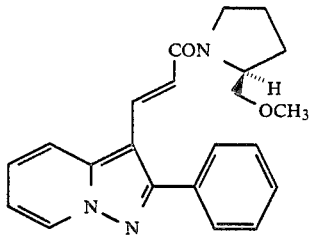

(2S)-1-[3-(2-Phenylpyrazolo[1,5-a]pyridin-3-yl)-acryloyl]-2-methoxymethylpyrrolidine (trans isomer)

IR (Nujol): 1700, 1640, 1590, 1520 cm⁻¹.

NMR (CDCl₃, δ): 1.77-2.15 (4H, m), 3.33 (3H, s), 3.20-3.72 (2H, m), 4.00-4.60 (1H, broad), 6.90 (1H, td, J=8Hz and 1Hz), 7.20-7.90 (8H, m), 8.02 (1H, d, J=16Hz), 8.57 (1H, d, J=8Hz). Analysis Calcd. for C₂₃H₂₅N₃O₂.H₂O. C 70.20, H 6.91, N 10.06. Found: C 70.05, H 6.69, N 9.93.

MS: 375 (M⁺).

[α]$_D^{26.8}$ = -70.44 (c=0.978, EtOH).

EXAMPLE 48

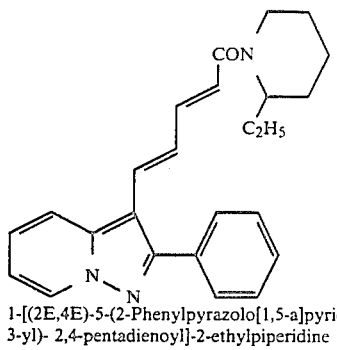

1-[(2E,4E)-5-(2-Phenylpyrazolo[1,5-a]pyridin-3-yl)-2,4-pentadienoyl]-2-ethylpiperidine IR (Nujol): 1620, 1580, 1500 cm⁻¹.

NMR (CDCl₃, δ): 0.88 (3H, t, J=6Hz), 1.10-2.00 (8H, m), 2.50-3.33 (1H, m), 3.66-5.00 (2H, m), 6.42 (1H, d, J=15Hz), 6.66-7.94 (11H, m), 8.59 (1H, d, J=7Hz).

Analysis Calcd. for C₂₅H₂₇N₃O. C 77.89, H 7.06, N 10.90. Found: C 77.57, H 6.95, N 10.69.

EXAMPLE 49

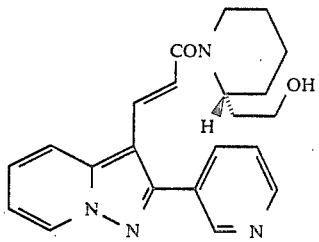

(2R)-1-[3-{2-(3-Pyridyl)pyrazolo[1,5-a]pyridin-3-yl}acryloyl]-2-(2-hydroxyethyl)piperidine (trans isomer)

mp: 137° to 139° C.

IR (Nujol): 3470, 1620, 1580 cm⁻¹.

NMR (CDCl₃, δ): 1.30-2.10 (6H, m), 2.60-3.20 (1H, m), 3.10-4.00 (2H, m), 3.90-4.40 (1H, m), 4.40-5.10 (1H, m), 6.62 (1H, d, J=16.0Hz), 6.87 (1H, t, J=7.5Hz), 7.28 (1H, t, J=7.5Hz), 7.38 (1H, t, J=7.5Hz), 7.58-8.05 (3H, m), 8 46 (1H, d, J=7.5Hz), 8.64 (1H, d, J=5.5Hz), 8.93 (1H, s).

Analysis Calcd. for C₂₂H₂₄N₄O₂: C 70.19, H 6.43, N 14.88. Found: C 70.13, H 6.39, N 14.85.

MS: 376 (M⁺).

EXAMPLE 50

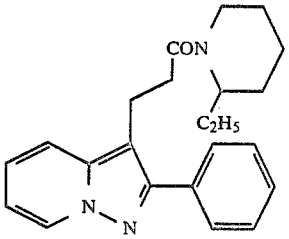

1-[3-(2-Phenylpyrazolo[1,5-a]pyridin-3-yl)propionyl]-2-ethylpiperidine

IR (Nujol): 1620, 1520 cm⁻¹.

NMR (CDCl$_3$, δ): 0.60–1.00 (3H, m), 1.20–1.90 (7H, m), 2.27–2.83 (4H, m), 3.10–3.67 (3H, m), 4.40–4.64 (1H, m), 6.60–8.90 (8H, m), 8.47 (1H, d, J=7Hz).

Analysis Calcd. for C$_{23}$H$_{27}$N$_3$O: C 76.42, H 7.53, N 11.62. Found: C 74.94, H 6.98, N 11.22.

MS: 361 (M+).

EXAMPLE 51

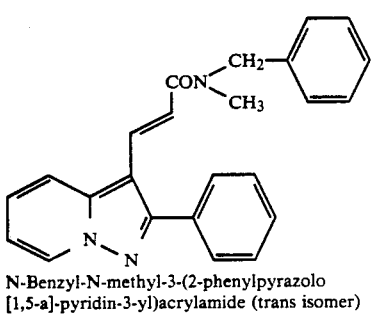

N-Benzyl-N-methyl-3-(2-phenylpyrazolo
[1,5-a]-pyridin-3-yl)acrylamide (trans isomer)

mp: 118° to 119° C.

IR (Nujol): 1610, 1510 cm$^{-1}$.

NMR (CDCl$_3$, δ): 3.05 (3H, s), 4.64 (2H, s), 6.70 (1H, d, J=15Hz), 6.90 (1H, t, J=7Hz), 7.10–8.00 (12H, m), 8.08 (1H, d, J=15Hz), 8.54 (1H, d, J=8Hz).

Analysis Calcd. for C$_{24}$H$_{21}$N$_3$O: C 78.44, H 5.76, N 11.44. Found: C 78.01, H 5.91, N 11.36.

MS: 367 (M+).

EXAMPLE 52

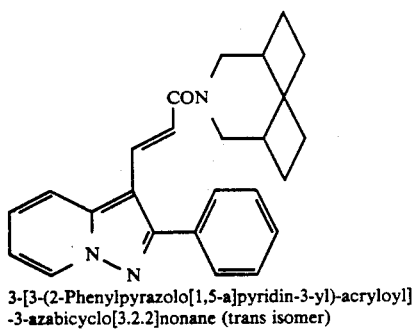

3-[3-(2-Phenylpyrazolo[1,5-a]pyridin-3-yl)-acryloyl]
-3-azabicyclo[3.2.2]nonane (trans isomer)

mp: 113° to 115° C.

IR (Nujol): 1630, 1580, 1500 cm$^{-1}$.

NMR (CDCl$_3$, δ): 1.67 (8H, m), 1.92–2.23 (2H, m), 3.50–4.00 (4H, m), 6.83 (1H, d, J=15Hz), 6.90 (1H, t, J=7.5Hz), 7.23–7.93 (7H, m), 7.97 (1H, d, J=15Hz), 8.56 (1H, d, J=7.5Hz).

Analysis Calcd. for C$_{24}$H$_{25}$N$_3$O: C 77.59, H 6.78, N 11.31. Found: C 77.57, H 6.96, N 11.32.

MS: 371 (M+).

EXAMPLE 53

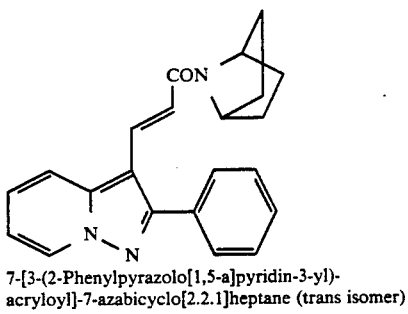

7-[3-(2-Phenylpyrazolo[1,5-a]pyridin-3-yl)-
acryloyl]-7-azabicyclo[2.2.1]heptane (trans isomer)

mp: 155.5° to 156.5° C.

IR (Nujol): 1635, 1590, 1510 cm$^{-1}$.

NMR (CDCl$_3$, δ): 1.25–2.00 (8H, m), 4.00–4.90 (2H, broad), 6.52 (1H, d, J=16Hz), 6.90 (1H, td, J=7Hz and 1Hz), 7.20–8.83 (7H, m), 7.95 (1H, d, J=16Hz), 8.56 (1H, d, J=7Hz).

Analysis Calcd. for C$_{22}$H$_{21}$N$_3$O: C 76.94, H 6.16, N 12.24. Found: C 77.28, H 6.05, N 12.54.

MS: 343 (M+).

EXAMPLE 54

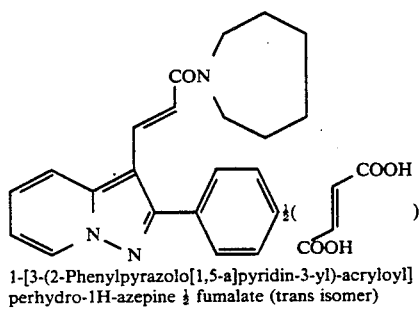

1-[3-(2-Phenylpyrazolo[1,5-a]pyridin-3-yl)-acryloyl]
perhydro-1H-azepine ½ fumalate (trans isomer)

mp: 146°–147° C.

IR (Nujol): 1685, 1635, 1580, 1520 cm$^{-1}$.

NMR (DMSO-d$_6$, δ): 1.33–1.90 (8H, broad), 3.35–3.80 (4H, m), 6.65 (2H, s), 6.82 (1H, d, J=15Hz), 7.13 (1H, t, J=7Hz), 7.42–7.90 (7H, m), 8.12 (1H, d, J=8Hz), 8.90 (1H, d, J=7Hz), 12.30–13.20 (1H, broad).

Analysis Calcd. for C$_{24}$H$_{25}$N$_3$O$_3$·½H$_2$O. C 69.88, H 6.59, N 10.19. Found: C 70.39, H 6.01, N 9.99.

MS: 345 (M+).

EXAMPLE 55

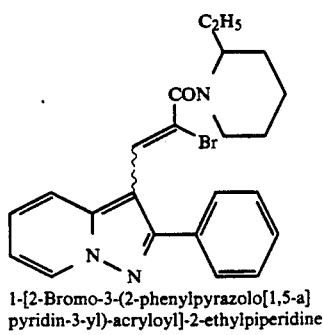

1-[2-Bromo-3-(2-phenylpyrazolo[1,5-a]
pyridin-3-yl)-acryloyl]-2-ethylpiperidine

NMR (CDCl$_3$, δ): 0.93 (3H, t, J=7.0Hz), 1.45–2.10 (8H, m), 2.42–3.37 (1H, m), 4.00–4.70 (2H, m), 6.87 (1H, td, J=7.0Hz and 2.0Hz), 7.67–7.95 (8H, m), 8.52 (1H, dd, J=6.5Hz and 1.0Hz).

MS: 437, 439 (M+).

EXAMPLE 56

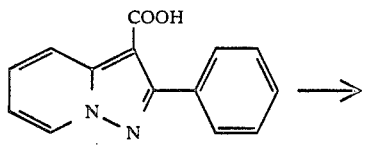

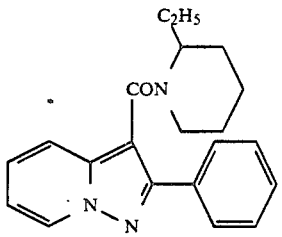

Thionyl chloride (240 mg) was added dropwise to a stirred mixture of 2-phenylpyrazolo[1,5-a]pyridine-3-carboxylic acid [compound (I)](320 mg) and N,N-dimethylformamide (one drop) in chloroform (10 ml), and then stirred under reflux for 4 hours.

After cooling the mixture, chloroform was evaporated in vacuo to give acid chloride of compound (I).

Triethylamine (338 mg) was added to a suspension of the acid chloride of compound (I) in methylene chloride (10 ml) under ice-cooling, and to this suspension a solution of 2-ethylpiperidine in methylene chloride was added dropwise. The mixture was stirred under ice-cooling and stood at room temperature overnight.

Saturated sodium chloride aqueous solution (20 ml) was added to the mixture and extracted with chloroform (20 ml). The extract was dried over magnesium sulfate and evaporated in vacuo. The residue was chromatographed on silica gel (8 g) with chloroform as an eluent. The fractions containing the objective compound were combined and evaporated in vacuo to give 1-(2-phenylpyrazolo[1,5-a]pyridin-3-ylcarbonyl)-2-ethylpiperidine (263 mg).

mp: 182°–183° C.

IR (Nujol): 1630, 1600, 1520 cm−1.

NMR (DMSO-d6, δ): 0.69 (3H, t, J=7.0Hz), 1.12–1.93 (8H, m), 2.73–3.17 (1H, m), 3.69–4.45 (2H, m) 7.07 (1H, td, J=7.0Hz and 2.0Hz), 7.29–8.00 (7H, m), 8.86 (1H, dd, J=7.0Hz and 1.0Hz).

Analysis Calcd. for C21H23N3O: C 75.65, H 6.95, N 12.60. Found: C 75.75, H 7.01, N 12.66.

EXAMPLE 57

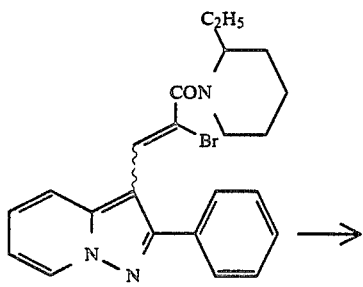

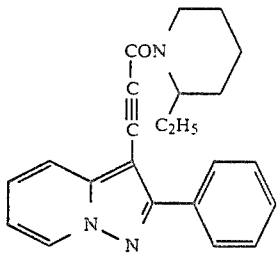

A mixture of potassium hydroxide (0.5 g) and 1-[2-bromo-3-(2-phenylpyrazolo[1,5-a]pyridin-3-yl)a-cryloyl]-2-ethylpiperidine (1.0 g) in ethanol (10 ml) was heated under reflux for 1.5 hours.

Ethanol was evaporated in vacuo and saturated sodium chloride aqueous solution (20 ml) was added to the residue. The mixture was extracted with ethyl acetate (20 ml×2). Combined extracts were washed with saturated sodium chloride aqueous solution (20 ml), dried over magnesium sulfate and evaporated in vacuo. The residue was chromatographed on silica gel with chloroform as an eluent. The fractions containing objective compound were combined and evaporated in vacuo to give 1-[3-(2-phenylpyrazolo[1,5-a]pyridin-3-1)propioloyl]-2-ethylpiperidine (0.71 g) as an oil.

IR (film): 2180, 1600, 1510 cm−1.

NMR (CDCl3, δ): 0.85 (3H, t, J=7.0Hz), 1.30–2.00 (8H, m), 2.40–3.43 (1H, m), 4.15–4.85, (2H, m), 6.90 (1H, td, J=7.0Hz and 2.0Hz), 7.17–8.33 (7H, m), 8.50 (1H, d, J=7.0Hz).

MS: 357 (M+).

EXAMPLE 58

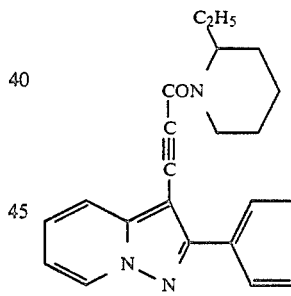

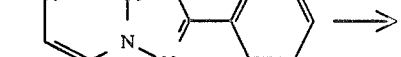

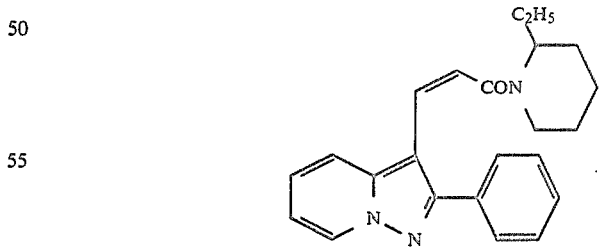

Lindler catalyst (21 mg) and quinoline (0.2 ml) were added to a solution of 1-[3-(2-phenylpyrazolo[1,5-a]-pyridin-3-yl)propioloyl]-2-ethylpiperidine (410 mg) in ethyl acetate (10 ml). The mixture was shaken with hydrogen.

The catalyst was filtered off and ethyl acetate was evaporated in vacuo. The residue was chromatographed on silica gel with a mixture of n-hexane and chloroform (1:1) as an eluent. The fractions containing objective compound were combined and evaporated in vacuo to give 1-[3-(2-phenylpyrazolo[1,5-a]pyridin-3-yl)acryloyl]-2-ethylpiperidine (cis isomer) (156.3 mg) as an oil.

IR (film): 1630, 1600, 1520 cm⁻¹.

NMR (CDCl₃, δ): 0.80 (3H, t, J=7.0Hz), 1.10-2.00 (8H, m), 2.30-3.20 (1H, m), 3.70-4.83 (2H, m), 6.17 (1H, d, J=12.5Hz), 6.57-8.03 (9H, m), 8.48 (1H, dd, J=7.0Hz and 1.0Hz).

EXAMPLE 59

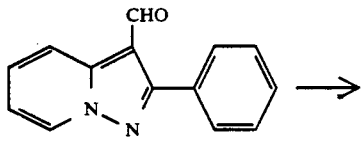

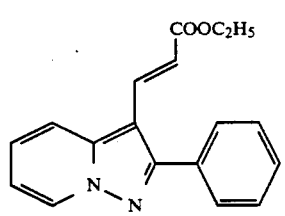

Triethyl phosphonoacetate (14.56 g) was added dropwise to a suspension of sodium hydride (60%, 2.60 g) in tetrahydrofuran (100 ml) with ice-cooling. After being stirred at room temperature for 1 hour, 2-phenylpyrazolo[1,5-a]pyridine-3-carbaldehyde (11.10 g) was added to the mixture, and then stirred at room temperature for 1 hour.

The reaction mixture was poured onto ice-water and extracted with ethyl acetate. The extract was washed with saturated sodium chloride aqueous solution, dried over magnesium sulfate, and evaporated in vacuo to give ethyl 3-(2-phenylpyrazolo[1,5-a]pyridin-3-yl)acrylate (trans isomer) (12.60 g).

mp: 130°-131° C.

IR (Nujol): 1690, 1615, 1510 cm⁻¹.

NMR (CDCl₃, δ): 1.30 (3H, t, J=6.0Hz), 4.27 (2H, q, J=6.0Hz), 6.30 (1H, d, J=16.0Hz), 6.88 (1H, td, J=6.0Hz and 2.0Hz), 7.16-8.33 (8H, m), 8.53 (1H, dd, J=8.0Hz and 1.0Hz).

The following compounds (Examples 60 and 61) were obtained according to a similar manner to that of Example 59.

EXAMPLE 60

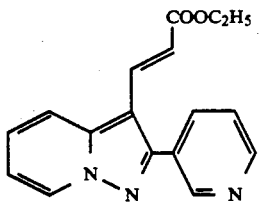

mp: 142° to 146° C.

IR (Nujol): 1690, 1620 cm⁻¹.

NMR (CDCl₃, δ): 1.15 (3H, t, J=7.5Hz), 4.08 (2H, q, J=7.5Hz), 6.10 (1H, d, J=16.0Hz), 6.74 (1H, t, J=7.5Hz), 7.03-7.40 (2H, m), 7.57-7.94 (3H, m), 7.78 (1H, s), 7.57-7.94 (3H, m), 8.35 (1H, d, J=7.5Hz), 8.52 (1H, d, J=4.5Hz)

EXAMPLE 61

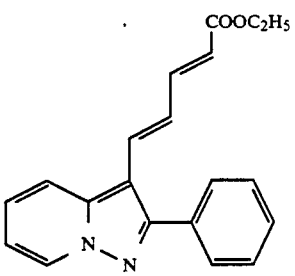

mp: 123.5° to 125.5° C.

IR (Nujol): 1705, 1605, 1500, 1260, 1235 cm⁻¹.

NMR (CDCl₃, δ): 1.30 (3H, t, J=6Hz), 4.23 (2H, q, J=6Hz), 5.89 (1H, d, J=15Hz), 98 (1H, d, J=15Hz), 6.60-6.97 (1H, m), 7.23-7.90 (9H, m), 8.55 (1H, d, J=8Hz).

Analysis Calcd. for C₂₀H₁₈N₂O₂: C 75.45, H 5.70, N 8.80. Found: C 75.87, H 5.57, N 8.90.

MS: 318 (M⁺)

EXAMPLE 62

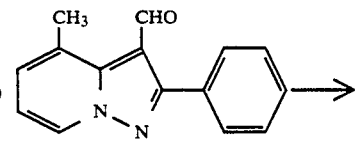

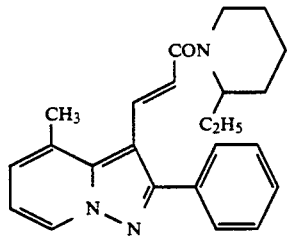

Sodium hydride (60%, 110mg) was added to a solution of 1-(2-diethoxyphosphorylacetyl)-2-ethylpiperidine (0.80 g) in tetrahydrofuran (5 ml) at 7° C. under nitrogen atmosphere. A solution of 4-methyl-2-phenylpyrazolo-[1,5-a]pyridine-3-carbaldehyde (0.50 g) in tetrahydrofuran (5 ml) was added dropwise to the above solution at 10° C., and then stirred at room temperature for 1 hour. After evaporating the solvent, in vacuo saturated sodium chloride aqueous solution (20 ml) was added to the residue and extracted with ethyl acetate (20 ml×2). Combined extracts were washed with saturated sodium chloride aqueous solution (20 ml), dried over magnesium sulfate and evaporated in vacuo. The residue was chromatographed on silica gel (20 g) with chloroform as an eluent. The fractions containing the objective compound were combined and evaporated in vacuo to give 1-[3-(4-methyl-2-phenylpyrazolo[1,5-a]pyridin-3-yl)acryloyl]-2-ethylpiperidine (trans isomer) (788 mg) as an oil.

IR (film): 1630, 1580, 1540 cm⁻¹.

NMR (CDCl₃, δ): 0.71 (3H, t, J=7.0Hz), 1.24-2.05 (8H, m), 2.79 (3H, s), 6.29 (1H, d, J=16.0Hz), 6.74 (1H, t, J=7.0Hz), 7.05 (1H, d, J=7.0Hz), 7.24-7.93 (5H, m), 8.24 (1H, d, J=16.0Hz), 8.38 (1H, d, J=7.0Hz).

MS: 373 (M⁺).

EXAMPLE 63

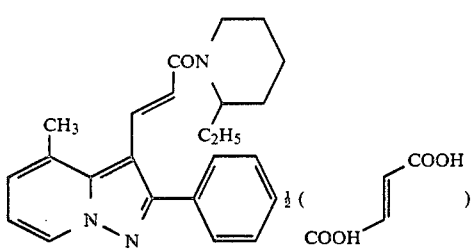

1-[3-(4-Methyl-2-phenylpyrazolo[1,5-a]pyridin-3-yl)acryloyl]-2 ethylpiperidine (trans isomer) was converted to 1-[3-(4-methyl-2-phenylpyrazolo[1,5-a]pyridin-3-yl)acryloyl]-2-ethylpiperidine 1/2 fumarate (trans isomer) according to a conventional manner.

mp: 124°–126° C.
IR (Nujol): 1685, 1620, 1530 cm$^{-1}$.
NMR (DMSO-d$_6$, δ): 0.62 (3H, t, J=7.0Hz), 1.06–1.90 (8H, m), 3.43–4.43 (2H, m), 6.24 (1H, d, J=16.0Hz), 6.67 (1H, s), 6.94 (1H, t, J=7.0Hz), 7.24 (1H, t, J=7.0Hz), 7.45–7.87 (5H, m), 8.05 (1H, d, J=16.0Hz), 8.67 (1H, d, J=7.5Hz).
Analysis Calcd. for C$_{24}$H$_{27}$N$_3$O.½C$_4$H$_4$O$_4$: C 72.54, H 6.56, N 9.76. Found: C 71.65, H 6.43, N 9.52.

The following compounds (Examples 64 to 79) were obtained according to a similar manner to that of Example 62 and/or Example 63.

EXAMPLE 64

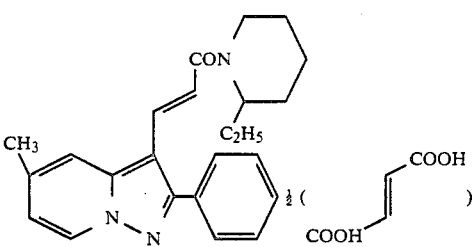

mp: 139°–141° C.
IR (Nujol): 1705, 1640 cm$^{-1}$.
NMR (DMSO-d$_6$, δ): 0.82 (3H, t, J=7.0Hz), 1.14–2.23 (8H, m), 2.50 (3H, s), 2.62–3.38 (1H, m), 4.07–4.70 (2H, m), 6.67 (1H, s), 6.88–7.20 (2H, m), 7.48–8.14 (7H, m), 8.81 (1H, d, J=7.0Hz).
Analysis Calcd. for C$_{24}$H$_{27}$N$_3$O.½C$_4$H$_4$O$_4$: C 68.69, H 6.38, N 8.58. Found: C 68.81, H 6.37, N 8.58.

EXAMPLE 65

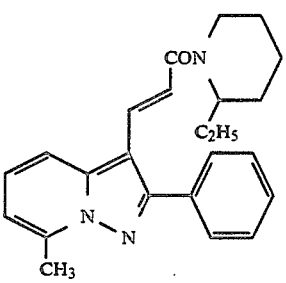

mp: 95°–97° C.

IR (Nujol): 1620, 1570, 1535, 1505 cm$^{-1}$.
NMR (CDCl$_3$, δ): 0.87 (3H, t, J=7.0Hz), 1.23–2.00 (8H, m), 2.80 (3H, s), 2.72–3.20 (1H, m), 3.83–4.67 (2H, m), 6.68 (1H, d, J=16.0Hz), 6.77 (1H, d, J=7.0Hz), 7.20 (1H, d, J=8.0Hz), 7.37–7.83 (6H, m), 8.00 (1H, d, J=16.0Hz).
Analysis Calcd. for C$_{24}$H$_{27}$N$_3$O: C 77.18, H 7.29, N 11.25. Found: C 77.15, H 7.18, N 11.14.

EXAMPLE 66

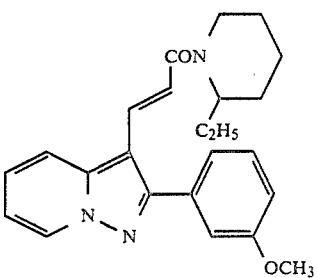

mp: 115°–118° C.
IR (Nujol): 1635, 1605, 1575 cm$^{-1}$.
NMR (DMSO-d$_6$, δ): 0.80 (3H, t, J=7.5Hz), 1.20–1.90 (8H, m), 2.60–3.10 (1H, m), 3.85 (3H, s), 3.90–4.60 (2H, m), 6.90 (1H, d, J=1.0Hz), 7.05–7.62 (6H, m), 7.76 (1H, d, J=16.0Hz), 8.14 (1H, d, J=9.0Hz), 8.87 (1H, d, J=7.5Hz).
Analysis Calcd. for C$_{24}$H$_{27}$N$_3$O$_2$: C 74.01, H 6.99, N 10.79. Found: C 73.98, H 6.88, N 10.76.

EXAMPLE 67

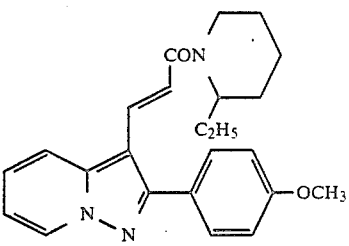

IR (CHCl$_3$): 1625, 1610, 1575 cm$^{-1}$.
NMR (CDCl$_3$, δ): 0.77 (3H, t, J=7.0Hz), 1.00–1.90 (8H, m), 2.50–3.20 (1H, m), 3.82 (3H, s), 3.60–4.75 (2H, m), 6.57–8.06 (7H, m), 8.50 (1H, d, J=7Hz).
Analysis Calcd. for C$_{24}$H$_{27}$N$_3$O.⅓H$_2$O: C 74.01, H 6.99, N 10.79. Found: C 73.09, H 6.98, N 10.47.
MS: 389 (M+).

EXAMPLE 68

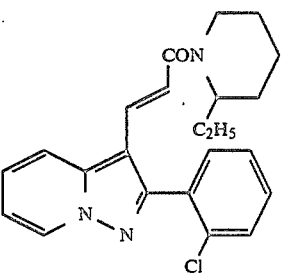

IR (film): 1635, 1580, 1515 cm$^{-1}$.

NMR (CDCl₃, δ): 0.78 (3H, t, J=7.0Hz), 1.22–1.93 (8H, m), 2.51–3.23 (1H, m), 3.50–4.72 (2H, m), 6.65 (1H, d, J=16.0Hz), 6.77–7.93 (8H, m), 8.53 (1H, d, J=7.0Hz) MS: 393 (M+).

EXAMPLE 69 mp: 136°–140° C.
IR (Nujol): 1705, 1635, 1550, 1510 cm⁻¹.
NMR (DMSO-d₆, δ): 0.80 (3H, t, J=7.0Hz), 1.30–1.90 (8H, m), 2.70–3.20 (1H, m), 3.93–4.67 (2H, m), 6.57–7.96 (8H, m), 8.15 (1H, d, J=8.0Hz), 8.84 (1H, d, J=7.0Hz)
Analysis Calcd. for C₂₃H₂₄ClN₃O.½C₄H₄O₄: C 66.44, H 5.80, N 9.30. Found: C 66.30, H 5.65, N 9.35.
MS: 392 (M+).

EXAMPLE 70 mp: 156°–158° C.
IR (Nujol): 1710, 1635 cm⁻¹.
NMR (DMSO-d₆, δ): 0.74 (3H, t, J=7.5Hz), 1.20–1.80 (8H, m), 2.60–3.20 (1H, m), 4.00–4.60 (2H, m), 6.65 (1H, s), 6.94 (1H, d, J=16.0Hz), 7.13 (1H, t, J=7.5Hz), 7.55 (1H, t, J=7.5Hz), 7.70 (1H, d, J=16.0Hz), 7.85 (1H, t, J=7.5Hz), 8.12 (2H, d, J=9.0Hz), 8.35 (1H, d, J=9.0Hz), 8.45 (1H, s), 8.28 (1H, d, J=7.5Hz).
Analysis Calcd. for C₂₃H₂₄N₄O₃.½C₄H₄O₄: C 64.92, H 5.67, N 12.11. Found: C 65.16, H 5.65, N 12.22.

EXAMPLE 71 mp: 170°–171° C.

IR (Nujol): 1635, 1575, 1510 cm⁻¹.
NMR (CDCl₃, δ): 0.82 (3H, t, J=7.5Hz), 1.20–1.80 (8H, m), 2.51–3.10 (1H, m), 3.70–4.70 (2H, m), 6.73 (1H, d, J=16.0Hz), 6.90 (1H, t, J=7.5Hz), 7.33 (1H, t, J=7.5Hz), 7.78 (1H, d, J=7.5Hz), 7.88 (1H, d, J=16.0Hz), 7.90 (2H, d, J=9.0Hz), 8.33 (2H, d, J=9.0Hz), 8.51 (1H, d, J=7.5Hz)
Analysis Calcd. for C₂₃H₂₄N₄O₃: C 68.30, H 5.98, N 13.85. Found: C 68.33, H 5.96, N 13.71.

EXAMPLE 72

NMR (CDCl₃, δ): 0.50–1.10 (3H, m), 1.08–2.30 (11H, m), 2.33–3.36 (1H, m), 3.36–4.20 (1H, m), 4.20–5.06 (1H, m), 6.14 (1H, s), 6.80 (1H, td, J=7Hz and 1Hz), 7.07–8.00 (8H, m), 8.50 (1H, d, J=7Hz)
MS: 373 (M+).

EXAMPLE 73 mp: 122° to 123° C.
IR (Nujol): 1630, 1580, 1540, 1510 cm⁻¹.
NMR (CDCl₃, δ): 0.83 (3H, t, J=7.0Hz), 1.25–2.02 (8H, m), 2.57–3.15 (2H, m), 3.95–4.60 (2H, m), 4.15 (3H, s), 6.22 (1H, dd, J=6.0Hz; and 3.0Hz), 6.60 (1H, d, J=16.0Hz), 7.26–8.12 (8H, m).
Analysis Calcd. for C₂₄H₂₇N₃O₂: C 74.01, H 6.99, N 10.79. Found: C 74.15, H 6.96, N 10.83.

EXAMPLE 74 mp: 132° to 133° C.
IR (Nujol): 1680, 1620 cm⁻¹.
NMR (DMSO-d₆, δ): 0.60 (3H, t, J=7.0Hz), 1.0–1.80 (8H, m), 6.25 (1H, d, J=16.0Hz), 6.67 (1H, s), 7.05 (1H, t, J=7.0Hz), 7.43–7.93 (6H, m), 8.17 (1H, d, J=16.0Hz), 9.82 (1H, d, J=7.0Hz).

Analysis Calcd. for C₂₃H₂₄ClN₃O.½C₄H₄O₄: C 66.44, H 5.80, N 9.30. Found: C 65.97, H 5.75, N 9.03.

EXAMPLE 75

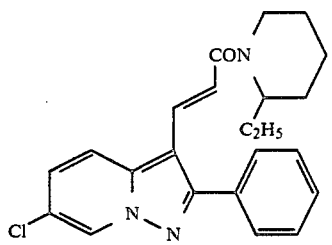

IR (film): 1630, 1580, 1505 cm⁻¹.
NMR (CDCl₃, δ): 0.83 (3H, t, J=7.0Hz), 1.37–1.87 (8H, m), 6.67 (1H, d, J=16.0Hz), 7.15–8.05 (8H, m), 8.53 (1H, broad s).
MS: 393 (M+).

EXAMPLE 76

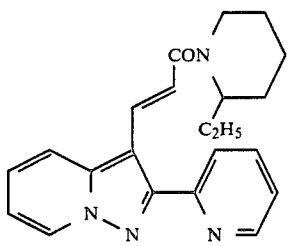

mp: 131°–133° C.
IR (Nujol): 1635, 1590, 1510 cm⁻¹.
NMR (CDCl₃, δ): 0.89 (3H, t, J=7.0Hz), 1.50–1.80 (8H, m), 2.80–3.20 (1H, m), 3.90–4.70 (2H, m), 6.88 (1H, d, J=7.0Hz), 6.97 (1H, d, J=16.0Hz), 7.20–7.43 (2H, m), 7.70–8.12 (3H, m), 8.36 (1H, d, J=16.0Hz), 8.51 (1H, d, J=7.0Hz), 8.80 (1H, d, J=6.0Hz).

Analysis Calcd. for C₂₂H₂₄N₄O: C 73.31, H 6.71, N 15.54. Found: C 73.50, H 6.55, N 15.50.

EXAMPLE 77

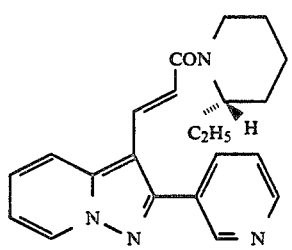

NMR (CDCl₃, δ): 0.82 (3H, t, J=7.5Hz), 1.20–1.90 (8H, m), 2.50–3.20 (1H, m), 3.60–4.90 (2H, m), 6.65 (1H, d, J=16.0Hz), 6.86 (1H, t, J=7.5Hz), 7.23 (1H, t, J=5.0Hz), 7.37 (1H, t, J=7.5Hz), 7.73 (1H, d, J=7.5Hz), 7.84 (1H, d, J=16.0Hz), 8.00 (1H, d, J=6.0Hz), 8.49 (1H, d, J=7.5Hz), 8.63 (1H, d, J=5.0Hz), 8.95 (1H, s)
MS: 360 (M+).

EXAMPLE 78

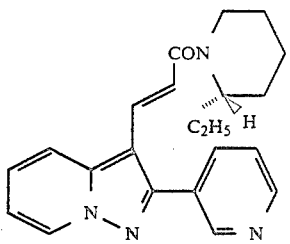

mp: 106° to 109° C.
IR (Nujol): 1700, 1635, 1580, 1560 cm⁻¹.
NMR (CDCl₃-DMSO-d₆, δ): 0.85 (3H, t, J=7.5Hz), 1.30–1.90 (8H, m), 2.40–3.20 (1H, m), 3.70–4.80 (2H, m), 6.72 (1H, d, J=16.0Hz), 6.77 (2H, s), 6.91 (1H, t, J=7.5Hz), 7.35 (1H, t, J=7.5Hz), 7.24–7.55 (2H, m), 7.80 (1H, d, J=7.5Hz), 7.83 (1H, d, J=16.0Hz), 8.04 (1H, d, J=7.5Hz), 8.53 (1H, d, J=7.5Hz), 8.66 (1H, d, J=5.0Hz), 8.95 (1H, s).

Analysis Calcd. for C₂₂H₂₄N₄O.½C₄H₄O₄: C 65.53, H 5.92, N 11.78. Found: C 64.43, H 5.98, N 11.50.

EXAMPLE 79

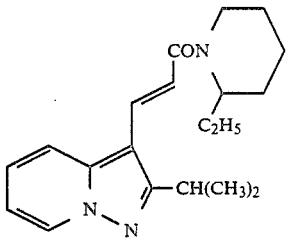

1-[3-(2-Isopropylpyrazolo[1,5-a]pyridin-3-yl)-acryloyl]-2-ethylpiperidine (trans isomer)

mp: 36°–38° C.
IR (Nujol): 1620 cm⁻¹.
NMR (CDCl₃, δ): 0.95 (3H, t, J=7.0Hz), 1.45 (6H, d, J=7.0Hz), 1.46–2.30 (8H, m), 2.77–3.37 (2H, m), 3.57 (1H, septet, J=7.0Hz), 4.25–4.97 (2H, m), 6.82 (1H, d, J=16.0Hz), 6.73–7.07 (1H, m), 7.38 (1H, td, J=7.0Hz and 1.0Hz), 7.80 (1H, dd, J=7.0Hz and 1.0Hz), 8.05 (1H, d, J=16.0Hz), 8.55 (1H, dd, J=7.0Hz and 1.0Hz).

Analysis Calcd. for C₂₀H₂₇N₃O: C 73.81, H 8.36, N 12.91. Found: C 72.53, H 8.19, N 12.56.

EXAMPLE 80

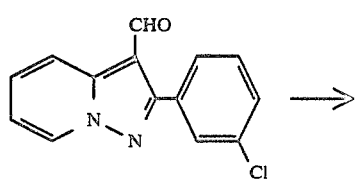

-continued

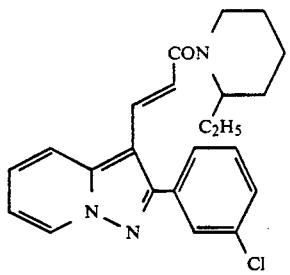

1-(2-Diethoxyphosphorylacetyl)-2-ethylpiperidine (0.80 g) was added dropwise to a suspension of sodium hydride (60%, 0.17 g) in tetrahydrofuran (3 ml) at to 31° C under nitrogen atomosphere, and then -(3-chlorophenyl)pyrazolo[1,5-a]pyridine-3-carbaldehyde (0.80 g) was added portionwise to the mixture.

After being stirred at 25° to 31° C. for 2 hours, tetrahydrofuran was evaporated in vacuo. Water was added to the residue and extracted with ethyl acetate. Extract was washed with aqueous potassium carbonate solution (×2) and saturated sodium chloride aqueous solution (×2), dried over magnesium sulfate and evaporated in vacuo.

The residue was chromatographed on silica gel (22 g) with a mixture of methylene chloride and ethyl acetate (10:1) as an eluent. The fractions containing the objective compound was combined and evaporated in vacuo 5 to give crystals of 1-[3-{2-(3-chlorophenyl)-pyrazolo[1,5-a]pyridin-3-yl}acryloyl]-2-ethylpiperidine (trans isomer) (0.37 g).

mp: 100°–104° C.

IR (Nujol): 1640, 1580, 1510 cm$^{-1}$.

NMR (CDCl$_3$, δ): 0.86 (3H, t, J=8.0Hz), 1.30–1.90 (8H, m), 2.60–3.20 (1H, m), 3.80–4.70 (2H, m), 6.65 (1H, d, J=16.0Hz), 6.85 (1H, t, J=7.5Hz), 7.15–7.75 (6H, m), 7.88 (1H, d, J=16.0Hz), 8.43 (1H, d, J=7.5Hz).

Analysis Calcd. for C$_{23}$H$_{24}$ClN$_3$O: C 70.13, H 6.14, N 10.68. Found: C 70.37, H 5.97, N 10.81.

MS: 393 (M+).

EXAMPLE 81

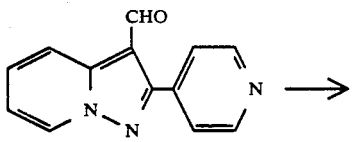

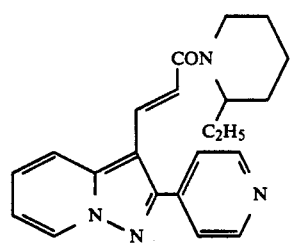

A solution of 1-(2-diethoxyphosphorylacetyl)-2-ethylpiperidine (0.99 g) in tetrahydrofuran (1.8 ml) was added dropwise to a suspension of sodium hydride (60%, 0.14 g) in tetrahydrofuran (4.5 ml) at 23° to 25° C. After being stirred at 24° C. for 30 minutes, 2-(4-pyridyl)pyrazolo[1,5-a]pyridine-3-carbaldehyde (0.63 g) was added to the mixture and then stirred at room temperature for 1 hour. The reaction mixture was poured into aqueous potassium carbonate solution and extracted with ethyl acetate (×2). The combined extracts were washed with saturated sodium chloride aqueous solution, dried over magnesium sulfate and evaporated in vacuo. The residue was chromatographed on silica gel (25 g) with a mixture of chloroform and methanol (100:1) as an eluent. The fractions containing objective compound were combined and evaporated in vacuo to give crystals. This was recrystallized from a mixture of ethanol and water (1:1) to give 1-[3-{2-(4-pyridyl)pyrazolo[1,5-a]pyridin-3-yl}acryloyl]-2-ethylpiperidine (trans isomer) (0.38 g).

mp: 150° to 153° C.

IR (Nujol): 1640, 1605 cm$^{-1}$.

NMR (CDCl$_3$, δ): 0.77 (3H, t, J=7.5Hz), 1.20–1.80 (8H, m), 2.50–3.20 (1H, m), 3.60–4.80 (2H, m), 6.65 (1H, d, J=16.0Hz), 6.85 (1H, t, J=7.5Hz), 7.26 (1H, t, J=7.5Hz), 33–7.97 (3H, m), 7.85 (1H, d, J=16.0Hz), 8.45 (1H, d, J=7.5Hz), 8.67 (1H, d, J=5.0Hz).

Analysis Calcd. for C$_{22}$H$_{24}$N$_4$O: C 73.31, H 6.71, N 15.54. Found: C 73.65, H 6.77, N 15.39.

The following compounds (Examples 82 and 83) were obtained according to a similar manner to that of Example 8.

EXAMPLE 82

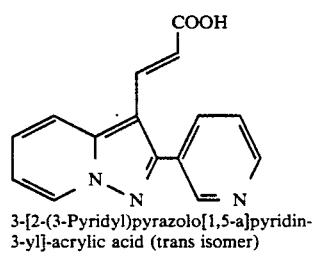

3-[2-(3-Pyridyl)pyrazolo[1,5-a]pyridin-3-yl]-acrylic acid (trans isomer)

mp: 251°–252° C. .

IR (Nujol): 1680, 1620, 1600 cm$^{-1}$.

NMR (CF$_3$COOH, δ): 6.47 (1H, d, J=15.0Hz), 7.25 (1H, t, J=6.5Hz), 7.60–8.22 (4H, m), 8.70–9.15 (4H, m).

EXAMPLE 83

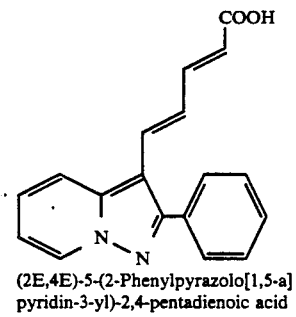

(2E,4E)-5-(2-Phenylpyrazolo[1,5-a]pyridin-3-yl)-2,4-pentadienoic acid mp: 230°–230.5° C. .

IR (Nujol): 1690, 1605, 1510 cm$^{-1}$.

NMR (DMSO-d$_6$, δ): 5.92 (1H, d, J=15Hz), 6.93–7.87 (10H, m), 8.13 (1H, d, J=8Hz), 8.83 (1H, d, J=8Hz)

MS: 290 (M+).

EXAMPLE 84

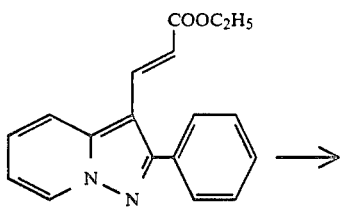

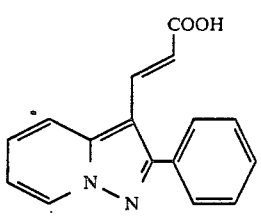

3-(2-Phenylpyrazolo[1,5-a]pyridin-3-yl)acrylic acid (trans isomer) was obtained from ethyl 3-(2-phenyl-pyrazolo[1,5-a]pyridin-3-yl)acrylate (trans isomer) according to a similar manner to that of Example 8.

The physical data were identical with those of the compound obtained in Example 8.

EXAMPLE 85

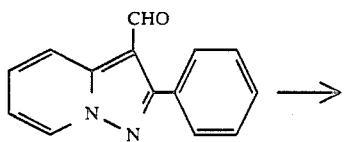

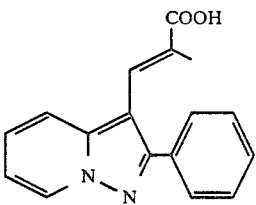

2-Methyl-3-(2-phenylpyrazolo[1,5-a]pyridin-3-yl)a-crylic acid (trans isomer) was obtained from 2-phenyl-pyrazolo[1,5-a]pyridine-3-carbaldehyde according to similar manners to those of Examples 7 and 8.

mp: 215° to 216° C.

IR (Nujol): 1700, 1630, 1520 cm$^{-1}$.

NMR (DMSO-d$_6$, δ): 1.80 (3H, s), 7.06 (1H, td, J=7Hz and 1Hz), 7.33-7.90 (8H, m), 8.86 (1H, d, J=7Hz).

MS: 278 (M+).

EXAMPLE 86

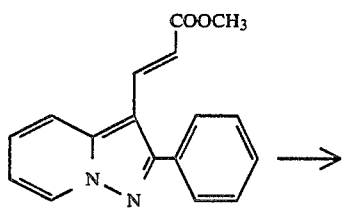

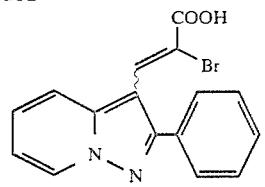

A solution of bromine (1.65 g) in chloroform (5 ml) was added dropwise to a solution of methyl 3-(2-phenylpyrazolo[1,5-a]pyridin-3-yl)acrylate (trans isomer) (1.65 g) in chloroform (25 ml) at 5° to 10° C. After being stirred at room temperature for 2 hours and 40 minutes, chloroform was evaporated in vacuo. 95% EtOH (15 ml) and potassium hydroxide (1.50 g) were added to the residue, and then the mixture was heated under reflux for 4.5 hours.

Ethanol was evaporated in vacuo, and the residue was dissolved in 1 N aqueous sodium hydroxide solution. Insoluble material was filtered off, and the filtrate was acidified with 5% hydrochloric acid. Resultant precipitates were collected by filtration and washed with water and methanol to give crystals of 2-bromo-3-(2-phenylpyrazolo[1,5-a]pyridin-3-yl)acrylic acid (1.29 g).

mp: 172° to 178° C. (dec.).

IR (Nujol): 1685, 1605 cm$^{-1}$.

NMR (DMSO-d$_6$, δ): 7.11 (1H, td, J=7.0Hz and 1.0Hz), 7.37-7.93 (7H, m), 8.38 (1H, s), 8.87 (1H, d, J=7.0Hz).

Analysis Calcd. for C$_{16}$H$_{11}$BrN$_2$O$_2$: C 56.00, H 3.21, N 8.17. Found: C 58.35, H 3.90, N 7.76.

EXAMPLE 87

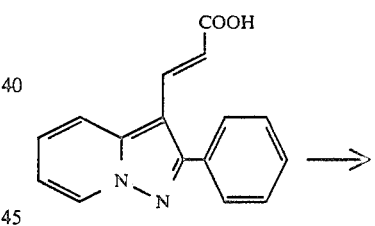

Thionyl chloride (0.38 ml) was added dropwise to a stirred mixture of 3-(2-phenylpyrazolo[1,5-a]pyridin-3-yl)acrylic acid (trans isomer) (1.06 g) and N,N-dimethylformamide (2 drops) in methylene chloride (6 ml) under ice-cooling. After being stirred at room temperature for 1 hour. n-Butanol was added dropwise to the stirring mixture under ice-cooling. After being stirred at room temperature for 10 minutes, the reaction mixture was poured into ice-water (20 ml), made basic (pH 12) and extracted with methylene chloride. The extract was washed with water, saturated sodium chloride aqueous solution, dried over magnesium sulfate, and evaporated.

The residue was recrystallized from a mixture of diisopropyl ether n-hexane to give n-butyl 3-(2-phenylpyrazolo[1,5-a]pyridin-3-yl)acrylate (trans isomer) (1.08 g).

mp: 80° to 82° C.

IR (Nujol): 1690, 1620, 1510 cm$^{-1}$.

NMR (CDCl$_3$, δ): 1.03 (3H, t, J=7Hz), 1.27-1.96 (4H, m), 4.25 (2H, t, J=7Hz), 6.33 (1H, d, J=15Hz), 6.97 (1H, td, J=7Hz and 1Hz), 7.25-7.97 (7H, m), 8.00 (1H, d, J=15Hz), 8.60 (1H, d, J=7Hz).

Analysis Calcd. for C$_{20}$H$_{20}$N$_2$O$_2$: C 74.98, H 6.29, N 8.74. Found: C 75.11, H 6.32, N 8.69.

EXAMPLE 88

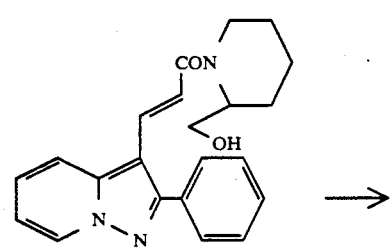

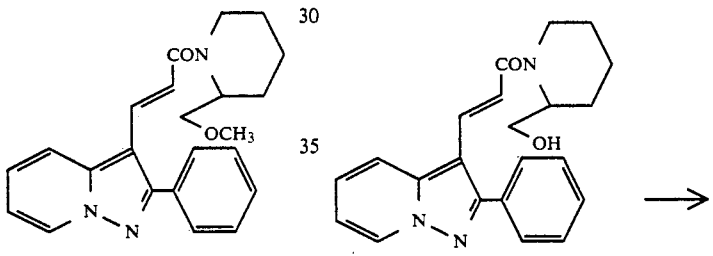

1-[3-(2-Phenylpyrazolo[1,5-a]pyridin-3-yl)acryloyl]2-hydroxymethylpiperidine (trans isomer) (0.30 g) was added to a stirred solution of tetrahydrofuran (2 ml) and sodium hydride (62.8%, 0.04 g) with ice-cooling. After 30 minutes, a solution of methyl iodide (0.14 g) in tetrahydrofuran (2 ml) was added to that stirred solution at 0° C. The reaction mixture was stirred for 4 hours at room temperature, then poured into water extracted with chloroform (20 ml), dried over magnesium sulfate and evaporated in vacuo. The residue was chromatographed on silica gel (20 g) with chloroform as an eluent. The fractions containing the objective compound were combined and evaporated in vacuo to give 1-[3-(2-phenylpyrazolo[1,5-a]pyridin-3-yl)acryloyl]-2-methoxymethylpiperidine (trans isomer) (0.30 g) as an oil.

IR (Nujol): 1640, 1590, 1510, 1440, 1415 cm$^{-1}$.

NMR (CDCl$_3$, δ): 1.15-1.80 (6H, m), 2.35-3.20 (1H, broad), 3.40 (3H, s), 3.90-4.80 (2H, broad), 6.70 (1H, d, J=16Hz), 6.78 (1H, td, J=7Hz and 1Hz), 7.00-7.77 (7H, m), 7.85 (1H, d, J=16Hz), 8.45 (1H, d, J=7Hz)

MS: 375 (M$^+$)

EXAMPLE 89

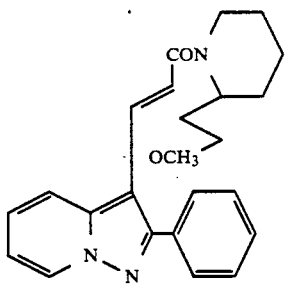

1-[3-(2-Phenylpyrazolo[1,5-a]pyridin-3-yl)acryloyl]2-(2-methoxyethyl)piperidine (trans isomer) was obtained according to a similar manner to that of Example 88.

mp: 139° to 140° C.

IR (Nujol): 1635, 1590, 1510 cm$^{-1}$. NMR, (CDCl$_3$, δ): 1.40-2.20 (9H, m), 2.30-3.10 (1H, m), 3.30 (3H, s), 3.95-5.05 (2H, m), 6.75-8.18 (10H, m), 8.55 (1H, d, J=7Hz)

Analysis Calcd. for C$_{24}$H$_{27}$N$_3$O$_2$: C 74.01, H 6.99, N 10.79. Found: C 73.79, H 6.51, N 10.69.

MS: 389 (M$^+$)

EXAMPLE 90

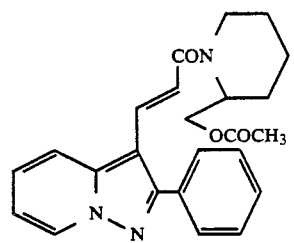

1-[3-(2-Phenylpyrazolo[1,5-a]pyridin-3-yl)acryloyl]2-hydroxymethylpiperidine (trans isomer) (0.50 g) was added to a stirred solution of acetic anhydride (0.16 g) in pyridine (5 ml) at room temperature, and stirred at room temperature for 3 hours. Ethyl acetate was added to the reaction mixture and washed with 1 N aqueous sodium hydroxide solution, water and saturated sodium chloride aqueous solution, then dried over magnesium sulfate and evaporated in vacuo. The residue was chromatographed on silica gel (50 g) with a mixture of chloroform and acetone (20:1) as an eluent. The fractions containing the objective compound were combined and evaporated in vacuo to give 1-[3-(2-phenylpyrazolo[1,5-a]pyridin-3-yl)acryloyl]-2-acetoxymethylpiperidine (trans isomer) (0.35 g) as an oil.

IR (CHCl$_3$): 1740, 1640, 1590 cm$^{-1}$.

NMR (CDCl$_3$, δ): 1.30-2.00 (8H, broad), 2.02 (3H, s), 2.65-3.15 (1H, m), 3.90-4.90 (2H, m), 6.73 (1H, d, J=18Hz), 6.94 (1H, dd, J=7.5Hz and 1.5Hz), 7.23–7.85 (7H, m), 7.97 (1H, d, J=18Hz), 8.53 (1H, d, J=7.5Hz).
MS: 403 (M+).

EXAMPLE 91

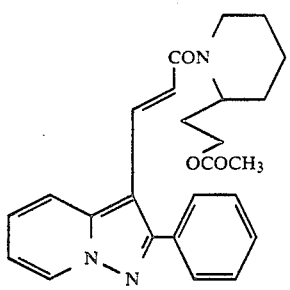

1-[3-(2-Phenylpyrazolo[1,5-a]pyridin-3-yl)acryloyl]2-(2-acetoxyethyl)piperidine (trans isomer) was obtained according to a similar manner to that of Example 90.

IR (CHCl3): 1725, 1635, 1585, 1515 cm$^{-1}$.

NMR (CDCl3, δ): 1.00–2.36 (7H, m), 1.90 (3H,.s), 2.48–3.30 (1H, broad), 4.02 (2H, t, J=6Hz), 4.4–5.0 (1H, broad), 6.65 (1H, d, J=16Hz), 6.83 (1H, td, J=6Hz and 1Hz), 7.18–7.80 (7H, m), 7.92 (1H, d, J=16Hz), 8.50 (1H, d, J=6Hz).

Analysis Calcd. for $C_{25}H_{27}N_3O_3\frac{1}{2}H_2O$: C 70.40, H 6.85, N 9.85. Found: C 70.96, H 6.59, N 9.71.
MS: 417 (M+)

EXAMPLE 92

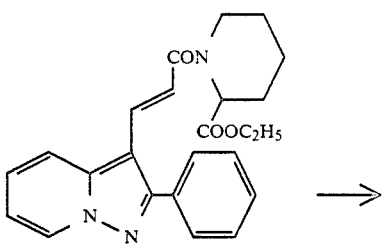

→

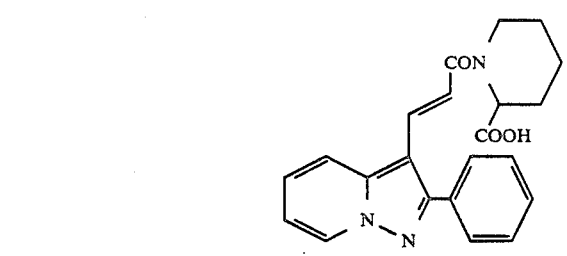

A mixture of 1-[3-(2-phenylpyrazolo[1,5-a]pyridin-3-yl)acryloyl]-2-ethoxycarbonylpiperidine (trans isomer) (0.50 g) and 1 N aqueous sodium hydroxide solution (5 ml) in methanol (5 ml) was refluxed for 3 hours. The reaction. mixture was evaporated to remove methanol, neutralized with 10% hydrochloric acid and extracted with chloroform. The extract was washed with saturated sodium chloride aqueous solution, dried over magnesium sulfate and evaporated in vacuo. The residue was chromatographed on silica gel (20 g) with chloroform as an eluent. The fractions containing the objective compound were combined and evaporated in vacuo to give 1-[3-(2-phenylpyrazolo[1,5-a]pyridin-3-yl)acryloyl]piperidine-2-carboxylic acid (trans isomer) (0.26 g) as an oil.

IR (Nujol): 3350, 1750, 1630, 1560, 1510 cm$^{-1}$.

NMR (DMSO-d6, δ): 1.07 (3H, t, J=7Hz), 1.20–1.85. (6H, broad), 2.00–2.45 (1H, broad), 3.47 (2H, q, J=7Hz), 3.90–4.75 (1H, broad), 4.75–5.30 (1H, m), 6.93 (1H; d, J=15Hz), 7.12 (1H, t, J=7Hz), 7.35–8.00 (7H, m), 8.18 (1H, d, J=7Hz), 8.80 (1H, d, J=7Hz)

Analysis Calcd. for $C_{22}H_{21}N_3O_3.H_2O$: C 67.16, H 5.89, N 10.68. Found: C 66.59, H 6.01, N 9.94.
MS: 375 (M+)

EXAMPLE 93

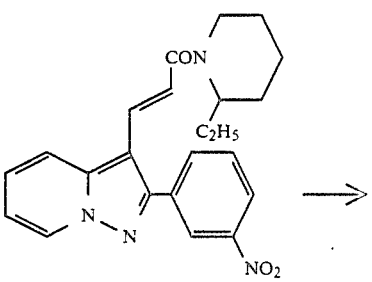

→

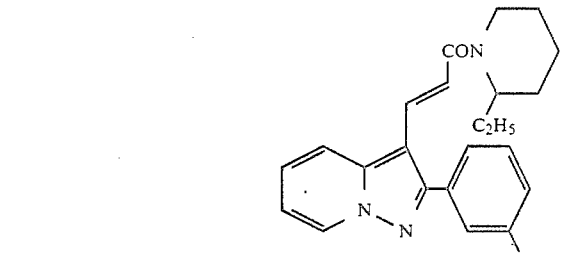

A solution of 1-[3-{2-(3-nitrophenyl)pyrazolo[1,5-a]pyridin-3-yl}acryloyl]-2-ethylpiperidine (trans isomer) (2.00 g) in ethanol (10 ml) was added dropwise to stirred mixture of iron powder (0.83 g) and ammonium chloride (0.08 g) in ethanol (20 ml) and water (10 ml) at 45° C. The reaction mixture was stirred at 69° C. for 3 hours and 20 minutes.

Insoluble inorganic materials were filtered off and the solvent was evaporated in vacuo. The residue was recrystallized from a mixture of ethanol and ethyl acetate (1:1) to give crystals of 1-[3-{2-(3-aminophenyl)-pyrazolo[1,5-a]pyridin-3-yl]acryloyl]-2-ethylpiperidine (trans isomer) (1.36. g).

mp: 150–151° C.

IR (Nujol): 3410, 3340, 3240, 1635, 1605 cm$^{-1}$.

NMR (CDCl3, δ): 0.82 (3H, t, J=7.5Hz), 1.20–1.80 (8H, m), 2.50–3.50 (2H, m), 3.80–4.70 (2H, m), 6.60–7.40 (7H, m), 7.74 (1H, d, J=9.0Hz), 7.93 (1H, d, J=16.0Hz), 8.49 (1H, d, J=7.5Hz).

Analysis Calcd. for $C_{23}H_{26}N_4O$: C 73.77, H 7.00, N 14.96. Found: C 73.37, H 6.87, N 14.80.
MS: 374 (M+)

EXAMPLE 94

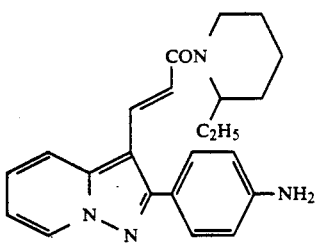

1-[3-{2-(4-Aminophenyl)pyrazolo[1,5-a]pyridin-3-yl}acryloyl]-2-ethylpiperidine (trans isomer) was obtained according to a similar manner to that of Example 93.

IR (Nujol): 3335, 3220, 1635, 1605, 1580 cm$^{-1}$.

NMR (CDCl$_3$, δ): 0.85 (3H, t, J=7.5Hz), 1.30–1.90 (8H, m), 2.50–3.10 (1H, m), 3.83 (1H, broad s), 3.90–4.70 (2H, m), 6.60–6.90 (3H, m), 7.25 (1H, t, J=7.5Hz), 7.42–7.80 (3H, m), 7.95 (1H, d, J=16.0Hz), 8.48 (1H, d, J=7.5Hz).

Analysis Calcd. for C$_{20}$H$_{27}$N$_3$O: C 73.77, H 7.00, N 14.96. Found: C 72.87, H 7.35, N 14.69.

MS: 374 (M$^+$)

EXAMPLE 95

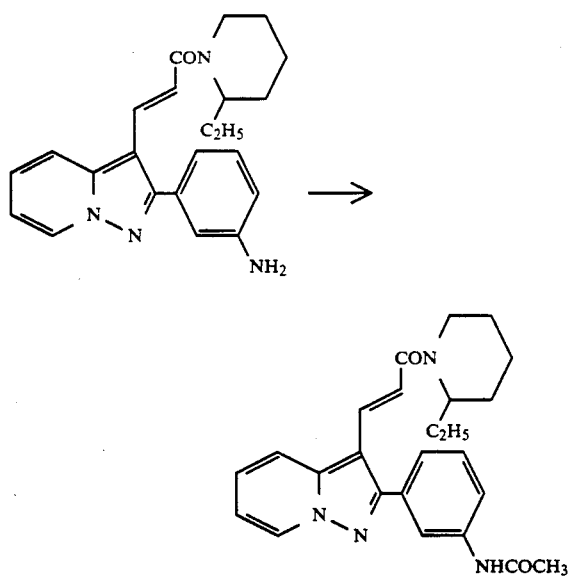

A mixture of 1-[3-{2-(3-aminophenyl)pyrazolo[1,5-a]pyridin-3-yl}acryloyl]-2-ethylpiperidine (trans isomer) (0.80 g) and acetic anhydride .(0.21 ml) in toluene (8 ml) was heated at 75° to 80° C. for 45 minutes.

The solvent was evaporated in vacuo. Water was added to the residue and extracted with methylene chloride. Combined extracts were washed with saturated sodium chloride aqueous solution, dried over magnesium sulfate and evaporated in vacuo to give crystals of 1-[3-{2-(3-acetamidophenyl)pyrazolo[1,5-a]pyridin-3-yl}-acryloyl]-2-ethylpiperidine (trans isomer) (0.33 g).

mp: 225–231° C.

IR (Nujol): 3380, 1685, 1635 cm$^{-1}$.

NMR (CDCl$_3$:DMSO=1:1, δ): 0.80 (3H, t, J=7.5Hz), 1.20–1.90 (8H, m), 2.05 (3H, s), 2.60–3.20 (1H, m), 3.90–4.60 (2H, m), 6.80 (1H, d, J=16.0Hz), 7.02 (1H, t, J=7.5Hz), 7.20–7.56 (3H, m), 7.60–8.10 (4H, m), 8.67 (1H, d, J=7.5Hz), 10.00 (1H, s).

Analysis Calcd. for C$_{25}$H$_{28}$N$_4$O$_2$: C 72.09, H 6.78, N 13.45. Found: C 71.49, H 6.48, N 13.33.

EXAMPLE 96

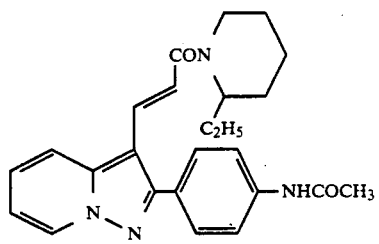

1-[3-{2-(4-Acetamidophenyl)pyrazolo[1,5-a]pyridin-3-yl}acryloyl]-2-ethylpiperidine (trans isomer) was obtained according to a similar manner to that of Example 95.

IR (Nujol): 3250, 1685, 1635, 1595 cm$^{-1}$.

NMR (DMSO-d$_6$, δ): 0.73 (3H, t, J=7.5Hz), 1.10–1.80 (8H, m), 2.03 (3H, s), 2.60–3.10 (1H, m), 3.20–4.60 (2H, m), 6.70–7.90 (8H, m), 8.09 (1H, d, J=9.0Hz).

MS: 416 (M$^+$).

EXAMPLE 97

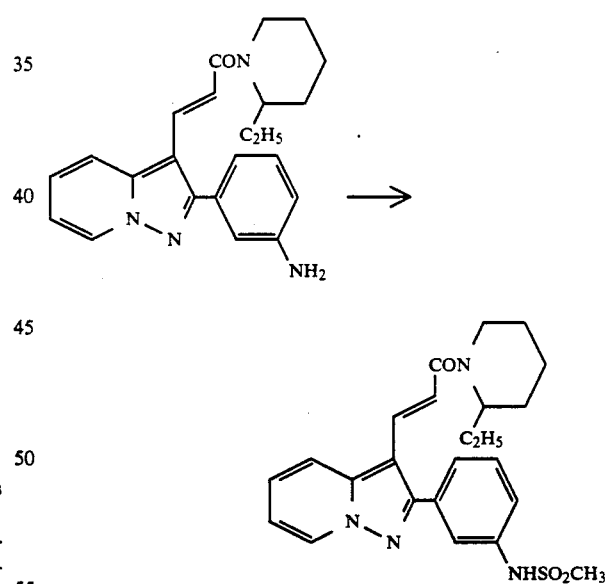

Methanesulfonyl chloride (0.59 g) was added dropwise to a stirred solution of 1-[3-{2-(3-amino-phenyl)-pyrazolo[1,5-a]pyridin-3-yl}acryloyl]-2-ethylpiperidine (trans isomer) (1.20 g) and triethylamine (0.52 g) in methylene chloride (7.2 ml) with ice-cooling. After being stirred at room temperature for 6 hours, the reaction mixture was washed twice with water and once with saturated sodium chloride aqueous solution, dried over magnesium sulfate and evaporated in vacuo. The residue was chromatographed on silica gel (22 g) with chloroform as an eluent. The fractions containing the objective compound were combined and evaporated in vacuo to give crystals of 1-[3-{2-(3-methanesulfonamidophenyl)pyrazolo[1,5-a]pyridin-3-yl}acryloyl]-2-ethylpiperidine (trans isomer) (0.36 g).

mp: 188°-190° C.

IR (Nujol): 3080, 1635, 1610 cm$^{-1}$.

NMR (DMSO-d$_6$, δ): 0.75 (3H, t, J=7.5Hz), 1.20-1.80 (8H, m), 2.60-3.20 (1H, m), 3.06 (3H, s), 3.90-4.70 (2H, m), 6.92 (1H, d, J=16.0Hz), 7.10 (1H, t, J=7.5Hz), 7.17-7.66 (5H, m), 7.73 (1H, d, J=16.0Hz), 8.12 (1H, d, J=9.0Hz), 8.87 (1H, d, J=7.5Hz), 10.01 (1H, s).

Analysis Calcd for C$_{24}$H$_{28}$N$_4$O$_3$S:
C 63.69, H 6.24, N 12.38. Found: C 63.52, H 6.44, N 12.29.

MS: 452 (M+).

EXAMPLE 98

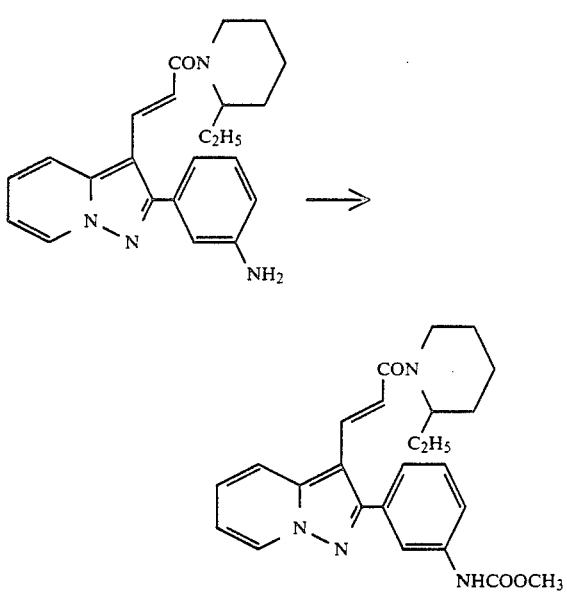

Methyl chloroformate (0.40 g) was added dropwise to a stirred solution of 1-[3-{2-(3-aminophenyl)-pyrazolo[1,5-a]pyridin-3-yl}acryloyl]-2-ethylpiperidine (trans isomer) (1.20 g) and triethylamine (0.44 g) in methylene chloride (7.2 ml) with ice-cooling.

After being stirred at room temperature for 6 hours, the reaction mixture was poured onto aqueous potassium carbonate solution and extracted with ethyl acetate. The extract was washed with water and saturated sodium chloride aqueous solution, dried over magnesium sulfate and evaporated in vacuo to give crystals of 1-[3-{2-(3-methoxycarbonylaminophenyl)pyrazolo[1,5-a]pyridin-3-yl}acryloyl]-2-ethylpiperidine (trans isomer) (0.31 g).

mp: 143°-145° C.

IR (Nujol): 3260, 1725, 1640 cm$^{-1}$.

NMR (DMSO-d$_6$, δ): 0.73 (3H, t, J=7.5Hz), 1.20-1.80 (8H, m), 2.60-3.10 (1H, m), 3.65 (3H, s), 3.80-4.60 (2H, m), 6.85 (1H, d, J=16.0Hz), 7.08 (1H, t, J=7.5Hz), 7.30 (1H, d, J=7.5Hz), 7.33-7.70 (4H, m), 7.80 (1H, d, J=2.0Hz), 8.10 (1H, d, J=9.0Hz), 8.80 (1H, d, J=7.5Hz), 9.84 (1H, s).

Analysis Calcd. for C$_{25}$H$_{28}$N$_4$O$_3$: C 69.42, H 6.52, N 12.95. Found: C 69.18, H 6.57, N 12.87.

MS: 432 (M+)

EXAMPLE 99

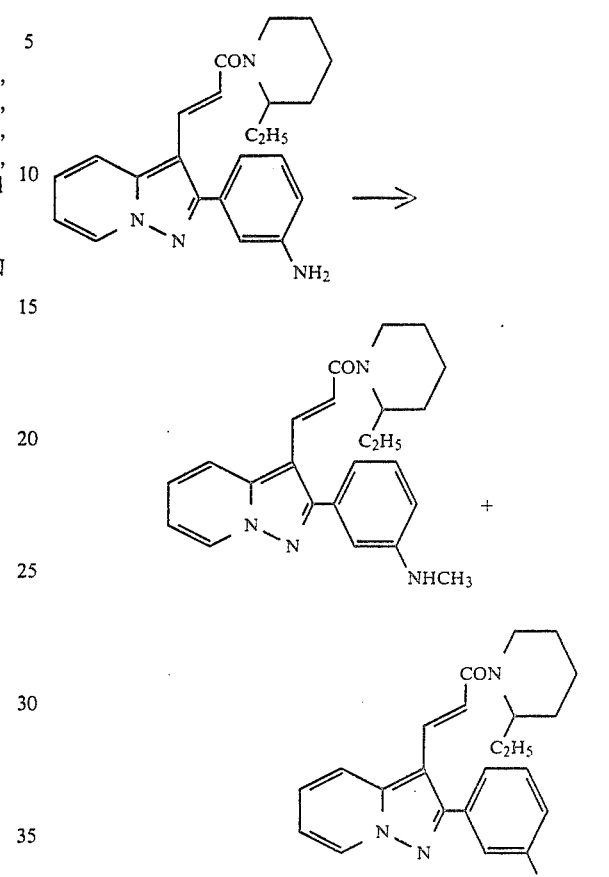

A solution of methyliodide (0.84 g) in N,N-dimethylformamide (2 ml) was added dropwise to a stirred mixture of 1-[3-{2-(3-aminophenyl)pyrazolo[1,5-a]pyridin-3-yl}acryloyl]-2-ethylpiperidine (trans isomer) (1.50 g) and powdered potassium carbonate (0.28 g) in N,N-dimethylformamide (10 ml) at room temperature. After being stirred at room temperature for 2 hours and 50 minutes, the reaction mixture was poured into water and extracted with ethyl acetate. The extract was washed with water and saturated sodium chloride aqueous solution, dried over magnesium sulfate and evaporated in vacuo. The residue was chromatographed on silica gel (36 g) with a mixture of methylene chloride and acetonitrile (5:1) as an eluent. The fractions containing major product were combined and evaporated in vacuo to give crystals of 1-[3-{2-(3-methylaminophenyl)pyrazolo[1,5-a]pyridin-3-yl}acryloyl]-2-ethylpiperidine (trans isomer) (0.21 g).

mp: 135°-141° C.

IR (Nujol): 3500, 1635, 1580, 1510 cm$^{-1}$.

NMR (CDCl$_3$, δ): 0.78 (3H, t, J=7.5Hz), 1.20-1.80 (8H, m), 2.84 (3H, s), 2.60-3.20 (1H, m), 3.70-4.70 (2H, m), 6.68 (1H, d, J=16.0Hz), 6.68-7.08 (4H, m), 7.27 (2H, t, J=7.5Hz), 7.72 (1H, d, J=9.0Hz), 7.94 (1H, d, J=16.0Hz), 8.49 (1H, d, J=7.5Hz).

Analysis Calcd. for C$_{24}$H$_{28}$N$_4$O: C 74.20, H 7.26, N 14.42. Found: C 74.07, H 7.45, N 14.30.

The fractions containing minor product were combined and evaporated in vacuo to give crystals of 1-[3-

{2-(3-dimethylaminophenyl)pyrazolo[1,5-a]pyridin-3-yl}acryloyl]-2-ethylpiperidine (trans isomer)(0.18 g).
mp: 180° to 184° C.
IR (Nujol): 1640, 1600 cm$^{-1}$.
NMR (CDCl$_3$, δ): 0.82 (3H, t, J=7.5Hz), 2.60-3.10 (1H, m), 3.70-4.60 (2H, m), 6.67 (1H, d, J=16.0Hz), 6.75-7.12 (4H, m), 7.28 (1H, t, J=7.5Hz), 7.78 (1H, d, J=9.0Hz), 7.95 (1H, d, J=16.0Hz), 8.53 (1H, d, J=7.5Hz).
Analysis Calcd. for C$_{25}$H$_{30}$N$_4$O. C 74.60, H 7.51, N 13.92. Found: C 74.18, H 6.87, N 14.20.
MS: 402 (M+)

The following compounds (Examples 100° to 131) were obtained according to a similar manner to that of Example 22.

EXAMPLE 100

1-[3-(2-Phenylpyrazolo[1,5-a]pyridin-3-yl)acryloyl]2-ethylpiperidine (cis isomer).
IR (film): 1630, 1600, 1520 cm$^{-1}$.

EXAMPLE 101

1-[3-(4-Methyl-2-phenylpyrazolo[1,5-a]pyridin-3-yl)acryloyl]2-ethylpiperidine (trans isomer).
IR (film): 1630, 1580, 1540 cm$^{-1}$.

EXAMPLE 102

1-[3-(5-Methyl-2-phenylpyrazolo[1,5-a]pyridin-3-yl)acryloyl]-2-ethylpiperidine ½fumalate (trans isomer).
IR (Nujol): 1705, 1640 cm$^{-1}$.

EXAMPLE 103

1-[3-(7-Methyl-2-phenylpyrazolo[1,5-a]pyridin-3-yl)acryloyl]-2-ethylpiperidine (trans isomer).
IR (Nujol): 1620, 1570, 1535, 1505 cm$^{-1}$.

EXAMPLE 104

1-[3-{2-(3-Methoxyphenyl)pyrazolo[1,5-a]pyridin-3-yl}acryloyl]-2-ethylpiperidine (trans isomer).
IR (Nujol): 1635, 1605, 1575 cm$^{-1}$.

EXAMPLE 105

1-[3-{2-(4-Methoxyphenyl)pyrazolo[1,5-a]pyridin-3-yl}acryloyl]-2-ethylpiperidine (trans isomer).
IR (CHCl$_3$): 1625, 1610, 1575 cm$^{-1}$.

EXAMPLE 105

1-[3-{2-(2-Chlorophenyl)pyrazolo[1,5-a]pyridin-3-yl}acryloyl]-2-ethylpiperidine (trans isomer).
IR (film): 1635, 1580, 1515 cm$^{-1}$.

EXAMPLE 107

1-[3-{2-(4-Chlorophenyl)pyrazolo[1,5-a]pyridin-3-yl}acryloyl]-2-ethylpiperidine ½fumalate (trans isomer).
IR (Nujol): 1705, 1635, 1550, 1510 cm$^{-1}$.

EXAMPLE 108

1-[3-{2-(3-Nitrophenyl)pyrazolo[1,5-a]pyridin-3-yl}acryloyl]-2-ethylpiperidine ½fumalate (trans isomer).
IR (Nujol): 1710, 1635 cm$^{-1}$.

EXAMPLE 109

1-[3-{2-(4-Nitrophenyl)pyrazolo[1,5-a]pyridin-3-yl}acryloyl]-2-ethylpiperidine (trans isomer).
IR (Nujol): 1635, 1575, 1510 cm$^{-1}$.

EXAMPLE 110

1-[3-(2-Phenylpyrazolo[1,5-a]pyridin-3-yl)isocrotonoyl]-2-ethylpiperidine.
MS: 373 (M+).

EXAMPLE 111

1-[3-(7-Methoxy-2-phenylpyrazolo[1,5-a]pyridin-3yl-)acryloyl]-2-ethylpiperidine (trans isomer).
IR (Nujol): 1630, 1580, 1540, 1510 cm$^{-1}$.

EXAMPLE 112

1-[3-(4-Chloro-2-phenylpyrazolo[1,5-a]pyridin-3yl)acryloyl]-2-ethylpiperidine ½fumalate (trans isomer).
IR (Nujol): 1680, 1620 cm$^{-1}$.

EXAMPLE 113

1-[3-(6-Chloro-2-phenylpyrazolo[1,5-a]pyridin-3yl)acryloyl]-2-ethylpiperidine (trans isomer).
IR (film): 1630, 1580, 1505 cm$^{-1}$.

EXAMPLE 114

1-[3-{2-(2-Pyridyl)pyrazolo[1,5-a]pyridin-3-yl}acryloyl]-2-ethylpiperidine (trans isomer).
IR (Nujol): 1635, 1590, 1510 cm$^{-1}$.

EXAMPLE 115

(2S)-1-[3-{2-(3-Pyridyl)pyrazolo[1,5-a]pyridin-3-yl}acryloyl]-2-ethylpiperidine (trans isomer).
MS: 360 (M+).

EXAMPLE 116

1-[3-(2-Isopropylpyrazolo[1,5-a]pyridin-3-yl)acryloyl]-2-ethylpiperidine (trans isomer).
IR (Nujol): 1620 cm$^{-1}$.

EXAMPLE 117

1-[3-{2-(3-Chlorophenyl)pyrazolo[1,5-a]pyridin-3-yl}acryloyl]-2-ethylpiperidine (trans isomer).
IR (Nujol): 1640, 1580, 1510 cm$^{-1}$.

EXAMPLE 118

1-[3-{2-(4-Pyridyl)pyrazolo[1,5-a]pyridin-3-yl]acryloyl]-2-ethylpiperidine (trans isomer).
IR (Nujol): 1640, 1605 cm$^{-1}$.

EXAMPLE 119

1-[3-(2-Phenylpyrazolo[1,5-a]pyridin-3-yl)acryloyl]-2-methoxymethylpiperidine (trans isomer).
IR (Nujol): 1640, 1590, 1510, 1440, 1415 cm$^{-1}$.

EXAMPLE 120

1-[3-(2-Phenylpyrazolo[1,5-a]pyridin-3-yl)acryloyl]-2-(2-methoxyethyl)piperidine (trans isomer).
IR (Nujol): 1635, 1590, 1510 cm$^{-1}$.

EXAMPLE 121

1-[3-(2-Phenylpyrazolo[1,5-a]pyridin-3-yl)acryloyl]-2-acetoxymethylpiperidine (trans isomer).
IR (CHCl$_3$): 1740, 1640, 1590 cm$^{-1}$.

EXAMPLE 122

1-[3-(2-Phenylpyrazolo[1,5-a]pyridin-3-yl)acryloyl]-2-(2-acetoxyethyl)piperidine (trans isomer).
IR (CHCl$_3$): 1725, 1635, 1585, 1515 cm$^{-1}$.

EXAMPLE 123

1-[3-(2-Phenylpyrazolo[1,5-a]pyridin-3-yl)acryloyl]-piperidine-2-carboxylic acid (trans isomer).
IR (Nujol): 3350, 1750, 1630, 1560, 1510 .cm$^{-1}$.

EXAMPLE 124

1-[3-{2-(3-Aminophenyl)pyrazolo[1,5-a]pyridin-3-yl}-acryloyl]-2-ethylpiperidine (trans isomer).
IR (Nujol): 3410, 3340, 3240, 1635, 1605 cm$^{-1}$.

EXAMPLE 125

1-[3-{2-(4-Aminophenyl)pyrazolo[1,5-a]pyridin-3-yl}acryloyl]-2-ethylpiperidine (trans isomer).
IR (Nujol): 3335, 3220, 1635, 1605, 1580 cm$^{-1}$.

EXAMPLE 126

1-[3-{2-(3-Acetamidophenyl)pyrazolo[1,5-a]pyridinacryloyl]-2-ethylpiperidine (trans isomer).
IR (Nujol): 3380, 1685, 1635 cm$^{-1}$.

EXAMPLE 127

1-[3-{2-(4-Acetamidophenyl)pyrazolo[1,5-a]pyridin-3-yl}acryloyl]-2-ethylpiperidine (trans isomer).
IR (Nujol): 3250, 1685, 1635, 1595 cm$^{-1}$.

EXAMPLE 128

1-[3-{2-(3-Methanesulfonamidophenyl)pyrazolo[1,5-a]pyridin-3-yl}acryloyl]-2-ethylpiperidine (trans isomer).
IR (Nujol): 3080, 1635, 1610 cm$^{-1}$.

EXAMPLE 129

1-[3-{2-(3-Methoxycarbonylaminophenyl)-pyrazolo[1,5-a]pyridin-3-yl}acryloyl]-2-ethylpiperidine (trans isomer).
IR (Nujol): 3260, 1725, 1640 cm$^{-1}$.

EXAMPLE 130

1-[3-{2-(3-Methylaminophenyl)pyrazolo[1,5-a]pyridin-3-yl}acryloyl]-2-ethylpiperidine (trans isomer).
IR (Nujol): 3500, 1635, 1580, 1510 cm$^{-1}$.

EXAMPLE 131

1-[3-{2-(3-Dimethylaminophenyl)pyrazolo[1,5-a]pyridin-3-yl}acryloyl]-2-ethylpiperidine (trans isomer).
IR (Nujol): 1640, 1600 cm$^{-1}$.

The following compounds (Examples 132° to 174) were obtained according to a similar manner to that of Example 62 (and Example 63).

EXAMPLE 132

1-[3-(2-Phenylpyrazolo[1,5-a]pyridin-3-yl)acryloyl]2-ethylpiperidine ½fumalate (trans isomer).
IR (Nujol): 1705, 1635, 1580, 1540, 1510 cm$^{-1}$.

EXAMPLE 133

1-[3-(2-Phenylpyrazolo[1,5-a]pyridin-3-yl)acryloyl]-pyrrolidine (trans isomer).
IR (Nujol): 1640, 1590 cm$^{-1}$.

EXAMPLE 134

1-[3-(2-Phenylpyrazolo[1,5-a]pyridin-3-yl)acryloyl]-piperidine (trans isomer).
IR (Nujol): 1630, 1580 cm$^{-1}$.

EXAMPLE b 135

4-[3-(2-Phenylpyrazolo[1,5-a]pyridin-3-yl)acryloyl]-morpholine (trans isomer).
IR (Nujol): 1625, 1580 cm$^{-1}$.

EXAMPLE 136

1-[3-(2-Phenylpyrazolo[1,5-a]pyridin-3-yl)acryloyl]4-methylpiperazine hydrochloride (trans isomer).
IR (Nujol): 2400, 1650, 1580, 1500 cm$^{-1}$.

EXAMPLE 137

N-Methyl-3-(2-phenylpyrazolo[1,5-a]pyridin-3-yl)acrylamide (trans isomer).
IR (Nujol): 3275, 1640, 1605 cm$^{-1}$.

EXAMPLE 138

N-Isopropyl-3-(2-phenylpyrazolo[1,5-a]pyridin-3-yl)acrylamide (trans isomer).
IR (Nujol): 3275, 1640, 1600 cm$^{-1}$.

EXAMPLE 139

N,N-Dimethyl-3-(2-phenylpyrazolo[1,5-a]pyridin-3-yl)acrylamide (trans isomer).
IR (Nujol): 1640, 1590 cm$^{-1}$.

EXAMPLE 140

N-(Tricyclo[3.3.1.1$^{3,7}$]decan-1-yl)-3-(2-phenylpyrazolo[1,5-a]pyridin-3-yl)acrylamide (trans isomer).
IR (Nujol): 3280, 1650, 1590, 1535, 1500 cm$^{-1}$.

EXAMPLE 141

(2R)-1-[3-(2-Phenylpyrazolo[1,5-a]pyridin-3-yl)acryloyl]-2-ethylpiperidine (trans isomer).
IR (film): 2930, 2860, 1635, 1585 cm$^{-1}$.

EXAMPLE 142

(2S)-1-[3-(2-Phenylpyrazolo[1,5-a]pyridin-3-yl)acryloyl]-2-ethylpiperidine (trans isomer).
IR (film): 2930, 2860, 1635, 1585 cm$^{-1}$.

EXAMPLE 143

(2R)-1-[3-(2-Phenylpyrazolo[1,5-a]pyridin-3-yl)acryloyl]-2-(2-hydroxyethyl)piperidine trans isomer).
IR (Nujol): 3350, 1640, 1575, 1520 cm$^{-1}$.

EXAMPLE 144

(2S)-1-[3-(2-Phenylpyrazolo[1,5-a]pyridin-3-yl)acryloyl]-2-(2-hydroxyethyl)piperidine (trans isomer).
IR(CHCl$_3$) 3330, 1635, 1570, 1520 cm$^{-1}$.

EXAMPLE 145

(2RS)-1-[3-(2-Phenylpyrazolo[1,5-a]pyridin-3-yl)acryloyl]-2-(2-hydroxyethyl)piperidine (trans isomer).
IR (Nujol): 3280, 1625, 1560, 1510 cm$^{-1}$.

EXAMPLE 146

N,N-Diethyl-3-(2-phenylpyrazolo[1,5-a]pyridin-3-yl)acrylamide (trans isomer).
IR (CHCl$_3$): 1640, 1595, 1520 cm$^{-1}$.

EXAMPLE 147

1-[3-(2-Phenylpyrazolo[1,5-a]pyridin-3-yl)acryloyl]-2-methylpiperidine (trans isomer).
IR (CHCl$_3$): 1640, 1590, 1515 cm$^{-1}$.

EXAMPLE 148

1-[3-(2-Phenylpyrazolo[1,5-a]pyridin-3-yl)acryloyl]-2-propylpiperidine (trans isomer).
IR (Nujol): 1640, 1580, 1510 cm$^{-1}$.

EXAMPLE 149

1-[3-(2-Phenylpyrazolo[1,5-a]pyridin-3-yl)acryloyl]-2-hydroxymethylpiperidine (trans isomer).
IR (Nujol): 3320, 1635, 1575, 1500 cm$^{-1}$.

EXAMPLE 150

1-[3-(2-Phenylpyrazolo[1,5-a]pyridin-3-yl)acryloyl]-4-(2-hydroxyethyl)piperidine (trans isomer).
IR (Nujol): 3400, 1640, 1590, 1530, 1510 cm$^{-1}$.

EXAMPLE 151

1-[3-(2-Phenylpyrazolo[1,5-a]pyridin-3-yl)acryloyl]-2-ethoxycarbonylpiperidine (trans isomer).
IR (film): 1725, 1635, 1585, 1505 cm$^{-1}$.

EXAMPLE 152

1-[2-Methyl-3-(2-phenylpyrazolo[1,5-a]pyridin-3-yl)acryloyl]-2-ethylpiperidine (trans isomer).
IR (Nujol): 1740, 1620, 1600, 1520 cm$^{-1}$.

EXAMPLE 153

1-[3-(2-Phenylpyrazolo[1,5-a]pyridin-3-yl)acryloyl]-2,2,6,6-tetramethylpiperidine (trans isomer).
IR (Nujol): 1640, 1580, 1510 cm$^{-1}$.

EXAMPLE 154

(2S)-1-[3-(2-Phenylpyrazolo[1,5-a]pyridin-3-yl)acryloyl]-2-methoxymethylpyrrolidine (trans isomer).
IR (Nujol): 1700, 1640, 1590, 1520 cm$^{-1}$.

EXAMPLE 155

1-[(2E,4E)-5-(2-Phenylpyrazolo[1,5-a]pyridin-3-yl)-2,4-pentadienoyl]-2-ethylpiperidine.
IR (Nujol): 1620, 1580, 1500 cm$^{-1}$.

(2R)-1-[3-{2-(3-Pyridyl)pyrazolo[1,5-a]pyridin-3-yl}acryloyl]-2-(2-hydroxyethyl)piperidine (trans isomer).
IR (Nujol): 3470, 1620, 1580 cm$^{-1}$.

EXAMPLE 157

N-Benzyl-N-methyl-3-(2-phenylpyrazolo[1,5-a]pyridin-3-yl)acrylamide (trans isomer).
IR (Nujol): 1610, 1510 cm$^{-1}$.

EXAMPLE 158

3-(2-Phenylpyrazolo[1,5-a]pyridin-3-yl)acryloyl]-3-azabicyclo[3.2.2]nonane (trans isomer).
IR (Nujol): 1630, 1580, 1500 cm$^{-1}$.

EXAMPLE 159

7-[3-(2-Phenylpyrazolo[1,5-a]pyridin-3-yl)acryloyl]-7-azabicyclo[2.2.1]heptane (trans isomer).
IR (Nujol): 1635, 1590, 1510 cm$^{-1}$.

EXAMPLE 160

1-[3-(2-Phenylpyrazolo[1,5-a]pyridin-3-yl)acryloyl]-perhydro-1H-azepine ½fumalate (trans isomer).
IR (Nujol): 1685, 1635, 1580, 1520 cm$^{-1}$.

EXAMPLE 161 n-Butyl 3-(2-phenylpyrazolo[1,5-a]pyridin-3-yl)acrylate (trans isomer).
IR (Nujol): 1690, 1620, 1510 cm$^{-1}$.

EXAMPLE 162

1-[3-(2-Phenylpyrazolo[1,5-a]pyridin-3-yl)acryloyl]2-methoxymethylpiperidine (trans isomer).
IR (Nujol): 1640, 1590, 1510, 1440, 1415 cm$^{-1}$.

EXAMPLE 163

1-[3-(2-Phenylpyrazolo[1,5-a]pyridin-3-yl)acryloyl]2-(2-methoxyethyl)piperidine (trans isomer).
IR (Nujol): 1635, 1590, 1510 cm$^{-1}$.

EXAMPLE 164

1-[3-(2-Phenylpyrazolo[1,5-a]pyridin-3-yl)acryloyl]2-acetoxymethylpiperidine (trans isomer).
IR (CHCl$_3$): 1740, 1640, 1590 cm$^{-1}$.

EXAMPLE 165

1-[3-(2-Phenylpyrazolo[1,5-a]pyridin-3-yl)acryloyl]2-(2-acetoxyethyl)piperidine (trans isomer).
IR (CHCl$_3$): 1725, 1635, 1585, 1515 cm$^{-1}$.

EXAMPLE 166

1-[3-(2-Phenylpyrazolo[1,5-a]pyridin-3-yl)acryloyl]-piperidine-2-carboxylic acid (trans isomer).
IR (Nujol): 3350, 1750, 1630, 1560, 1510 cm$^{-1}$.

EXAMPLE 167

1-[3-{2-(3-Aminophenyl)pyrazolo[1,5-a]pyridin-3-yl}acryloyl]-2-ethylpiperidine (trans isomer).
IR (Nujol): 3410, 3340, 3240, 1635, 1605 cm$^{-1}$.

EXAMPLE 168

1-[3-{2-(4-Aminophenyl)pyrazolo[1,5-a]pyridin-3-yl}acryloyl]-2-ethylpiperidine (trans isomer).
IR (Nujol): 3335, 3220, 1635, 1605, 1580 cm$^{-1}$.

EXAMPLE 169

1-[3-{2-(3-Acetamidophenyl)pyrazolo[1,5-a]pyridin-3-yl}acryloyl]-2-ethylpiperidine (trans isomer).
IR (Nujol): 3380, 1685, 1635 cm$^{-1}$.

EXAMPLE 170

1-[3-{2-(4-Acetamidophenyl)pyrazolo[1,5 a]pyridin-3-yl}acryloyl]-2-ethylpiperidine (trans isomer).
IR (Nujol): 3250, 1685, 1635, 1595 cm$^{-1}$.

EXAMPLE 171

1-[3-{2-(3-Methanesulfonamidophenyl)pyrazolo[1,5-a]pyridin-3-yl}acryloyl]-2-ethylpiperidine (trans isomer).
IR (Nujol): 3080, 1635, 1610 cm$^{-1}$.

EXAMPLE 172

1-[3-{2-(3-Methoxycarbonylaminophenyl)-pyrazolo[1,5-a]pyridin-3-yl}acryloyl]-2-ethylpiperidine (trans isomer).
IR (Nujol): 3260, 1725, 1640 cm$^{-1}$.

EXAMPLE 173

1-[3-{2-(3-Methylaminophenyl)pyrazolo[1,5-a]pyridin-3-yl}acryloyl]-2-ethylpiperidine (trans isomer)
IR (Nujol): 3500, 1635, 1580, 1510 cm$^{-1}$.

EXAMPLE 174

1-[3-{2-(3-Dimethylaminophenyl)pyrazolo[1,5-a]pyridin-3-yl}acryloyl]-2-ethylpiperidine (trans isomer)

IR (Nujol): 1640, 1600 cm$^{-1}$.

The following compounds (Examples 175 to 238) were obtained according to a similar manner to that of Example 25.

EXAMPLE 175

1-[3-(2-Phenylpyrazolo[1,5-a]pyridin-3-yl)acryloyl]2-ethylpiperidine ½fumalate (trans isomer).
IR (Nujol): 1705, 1635, 1580, 1540, 1510 cm$^{-1}$.

EXAMPLE 176

1-[3-(2-Phenylpyrazolo[1,5-a]pyridin-3-yl)acryloyl]-pyrrolidine (trans isomer).
IR (Nujol): 1640, 1590 cm$^{-1}$.

EXAMPLE 177

1-[3-(2-Phenylpyrazolo[1,5-a]pyridin-3-yl)acryloyl]-piperidine (trans isomer).
IR (Nujol):1630, 1580 cm$^{-1}$.

EXAMPLE 178

4-[3-(2-Phenylpyrazolo[1,5-a]pyridin-3-yl)acryloyl]-morpholine (trans isomer).
IR (Nujol): 1625, 1580 cm$^{-1}$.

EXAMPLE 179

N-Methyl-3-.(2-phenylpyrazolo[1,5-a]pyridin-3-yl)acrylamide (trans isomer).
IR (Nujol): 3275, 1640, 1605 cm$^{-1}$.

EXAMPLE 180

N-Isopropyl-3-(2-phenylpyrazolo[1,5-a]pyridin-3-yl)acrylamide (trans isomer).
IR (Nujol): 3275, 1640, 1600 cm$^{-1}$.

EXAMPLE 181

N,N-Dimethyl-3-(2-phenylpyrazolo[1,5-a]pyridin-3-yl)acrylamide (trans isomer).
IR (Nujol): 1640, 1590 cm$^{-1}$.

EXAMPLE 182

N-(Tricyclo[3.3.1.13.7]decan-1-yl)-3-(2-phenyl-pyrazolo[1,5-a]pyridin-3-yl)acrylamide (trans isomer).
IR (Nujol): 3280, 1650, 1590, 1535, 1500 cm$^{-1}$.

EXAMPLE 183

(2R)-1-[3-(2-Phenylpyrazolo[1,5-a]pyridin-3-yl)acryloyl]-2-ethylpiperidine (trans isomer).
IR (film): 2930,.2860, 1635, 1585 cm$^{-1}$.

EXAMPLE 184

(2S)-1-[3-(2-Phenylpyrazolo[1,5-a]pyridin-3-yl)acryloyl]-2-ethylpiperidine (trans isomer).
IR (film): 2930, 2860, 1635, 1585 cm$^{-1}$.

EXAMPLE 185

(2R)-1-[3-(2-Phenylpyrazolo[1,5-a]pyridin-3-yl)acryloyl]-2-(2-hydroxyethyl)piperidine (trans isomer).
IR (Nujol): 3350, 1640, 1575, 1520 cm$^{-1}$.

EXAMPLE 186

(2S)-1-[3-(2-Phenylpyrazolo[1,5-a]pyridin-3-yl)acryloyl]-2-(2-hydroxyethyl)piperidine (trans isomer).
IR (CHCl$_3$) 3330, 1635, 1570, 1520 cm$^{-1}$.

EXAMPLE 187

(2RS)-1-[3-(2-Phenylpyrazolo[1,5-a]pyridin-3-yl)acryloyl]-2-(2-hydroxyethyl)piperidine (trans isomer).
IR (Nujol): 3280, 1625, 1560, 1510 cm$^{-1}$.

EXAMPLE 188

N,N-Diethyl-3-(2-phenylpyrazolo[1,5-a]pyridin-3-yl)acrylamide (trans isomer).
IR (CHCl$_3$) 1640, 1595, 1520 cm$^{-1}$.

EXAMPLE 189

1-[3-(2-Phenylpyrazolo[1,5-a]pyridin-3-yl)acryloyl]2-methylpiperidine (trans isomer).
IR (CHCl$_3$): 1640, 1590, 1515 cm$^{-1}$.

EXAMPLE 190

1-[3-(2-Phenylpyrazolo[1,5-a]pyridin-3-yl)acryloyl]2-propylpiperidine (trans isomer).
IR (Nujol): 1640, 1580, 1510 cm$^{-1}$.

EXAMPLE 191

1-[3-(2-Phenylpyrazolo[1,5-a]pyridin-3-yl)acryloyl]2-hydroxymethylpiperidine (trans isomer).
IR (Nujol): 3320, 1635, 1575, 1500 cm$^{-1}$.

EXAMPLE 192

1-[3-(2-Phenylpyrazolo[1,5-a]pyridin-3-yl)acryloyl]4-(2-hydroxyethyl)piperidine (trans isomer).
IR (Nujol): 3400, 1640, 1590, 1530, 1510 cm$^{-1}$.

EXAMPLE 193

1-[3-(2-Phenylpyrazolo[1,5-a]pyridin-3-yl)acryloyl]2-ethoxycarbonylpiperidine (trans isomer).
IR (film): 1725, 1635, 1585, 1505 cm$^{-1}$.

EXAMPLE 194

1-[2-Methyl-3-(2-phenylpyrazolo[1,5-a]pyridin-3-yl)acryloyl]-2-ethylpiperidine (trans isomer).
IR (Nujol): 1740, 1620, 1600, 1520 cm$^{-1}$.

EXAMPLE 195

1-[3-(2-Phenylpyrazolo[1,5-a]pyridin-3-yl)acryloyl]2,2,6,6-tetramethylpiperidine (trans isomer).
IR (Nujol): 1640, 1580, 1510 cm$^{-1}$.

EXAMPLE 196

(2S)-1-[3-(2-Phenylpyrazolo[1,5-a]pyridin-3-yl)acryloyl]-2-methoxymethylpyrrolidine (trans isomer).
IR (Nujol): 1700, 1640, 1590, 1520 cm$^{-1}$.

EXAMPLE 197

1-[(2E,4E)-5-(2-Phenylpyrazolo[1,5-a]pyridin-3-yl)2,4-pentadienoyl]-2-ethylpiperidine.
IR (Nujol): 1620, 1580, 1500 cm$^{-1}$.

EXAMPLE 198

(2R)-1-[3-{2-(3-Pyridyl)pyrazolo[1,5-a]pyridin-3-yl}acryloyl]-2-(2-hydroxyethyl)piperidine (trans isomer).
IR (Nujol): 3470, 1620, 1580 cm$^{-1}$.

EXAMPLE 199

N-Benzyl-N-methyl-3-(2-phenylpyrazolo[1,5-a]pyridin-3-yl)acrylamide (trans isomer).
IR (Nujol): 1610, 1510 cm$^{-1}$.

EXAMPLE 200

3-[3-(2-Phenylpyrazolo[1,5-a]pyridin-3-yl)acryloyl]3-azabicyclo[3.2.2.]nonane (trans isomer).
IR (Nujol): 1630, 1580, 1500 cm$^{-1}$.

EXAMPLE 201

7-[3-(2-Phenylpyrazolo[1,5-a]pyridin-3-yl)acryloyl]7-azabicyclo[2.2.1]heptane (trans isomer).
IR (Nujol): 1635, 1590, 1510 cm$^{-1}$.

EXAMPLE 202

1-3-(2-Phenylpyrazolo[1,5-a]pyridin-3-yl)acryloyl]-perhydro-1H-azepine ½fumalate (trans isomer).
IR (Nujol): 1685, 1635, 1580, 1520 cm$^{-1}$.

EXAMPLE 203

1-[2-Bromo-3-(2-phenylpyrazolo[1,5-a]pyridin-3-yl)acryloyl]-2-ethylpiperidine.
MS: 437, 439 (M+).

EXAMPLE 204

Ethyl 3-[2-(3-pyridyl)pyrazolo[1,5-a]pyridin-3-yl]acrylate (trans isomer).
IR (Nujol): 1690, 1620 cm$^{-1}$.

EXAMPLE 205

Ethyl (2E, 4E)-5-(2-phenylpyrazolo[1,5-a]pyridin-3-yl)-2,4-pentadienoate.
IR (Nujol): 1705, 1605, 1500, 1260, 1235 cm$^{-1}$.

EXAMPLE 206

1-[3-(4-Methyl-2-phenylpyrazolo[1,5-a]pyridin-3-yl)acryloyl]-2-ethylpiperidine (trans isomer).
IR (film): 1630, 1580, 1540 cm$^{-1}$.

EXAMPLE 207

1-[3-(5-Methyl-2-phenylpyrazolo[1,5-a]pyridin-3-yl)acryloyl]-2-ethylpiperidine ½fumalate (trans isomer).
IR (Nujol): 1705, 1640 cm$^{-1}$.

EXAMPLE 208

1-[3-(7-Methyl-2-phenylpyrazolo[1,5-a]pyridin-3-yl)acryloyl]-2-ethylpiperidine (trans isomer).
IR (Nujol): 1620, 1570, 1535, 1505 cm$^{-1}$.

EXAMPLE 209

1-[3-{2-(3-Methoxyphenyl)pyrazolo[1,5-a]pyridin-3-yl}acryloyl]-2-ethylpiperidine (trans isomer).
IR (Nujol): 1635, 1605, 1575 cm$^{-1}$.

EXAMPLE 210

1-[3-{2-(4-Methoxyphenyl)pyrazolo[1,5-a]pyridin-3-yl}acryloyl]-2-ethylpiperidine (trans isomer).
IR (CHCl$_3$) 1625, 1610, 1575 cm$^{-1}$.

EXAMPLE 211

1-[3-{2-(2-Chlorophenyl)pyrazolo[1,5-a]pyridin-3-yl}acryloyl]-2-ethylpiperidine (trans isomer).
IR (film): 1635, 1580, 1515 cm$^{-1}$.

EXAMPLE 212

1-[3-{2-(4-Chlorophenyl)pyrazolo[1,5-a]pyridin-3-yl}acryloyl]-2-ethylpiperidine ½fumalate (trans isomer).
IR (Nujol): 1705, 1635, 1550, 1510 cm$^{-1}$.

EXAMPLE 213

1-[3-{2-(3-Nitrophenyl)pyrazolo[1,5-a]pyridin-3-yl}acryloyl]-2-ethylpiperidine ½fumalate (trans isomer).
IR (Nujol): 1710, 1635 cm$^{-1}$.

EXAMPLE 214

1-[3-{2-(4-Nitrophenyl)pyrazolo[1,5-a]pyridin-1-yl}acryloyl]-2-ethylpiperidine (trans isomer).
IR (Nujol): 1635, 1575, 1510 cm$^{-1}$.

EXAMPLE 215

1-[3-(2-Phenylpyrazolo[1,5-a]pyridin-3-yl)isocrotonoyl]-2-ethylpiperidine.
MS: 373 (M+).

EXAMPLE 216

1-[3-(7-Methoxy-2-phenylpyrazolo[1,5-a]pyridin-3-yl)acryloyl]-2-ethylpiperidine (trans isomer).
IR (Nujol): 1630, 1580, 1540, 1510 cm$^{-1}$.

EXAMPLE 217

1-[3-(4-Chloro-2-phenylpyrazolo[1,5-a]pyridin-3-yl)acryloyl]-2-ethylpiperidine ½fumalate (trans isomer).
IR (Nujol): 1680, 1620 cm$^{-1}$.

EXAMPLE 218

1-[3-(6-Chloro-2-phenylpyrazolo[1,5-a]pyridin-3-yl)acryloyl]-2-ethylpiperidine (trans isomer).
IR (film): 1630, 1580, 1505 cm$^{-1}$.

EXAMPLE 219

1-[3-{2-(2-Pyridyl)pyrazolo[1,5-a]pyridin-3-yl}acryloyl]-2-ethylpiperidine (trans isomer).
IR (Nujol): 1635, 1590, 1510 cm$^{-1}$.

EXAMPLE 220

(2S)-1-[3-{2-(3-Pyridyl)pyrazolo[1,5-a]pyridin-3-yl}acryloyl]-2-ethylpiperidine (trans isomer).
MR 360 (M+).

EXAMPLE 221

1-[3-(2-Isopropylpyrazolo[1,5-a]pyridin-3-yl)acryloyl]-2-ethylpiperidine (trans isomer).
IR (Nujol): 1620 cm$^{-1}$.

EXAMPLE 222

1-[3-{2-(3-Chlorophenyl)pyrazolo[1,5-a]pyridin-3-yl}acryloyl]-2-ethylpiperidine (trans isomer).
IR (Nujol): 1640, 1580, 1510 cm$^{-1}$.

EXAMPLE 223

1-[3-{2-(4-Pyridyl)pyrazolo[1,5-a]pyridin-3-yl}acryloyl]-2-ethylpiperidine (trans isomer).
IR (Nujol): 1640, 1605 cm$^{-1}$.

EXAMPLE 224 n-Butyl 3-(2-phenylpyrazolo[1,5-a]pyridin-3-yl)acrylate (trans isomer).
IR (Nujol): 1690, 1620, 1510 cm$^{-1}$.

EXAMPLE 225

1-[3-(2-Phenylpyrazolo[1,5-a]pyridin-3-yl)acryloyl]-2-methoxymethylpiperidine (trans isomer).
IR (Nujol): 1640, 1590, 1510, 1440, 1415 cm$^{-1}$.

EXAMPLE 226

1-[3-(2-Phenylpyrazolo[1,5-a]pyridin-3-yl)acryloyl]-2-(2-methoxyethyl)piperidine (trans isomer).
IR (Nujol): 1635, 1590, 1510 cm$^{-1}$.

EXAMPLE 227

1-[3-(2-Phenylpyrazolo[1,5-a]pyridin-3-yl)acryloyl]-2-acetoxymethylpiperidine (trans isomer).
IR (CHCl$_3$) 1740, 1640, 1590 cm$^{-1}$.

EXAMPLE 228

1-[3-(2-Phenylpyrazolo[1,5-a]pyridin-3-yl)acryloyl]-2-(2-acetoxyethyl)piperidine (trans isomer).
IR (CHCl$_3$): 1725, 1635, 1585, 1515 cm$^{-1}$.

EXAMPLE 229

1-[3-(2-Phenylpyrazolo[1,5-a]pyridin-3-yl)acryloyl]-piperidine-2-carboxylic acid (trans isomer).
IR (Nujol): 3350, 1750, 1630, 1560, 1510 cm$^{-1}$.

EXAMPLE 230

1-[3-{2-(3-Aminophenyl)pyrazolo[1,5-a]pyridin-3-yl}acryloyl]-2-ethylpiperidine (trans isomer).
IR (Nujol): 3410, 3340, 3240, 1635, 1605 cm$^{-1}$.

EXAMPLE 231

1-[3-{2-(4-Aminophenyl)pyrazolo[1,5-a]pyridin-3-yl}acryloyl]-2-ethylpiperidine (trans isomer).
IR (Nujol): 3.335, 3220, 1635, 1605, 1580 cm$^{-1}$.

EXAMPLE 232

1-[3-{2-(3-Acetamidophenyl)pyrazolo[1,5-a]pyridin-3-yl}acryloyl]-2-ethylpiperidine (trans isomer).
IR (Nujol): 3380, 1685, 1635 cm$^{-1}$.

EXAMPLE 233

1-[3-{2-(4-Acetamidophenyl)pyrazolo[1,5-a]pyridin3-yl}acryloyl]-2-ethylpiperidine (trans isomer).
IR (Nujol): 3250, 1685, 1635, 1595 cm$^{-1}$.

EXAMPLE 234

1-[3-{2-(3-Methanesulfonamidophenyl)pyrazolo[1,5-a]pyridin-3-yl}acryloyl]-2-ethylpiperidine (trans isomer).
IR (Nujol): 3080, 1635, 1610 cm$^{-1}$.

EXAMPLE 235

1-[3-{2-(3-Methoxycarbonylaminophenyl)-pyrazolo[1,5-a]pyridin-3-yl}acryloyl]-2-ethylpiperidine (trans isomer).
IR (Nujol): 3260, 1725, 1640 cm$^{-1}$.

EXAMPLE 236

1-[3-{2-(3-Methoxyaminophenyl)pyrazolo[1,5-a]pyridin-3-yl}acryloyl]-2-ethylpiperidine (trans isomer).
IR (Nujol): 3500, 1635, 1580, 1510 cm$^{-1}$.

EXAMPLE 237

1-[3-{2-(3-Dimethylaminophenyl)pyrazolo[1,5-a]pyridin-3-yl}acryloyl]-2-ethylpiperidine (trans isomer).
IR (Nujol): 1640, 1600 cm$^{-1}$.

EXAMPLE 238

1-[3-(2-Phenylpyrazolo[1,5-a]pyridin-3-yl)acryloyl]-4-methylpiperazine hydrochloride (trans isomer).
IR (Nujol): 2400, 1650, 1580, 1500 cm$^{-1}$.

The following compounds (Examples 239 and 240) were obtained according to a similar manner to that of Example 22.

EXAMPLE 239

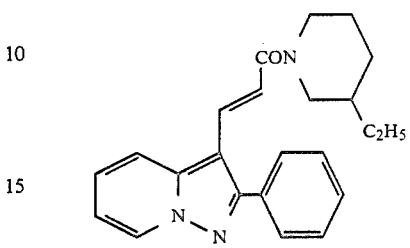

IR (CHCl$_3$): 1640, 1590 cm$^{-1}$.
NMR (CDCl$_3$, δ): 0.90 (3H, t, J=7.5Hz), 1.10–2.10 (7H, m), 2.20–3.10 (2H, m), 3.70–4.20 (2H, m), 6.68 (1H, d, J=18Hz), 6.85 (1H, t, J=8.0Hz),
7.27 (1H, t, J=8.0Hz), 7.30–7.54 (3H, m), 7.54–7.82 (3H, m), 7.93 (1H, d, J=18Hz), 8.47 (1H, d, J=8Hz)

EXAMPLE 240

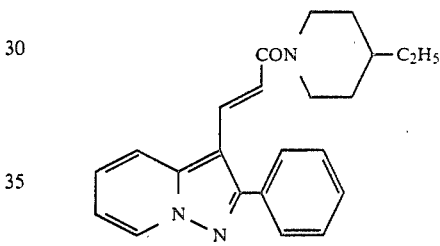

IR (CHCl$_3$): 1635, 1590, 1520 cm$^{-1}$.
NMR (CDCl$_3$, δ): 0.89 (3H, t, J=6.2Hz), 1.03–1.47 (4H, m), 1.72 (2H, d, J=11Hz), 2.78 (2H, t, J=13Hz), 4.22 (2H, broad), 6.60 (1H, d, J=16Hz), 6.76 (1H, td, J=7Hz and 1Hz), 7.06–7.67 (7H, m), 7.82 (1H, d, J=16Hz), 8.39 (1H, d, J=7Hz).
MS: 359 (M$^+$).

The following compounds (Examples 241 and 242) were obtained according to a similar manner to that of Example 62.

EXAMPLE 241

1-[3-(2-Phenylpyrazolo[1,5-a]pyridin-3-yl)acryloyl]-3-ethylpiperidine (trans isomer).
IR (CHCl$_3$): 1640, 1590 cm$^{-1}$.

EXAMPLE 242

1-[3-(2-Phenylpyrazolo[1,5-a]pyridin-3-yl)acryloyl]-4-ethylpiperidine (trans isomer).
IR (CHCl$_3$): 1635, 1590, 1520 cm$^{-1}$.

The following compounds (Examples 243 and 244) were obtained according to a similar manner to that of Example 25.

EXAMPLE 243

1-[3-(2-Phenylpyrazolo[1,5-a]pyridin-3-yl)acryloyl]-3-ethylpiperidine (trans isomer).
IR (CHCl$_3$): 1640, 1590 cm$^{-1}$.

EXAMPLE 244

1-[3-(2-Phenylpyrazolo[1,5-a]pyridin-3-yl)acryloyl]-4-ethylpiperidine (trans isomer).
IR (CHCl$_3$): 1635, 1590, 1520 cm$^{-1}$.

EXAMPLE 245

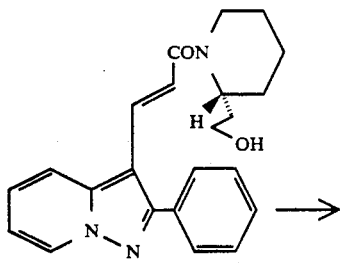

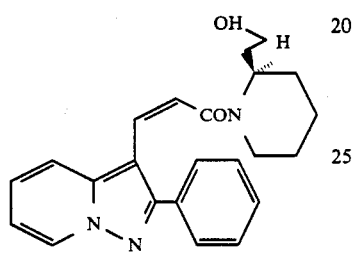

A solution of (2R)-1-[3-(2-phenylpyrazolo[1,5-a]pyridin-3-yl)acryloyl]-2-(2-hydroxyethyl)piperidine (trans isomer) (0.50 g) in methylene chloride (3 ml) was irradiated with sun light by the window and stood for 4 hours. Then the solution was evaporated in vacuo. The residue was chromatographed on alumina TLC with a mixture of methylene chloride and ethyl acetate (5:1) as an eluent. The parts containing the object compound were combined and extracted with methylene chloride. The extracts were evaporated in vacuo to give (2R)-1-[3-(2-Phenylpyrazolo[1,5-a]pyridin-3-yl)acryloyl]-2-(2-hydroxyethyl)piperidine (cis isomer) (0.15 g) as an oil.
IR (CHCl$_3$): 1630, 1590, 1520 cm$^{-1}$.
NMR (CDCl$_3$, δ): 0.73-2.01 (8H, m), 1.70 (1H, s), 2.75 (1H, td, J=13.5Hz and 3Hz), 3.00-4.10 (3H, m), 4.52-4.81 (1H, m), 6.08 (1H, d, J=12Hz), 6.78 (1H, td, J=7Hz and 1Hz), 6.84 (1H, d, J=12Hz), 7.06-7.87 (7H, m),
8.41 (1H, d, J=7Hz).
MS: 375 (M+).

EXAMPLE 246

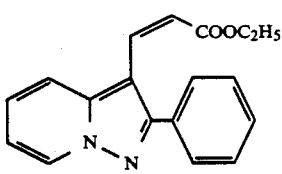

Ethyl 3-(2-phenylpyrazolo[1,5-a]pyridin-3-yl)acrylate (cis isomer) was obtained according to a similar manner to that of Example 245.
mp: 54° to 55° C.
IR (Nujol): 1705, 1635 cm$^{-1}$.
NMR (CDCl$_3$, δ): 1.17 (3H, t, J=7.0Hz), 4.13 (2H, q, J=7Hz), 6.05 (1H, d, J=12.0Hz), 6.50-7.97 (9H, m), 8.48 (1H, dd, J=6.5Hz).

Analysis Calcd. for C$_{17}$H$_{16}$N$_2$O$_2$: C 73.65, H 5.52, N 9.58 Found: C 74.24, H 5.92, N 9.49.

EXAMPLE 247

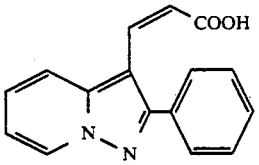

3-(2-Phenylpyrazolo[1,5-a]pyridin-3-yl)acrylic acid (cis isomer) was obtained according to a similar manner to that of Example 8.
mp: 153° to 155° C.
IR (Nujol): 1680, 1630, 1600 cm$^{-1}$.
NMR (CDCl$_3$, δ): 6.15 (1H, d, J=12.0Hz), 6.70-7.92 (9H, m), 8.53 (1H, dd, J=7.0Hz and 1.0Hz), 8.97-9.60 (1H, m).
Analysis Calcd. for C$_{16}$H$_{12}$N$_2$O$_2$:
C 72.71, H 4.58, N 10.60. Found: C 72.87, H 4.67, N 10.58.

EXAMPLE 248

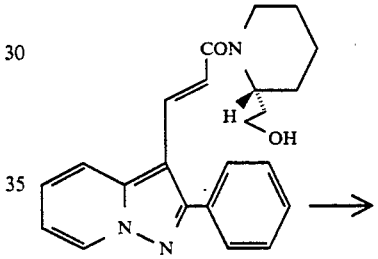

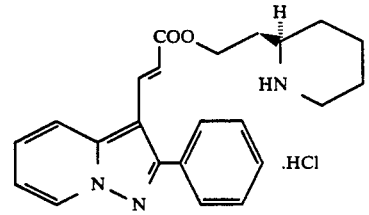

A solution of (2R)-1-[3-(2-phenylpyrazolo[1,5-a]pyridin-3-yl)acryloyl]-2-(2-hydroxyethyl)piperidine (trans isomer) (0.50 g) in methylene chloride (saturated with HCl gass) (3 ml) was stirred at room temperature. Methylene chloride (saturated with HC gass) (3 ml) was added 4 times to that solution during 7 hours. The reaction mixture was evaporated in vacuo. Tetrahydrofuran (5 ml) was added to the residue and stirred The resulting precipitates were collected by filtration and dried to give (2R)-2-[2-{3-(2-phenylpyrazolo[1,5-a]pyridin-3-yl)acryloyloxy}ethyl]piperidine hydrochloride (trans isomer) (0.53 g).
mp: 223.5-225° C.
IR (Nujol): 1715, 1705, 1620, 1590, 1515 cm$^{-1}$.
NMR (DMSO-d$_6$, δ): 1.18-3.30 (10H, m), 3.48 (1H, d, J=12Hz), 4.32 (2H, t, J=6Hz), 6.25 (1H, d, J=16Hz), 6.87 (1H, t, J=7Hz), 7.27-7.90 (7H, m), 7.88 (1H, d, J=16Hz), 8.50 (1H, d, J=7Hz).
MS: 375 (M+).
[α]$_2$$^{25.6°}$ = −7.35° (c=1.06, EtOH).

EXAMPLE 249

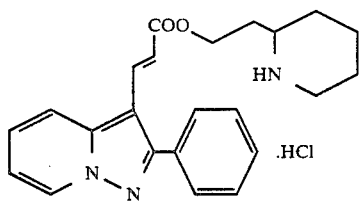

2-[2-{3-(2-Phenylpyrazolo[1,5-a]pyridin-3-yl)acryloyloxy}ethyl]piperidine hydrochloride (trans isomer) was obtained according to a similar manner to that of Example 248.

mp: 217°–220° C.

IR (Nujol): 1715, 1705, 1620, 1590, 1515 cm$^{-1}$.

What we claim is:

1. A method for the treatment of melancholia, gout, hyperuricemia, myocardiac infarction, arteriosclerosis obliterans, thrombophlebitis, cerebral infarction, transient ischemic attack and angina pectoris which comprises administering an effective amount of a compound of the formula:

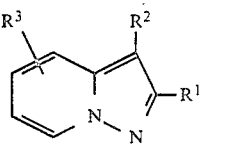

wherein $R^1$ is lower alkyl, phenyl which may be substituted by 1 to 3 substituents selected from the group consisting of halogen, lower alkoxy, nitro, amino and protected amino, or pyridyl, $R^2$ is a group of the formula:

—A—$R^6$ wherein $R^6$ is a group of the formula:

—CO$R_N$ wherein $R_N$ is piperidino which may be substituted by 1 to 4 substituents selected from the group consisting of lower alkyl, hydroxy(lower)alkyl, lower alkoxy(lower)alkyl, lower alkanoyloxy(lower)alkyl, lower alkoxycarbonyl and carboxy; pyrrolidin-1-yl which may be substituted by lower alkoxy(lower)alkyl; perhydroazepin-1-yl; piperazin-1-yl which may be substituted by lower alkyl; morpholino; 7-azabicyclo[2.2.1]heptan-7-yl; or 3-azabicyclo[3.2.2]nonan-3-yl, and A is lower alkyl, lower alkenyl or lower alkynyl, each of which may be substituted by halogen, $R^3$ is hydrogen, lower alkyl, lower alkoxy or halogen, or a pharmaceutically acceptable salt thereof to a human being or animal.

* * * * *